United States Patent
Kotton et al.

(10) Patent No.: US 10,449,221 B2
(45) Date of Patent: Oct. 22, 2019

(54) DIFFERENTIATION OF STEM CELLS INTO THYROID TISSUE

(71) Applicants: TRUSTEES OF BOSTON UNIVERSITY, Boston, MA (US); BETH ISRAEL DEACONESS MEDICAL CENTER, INC., Boston, MA (US)

(72) Inventors: Darrell Kotton, Newton, MA (US); Maria Serra, Turin (IT); Anthony N. Hollenberg, Newton, MA (US); Anita A. Kurmann, Cambridge, MA (US)

(73) Assignees: TRUSTEES OF BOSTON UNIVERSITY, Boston, MA (US); BETH ISRAEL DEACONESS MEDICAL CENTER, INC., Boston, MA (US)

(*) Notice: Subject to any disclaimer, the term of this patent is extended or adjusted under 35 U.S.C. 154(b) by 119 days.

(21) Appl. No.: 15/223,603

(22) Filed: Jul. 29, 2016

(65) Prior Publication Data
US 2017/0027994 A1 Feb. 2, 2017

Related U.S. Application Data

(60) Provisional application No. 62/242,053, filed on Oct. 15, 2015, provisional application No. 62/198,350, filed on Jul. 29, 2015.

(51) Int. Cl.
| | |
|---|---|
| *A61K 35/55* | (2015.01) |
| *A61K 38/22* | (2006.01) |
| *A61K 38/24* | (2006.01) |
| *C12N 5/071* | (2010.01) |

(52) U.S. Cl.
CPC .............. *A61K 35/55* (2013.01); *A61K 38/22* (2013.01); *A61K 38/24* (2013.01); *C12N 5/0617* (2013.01); *C12N 2500/30* (2013.01); *C12N 2500/42* (2013.01); *C12N 2501/11* (2013.01); *C12N 2501/115* (2013.01); *C12N 2501/117* (2013.01); *C12N 2501/155* (2013.01); *C12N 2501/375* (2013.01); *C12N 2501/415* (2013.01); *C12N 2513/00* (2013.01); *C12N 2533/90* (2013.01)

(58) Field of Classification Search
None
See application file for complete search history.

(56) References Cited

U.S. PATENT DOCUMENTS

2014/0329318 A1 11/2014 Rajagopal et al.

OTHER PUBLICATIONS

Antonica et al., "Generation of functional thyroid from embryonic stem cells", Nature 491(7422):66-71 (2012).
Arufe et al., "Directed Differentiation of Mouse Embryonic Stem Cells into Thyroid Follicular Cells", Endocrinology 147(6):3007-3015 (2006).
Arufe et al., Differentiation of Murine Embryonic Stem Cells to Thyrocytes Requires Insulin and Insulin-Like Growth Factor-1 Biochem. Biophys. Res. Commun. 381(2):264-70 (2009).
Bilodeau et al., "Identification of a Proximal Progenitor Population from Murine Fetal Lungs with Clonogenic and Multilineage Differentiation Potential", Stem Cell Reports 3:634-649 (2014).
Cheng et al., "Self-Renewing Endodermal Progenitor Lines Generated from Human Pluripotent Stem Cells", Cell Stem Cell 10:371-384 (2012).
Domyan et al., "Signaling through BMP receptors promotes respiratory identity in the foregut via repression of Sox2", Development 138:971-981 (2011).
Ghaedi et al., "Human iPS cell-derived alveolar epithelium repopulates lungs extracellular matrix" J. Clin. Invest. 123 (11):4950-4962 (2013).
Goss et al., "Wnt2/2b and β-Catenin Signaling Are Necessary and Sufficient to Specify Lung Progenitors in the Foregut", Dev. Cell 17:290-298 (2009).
Gotoh et al., "Generation of Alveolar Epithelial Spheroids via Isolated Progenitor Cells from Human Pluripotent Stem Cells", Stem Cells Reports 3:394-403 (2014).
Ishii et al., "Region-Specific Expression of Chicken Sox2 in the Developing Gut and Lung Epithelium: Regulation by Epithelial-Mesenchymal Interactions", Dev. Dyn. 213:464-475 (1998).
Krude et al., "Choreoathetosis, hypothyroidism, and pulmonary alterations due to human NKX2-1 haploinsufficiency", J. Clin. Invest. 109(4):475-480 (2002).
Kurmann et al., "Regeneration of Thyroid Function by Transplantation of Differentiated Pluripotent Stem Cells", Cell Stem Cell 17:1-16 (2015).
Lau et al., "Stem Cells and Regenerative Medicine in Lung Biology and Diseases", Mol. Ther. 20(6):1116-1130 (2012).
Longmire et al., "Efficient derivation of purified lung and thyroid progenitors from embryonic stem cells", Cell Stem Cell 10(4):398-411 (2012).
Ma et al., "Thyrotropin-Independent Induction of Thyroid Endoderm from Embryonic Stem Cells by Activin A", Endocrinology 150(4):1970-1975 (2009).
McCracken et al., "Modeling human development and disease in pluripotent stem cell-derived gastric organoids", Nature 516(7531:400-404 (2014).

(Continued)

*Primary Examiner* — Blaine Lankford
(74) *Attorney, Agent, or Firm* — Nixon Peabody, LLP

(57) ABSTRACT

Embodiments herein relate in vitro methods of stem cell differentiation into thyroid hormone producing cells and tissues, and methods of use of these cells.

17 Claims, 22 Drawing Sheets
(18 of 22 Drawing Sheet(s) Filed in Color)
Specification includes a Sequence Listing.

(56) References Cited

OTHER PUBLICATIONS

Mou et al. "Generation of Multipotent Lung and Airway Progenitors from Mouse ESCs and Patient-Specific Cystic Fibrosis iPSCs", Cell Stem Cell 10:385-397 (2012).

Murry et al., "Differentiation of Embryonic Stem Cells to Clinically Relevant Populations: Lessons from Embryonic Development", 132:661-680 (2008).

Pagliuca et al., "Generation of Functional Human Pancreatic β Cells In Vitro", Cell 159:428-439 (2014).

Postiglione et al., "Role of the thyroid-stimulating hormone receptor signaling in development and differentiation of the thyroid gland", PNAS 99(24):15462-15467 (2002).

Sewell et al., "Generation of thyroid follicular cells from pluripotent stem cells: potential for regenerative medicine", Front. Endocrinol. 5(96):1-6 (2014).

Zuckier et al., "Kinetics of Perrhenate Uptake and Comparative Biodistribution of Perrhenate, Pertechnetate, and Iodide by NaI Symporter-Expressing Tissues In Vivo" J. Nucl. Med. 45(3):500-507 (2004).

Hilfer et al., "Follicle formation in the embryonic chick thryroid", Zeitschrift für Zellforschung and Mikroskopische Anatomie, 92(2):256-69 (1968).

Jiang et al., "Differentiation of E14 Mouse Embryonic Stem Cells into Thyrocytes In Vitro", Thyroid, 20(1):77-84 (2010).

Lancaster et al., "Organogenesis in a dish: Modeling development and disease using organoid technologies" Science, 345(6194):1247125 (2014).

Lin et al., "Committing Embryonic Stem Cells to Differentiate into Thyrocyte-Like Cells in Vitro", Endocrinology 144 (6):2644-2649 (2003).

Mallette et al., "Growth in culture of trypsin dissociated thyroid cells from adult rats", Exp Cell Res, 41(3):642-51 (1966).

Martin et al., "Preservation of functioning human thyroid organoids in the scid mouse: 1. System characterization" J Clin Endocrinol Metab, 77(2):305-10 (1993).

Nkx2-1

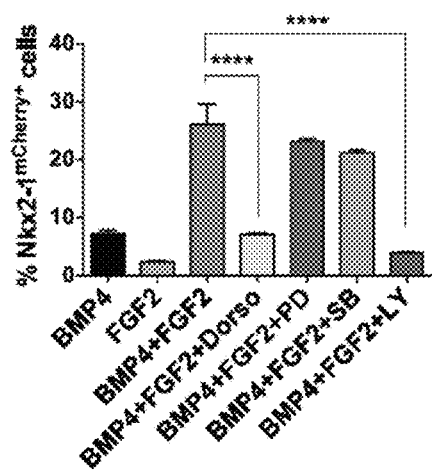
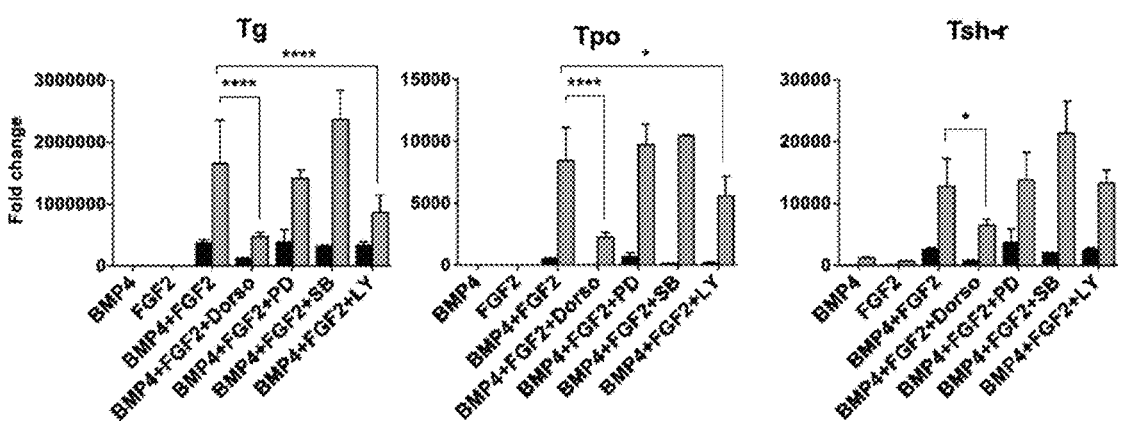

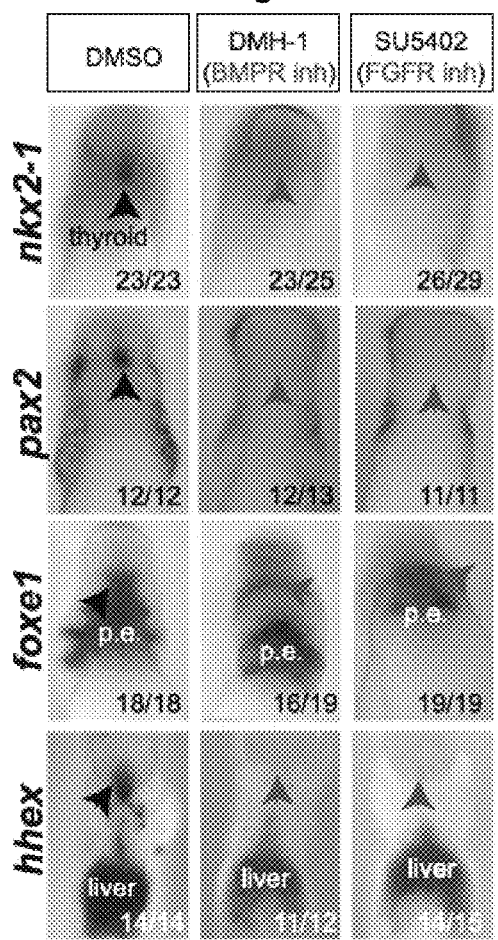
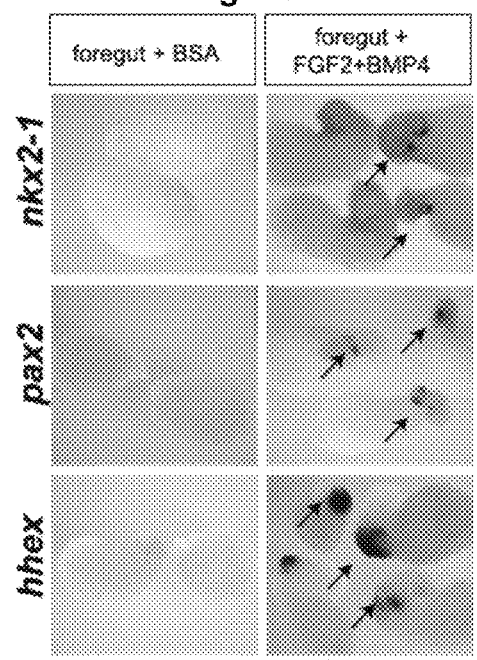
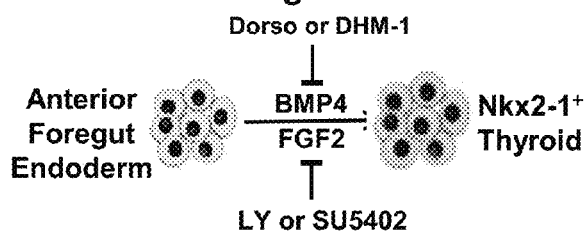
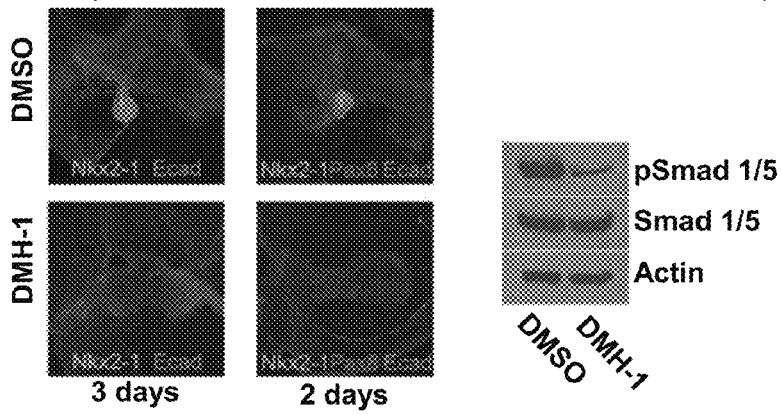
Fig. 4a
Fig. 4b
Fig. 4c
Fig. 4d

Day 14

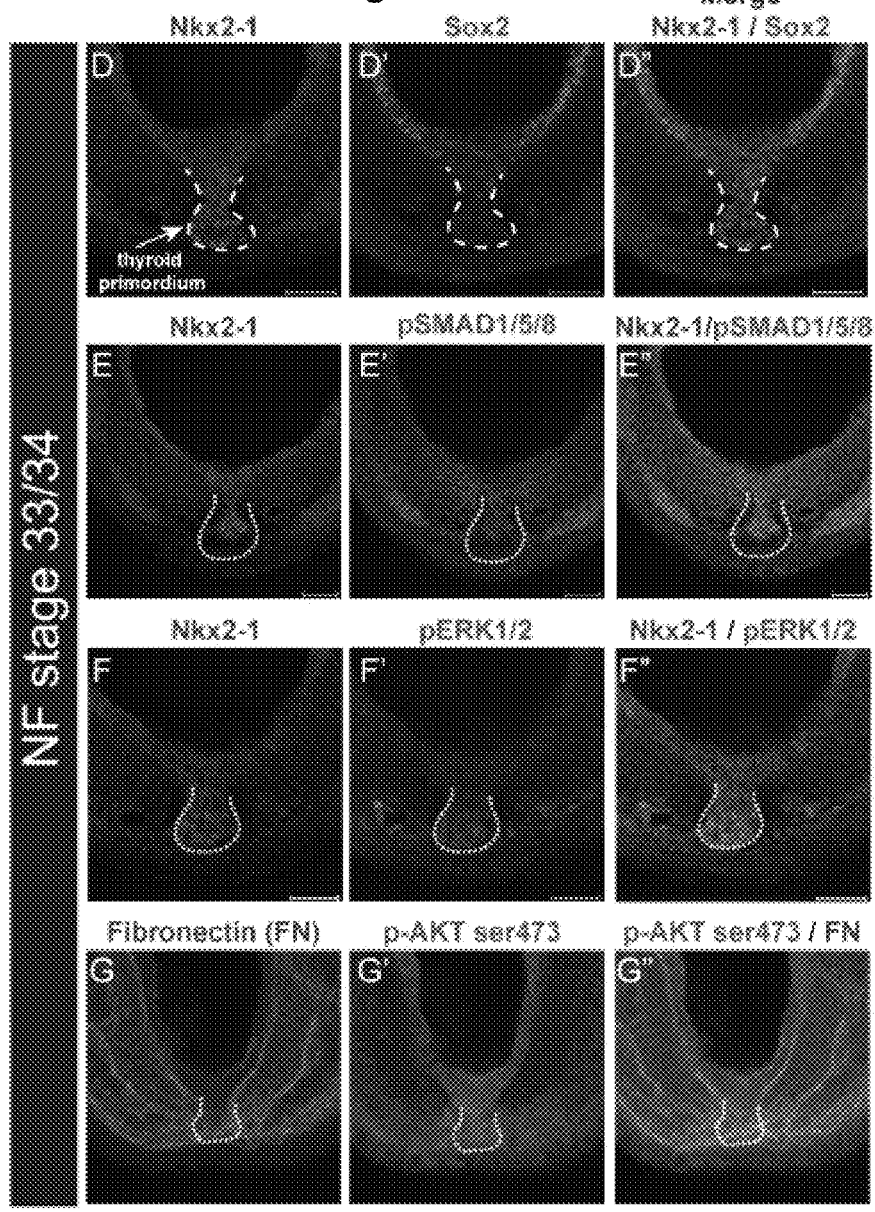

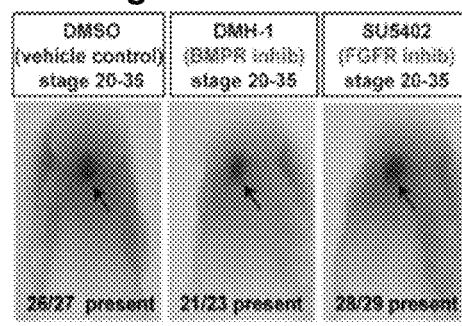
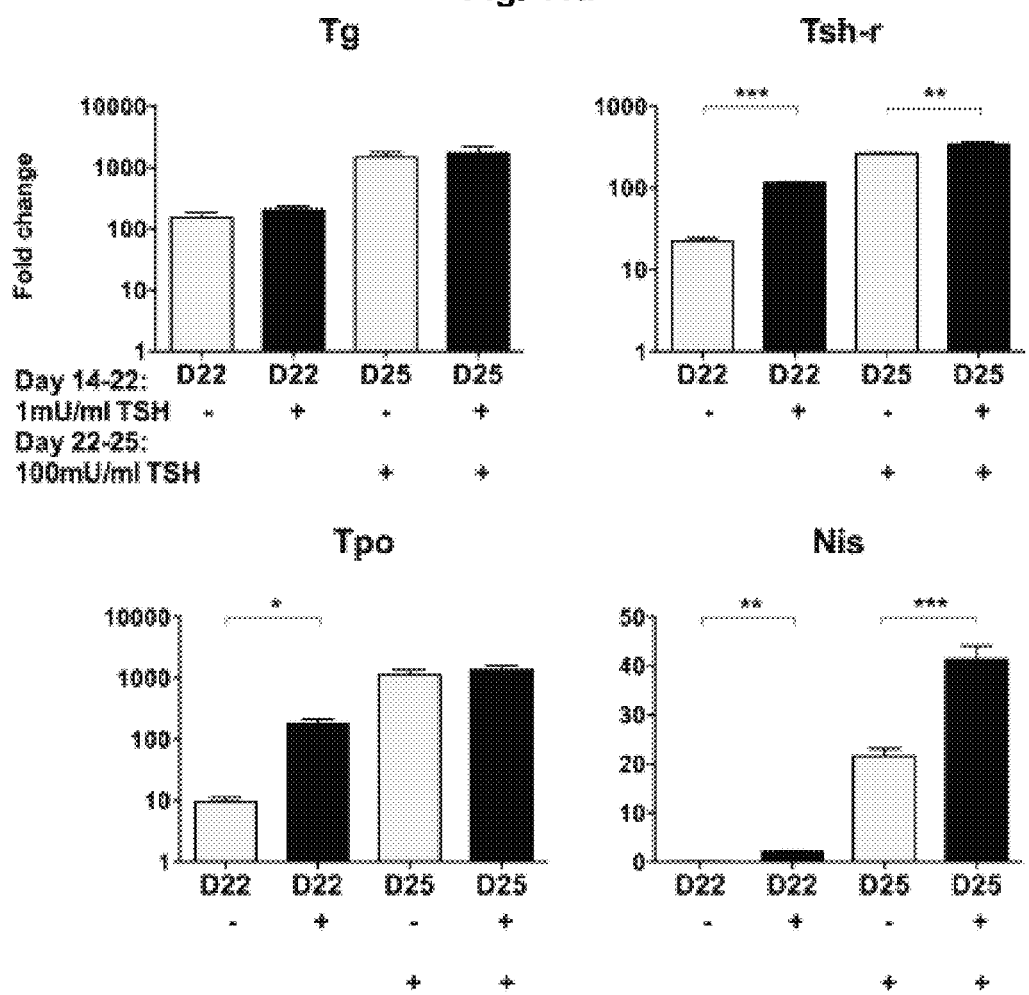

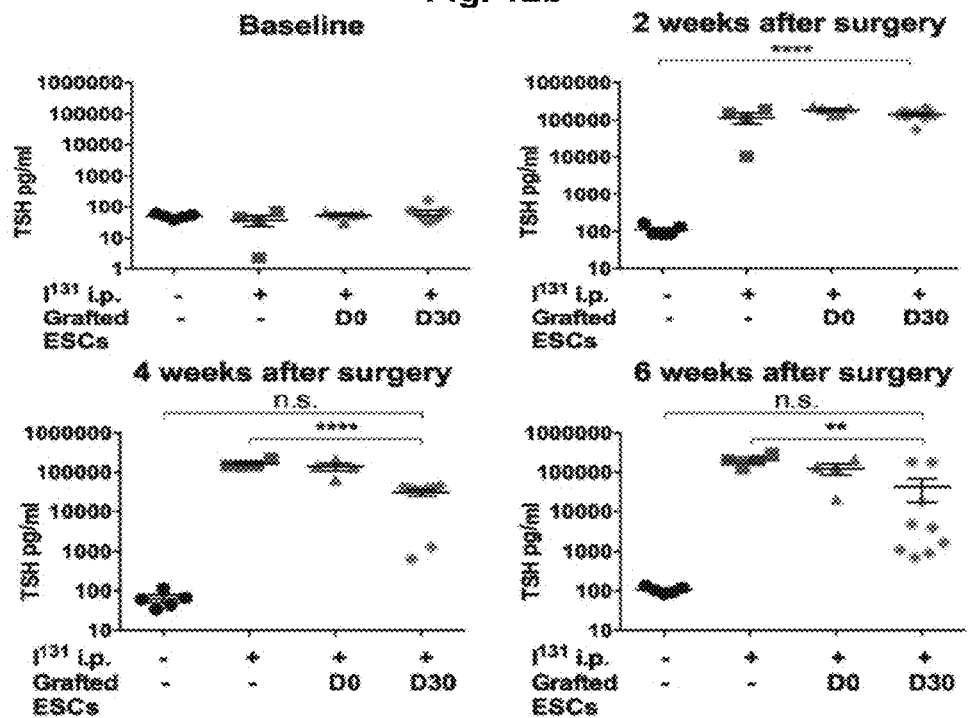
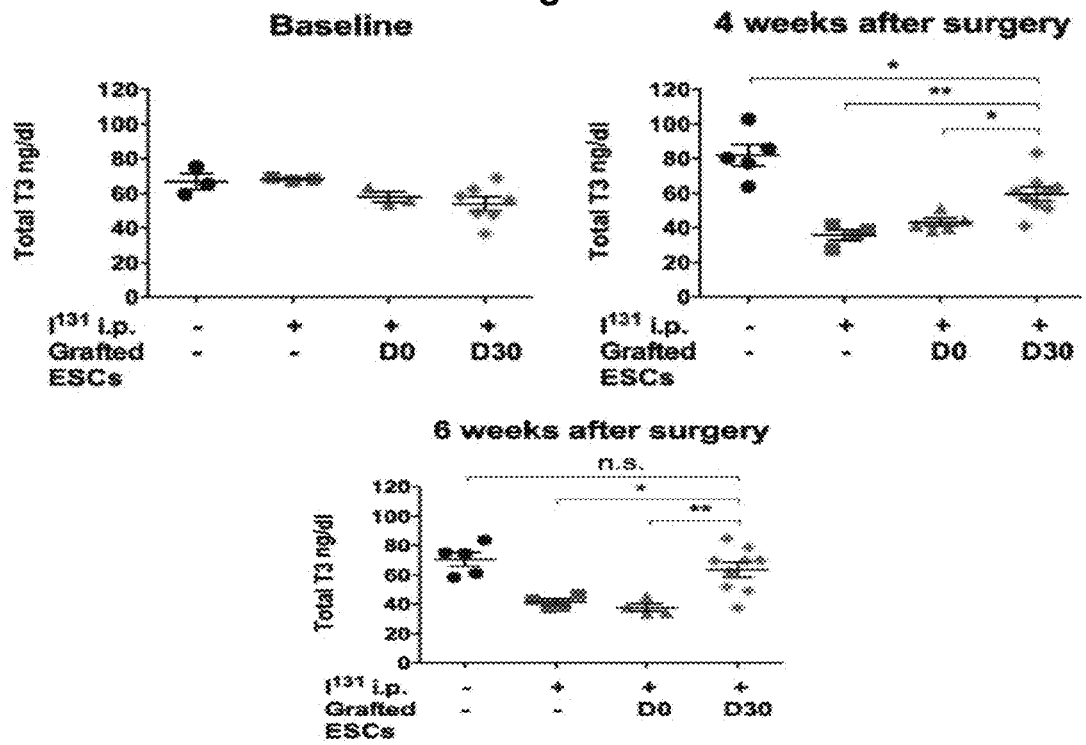

SEQUENCE LISTING

<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggtggagagc accaagacag a                                                    21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 2
gccggagtcg acaatgatg                                                      19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
agccgggaca agccactgaa ggat                                                24
```

DIFFERENTIATION OF STEM CELLS INTO THYROID TISSUE

CROSS REFERENCE TO RELATED APPLICATIONS

This application claims benefit under 35 U.S.C. § 119(e) of the U.S. provisional applications No. 62/198,350 filed Jul. 29, 2015, and No. 62/242,053 filed Oct. 15, 2015, the contents of each are incorporated herein by reference in its entirety.

GOVERNMENT SUPPORT

This invention was made with Government Support under Contract No. HL095993 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 28, 2016, is named 701586-085532-US_SL.txt and is 1,035 bytes in size.

FIELD OF THE DISCLOSURE

This disclosure relates to stem cell differentiation and in vitro stem cell-derived thyroid hormone producing cells and tissues.

BACKGROUND

The endocrine system is a network of glands that produce and release hormones that help control many important body functions, including the body's ability to change calories into energy that powers cells and organs. The endocrine system influences how the heart beats, how the bones and tissues grow, even one's ability to reproduce. It plays a vital role in whether or not a person develops diabetes, thyroid disease, growth disorders, sexual dysfunction, and a host of other hormone-related disorders.

When the endocrine glands malfunction by under producing or releasing the essential hormones or when the glands are destroyed or removed, e.g. due to cancer, it would then be necessary to replace the missing essential hormones.

The derivation of pluripotent stem cells into endocrine tissues (PSC-derived endocrine tissues), such as pancreatic islets or thyroid follicles, provides particularly attractive opportunities to replace the missing essential hormones in vivo in the afflicted persons. PSC-derived endocrine tissues can achieve the envisioned in vivo function without orthotopic transplantation because the engraftment of these hormone-secreting tissues in any location with access to circulating blood would potentially achieve function and even clinical rescue from a variety of common endocrine diseases, including diabetes mellitus and hypothyroidism. Indeed, the differentiation of PSCs into pancreatic islet-like cells has produced cells capable of secreting insulin in vivo following transplantation (Cheng et al., 2012; Pagliuca et al., 2014).

Recent progress in the differentiation of PSCs in vitro has allowed the derivation of desired cell lineages and in some instances, the in vitro self-assembly of the differentiated lineage cells into 3D structures, referred to as organoids (Lancaster and Knoblich, 2014; McCracken et al., 2014). However, transplantation and in vivo function of these engineered cells have been less successful, typically due to poor engraftment or failure to structurally integrate orthotopically transplanted PSC-derived cells into native recipient tissues.

Thyroid epithelial cells have been engineered from stem cells in two separate approaches: (1) by forced, over-expression of integrated genes encoding multiple transcription factors, NKX2.1 and PAX8, in the stem cells (Antonica et al., 2012), and (2) by growing the stem cells in growth factor supplemented media (Longmire et al., 2012). In marked contrast to the poor in vivo efficacy of the stem cell-derived organoids above described, the thyroid epithelial cells generated to date from PSCs through the forced over-expression of integrated genes encoding multiple transcription factors displayed in vivo functional potential (Antonica et al., 2012).

Without resorting to the over-expression of integrated genes encoding multiple transcription factors, the in vitro directed differentiation of PSCs into thyroid epithelial cells using growth factor supplemented media, however, do not produce the same outlook as forced over-expression PSC-derived engineered cells. This method only resulted in immature PSC-derived engineered cells that fail to express the full genetic program necessary for either iodine metabolism or functional thyroid hormone biosynthesis (Arufe et al., 2006; Arufe et al., 2009; Jiang et al., 2010; Longmire et al., 2012; Ma et al., 2009). In Longmire et al. for example, the six-factor cocktail serum-free media was sufficient to direct initial differentiation of embryonic stem cell (ESC)-derived definitive endodermal cells to enter the thyroid lineage. This directed differentiation was assessed by the expression of thyroid epithelial-specific genes, such as thyroglobulin (Tg). However, these thyroid lineage cells did not progress further into the thyroid differentiation pathway; these cells did not display full thyroid maturation as the genes encoding all proteins required for iodine metabolism and thyroid hormone biosynthesis were not robustly expressed, such as the sodium iodine symporter (Nis) and thyroid peroxidase (Tpo).

The primary hurdle preventing the successful differentiation of PSCs into mature thyroid cells has been a lack of knowledge of the signaling pathways that regulate early thyroid embryonic development. "Directed differentiation" of PSCs utilizes sequential exposure of undifferentiated PSCs to a series of growth factor-supplemented media designed to recapitulate the sequence of developmental milestones that normally occurs during the embryonic differentiation of a desired cell lineage. This approach, based on the observation that PSCs resemble the inner cell mass of the developing blastocyst embryo, has been employed to successfully produce a wide variety of non-thyroid lineages from PSCs (Murry and Keller, 2008), but the derivation of functional thyroid follicular epithelial cells has not yet been achieved. The derivation of thyroid epithelial cells via directed differentiation remains a compelling goal given the known capacity of thyroid epithelia, once mature, to self-organize and form follicular structures in vitro. Indeed trypsinized thyroid follicular epithelial cells from developing or adult animals have been shown to self-aggregate and form follicles during in vitro culture (Hilfer et al., 1968; Mallette and Anthony, 1966; Martin et al., 1993). Moreover, recent work has demonstrated that thyroid cells generated from ESCs through the forced over-expression of transcription factors also formed follicles in vitro or after transplantation in vivo (Antonica et al., 2012; Ma et al., 2015).

SUMMARY OF THE DISCLOSURE

Embodiments of the present disclosure are based on the discovery that a combinatorial bone morphogenetic protein (BMP) and fibroblast growth factor (FGF) signaling pathways, are necessary for the entry and differentiation of PSCs into the thyroid lineage, and also for the maturation of the PSC-derived thyroid progenitor cells into mature thyroid cells that would secrete thyroid hormones and would be responsive to the thyroid stimulating hormone (TSH). Previously, PSC-derived thyroid progenitor or thyroid lineage cells had been produced using a six-growth factor serum free growth medium that include bone morphogenetic protein 4 (BMP4) and fibroblast growth factor 2 (basic) (FGF2) but these thyroid progenitor/lineage cells do not continue to mature into thyroid hormone secreting cells. The problem to solve here is how to get PSCs all the way to mature thyroid cells. So far, there is no method for making mature thyroid cells from PSCs such that the thus-derived thyroid cells behave like mature thyroid cells. For examples, mature thyroid cells secrete thyroid hormones, are responsive to TSH, and are able to metabolize iodine.

In contrast, in this present discovery, PSCs, when cultured in serum-free medium containing BMP4 and FGF2, the BMP4 and FGF2 direct entry and differentiation of the PSCs into the thyroid lineage. Once the thyroid lineage is determined, TSH and dexamethasone then direct the maturation of the PSC-derived thyroid progenitor/lineage cells into mature thyroid hormone secreting and TSH-responsive cells.

One of the main advantages of this discovery is that thyroid hormone secreting cells that are also TSH-responsive can now be made in vitro. There is currently no naturally occurring thyroid hormone secreting/TSH-responsive cells available. Excised and dissociated thyroid cells cannot be kept alive in culture in vitro. Thus there is no such available cells for use in transplantation to treat a patient having hypothyroidism.

Accordingly, it is the objective of the disclosure to provide an ex vivo or in vitro, cell culture method of making cells that produce thyroid hormone secreting and thyroid stimulating hormone responsive cells from PSCs without the over-expression of multiple transcription factors in the stem cells in order to induce differentiation into the thyroid lineage and subsequent maturation to mature thyroid hormone secreting and TSH-responsive cells. For example, without the forced over-expression of NKX2.1 and/or PAX8 in the PSCs.

It is also the objective of the disclosure to provide a population of PSC-derived thyroid cells that secrete thyroid hormones, are responsive to TSH, and are able to metabolize iodine. These are thyroid follicular epithelial cells. These cells can then be used for transplantation into a subject who is lacking or deficient in thyroid hormones. These cells are also useful as research tools for studying the differentiation signaling pathways involved in thyroid lineage differentiation and thyroid cell maturation, and also for studying the effects of drugs and chemicals on the secretory activities of the mature thyroid cells.

Moreover, it is the objective of the disclosure to provide a method of treating thyroid hormone insufficiency or deficiency by transplanting a population of PSC-derived thyroid cells that secrete thyroid hormone, are responsive to TSH, and metabolize iodine into a subject who is lacking or deficient in thyroid hormone. For example, a condition known as hypothyroidism.

Furthermore, it is the objective of the disclosure to provide a cell culture-based model system comprising PSC-derived thyroid follicular epithelial cells. These cells can organize into a 3D organoid structure. This model system can be used for research purposes.

Accordingly, in one embodiment, provided herein is an ex vivo or in vitro method for producing a functional thyroid follicular epithelial cell from a thyroid progenitor cell. The ex vivo or in vitro method for producing a thyroid follicular epithelial cell comprising (a) culturing a thyroid progenitor cell in a differentiation medium under condition and time sufficient to further differentiate the thyroid progenitor cell along the thyroid lineage, wherein the differentiation medium comprising fibroblast growth factor 2 (basic) (FGF2), wherein the thyroid progenitor cell co-expresses a NK2 homeobox 1 (Nkx2-1) protein and a paired box 8 (Pax8) protein, and wherein the co-expression of Nkx2.1 and Pax8 are the products of endogenous genes within the cell, and the Nkx2.1 and Pax8 co-expressing thyroid progenitor cell does not comprise exogenously delivered nucleic acid sequences encoding for the co-expression of Nkx2.1 and Pax8 in the cell; and (b) then culturing the thyroid progenitor cell of step (a) in a maturation medium comprising dexamethasone and cAMP, dexamethasone and thyroid stimulating hormone (TSH), TSH, or fibroblast growth factors (such as FGF2 and FGF10) under condition and time sufficient to produce a Nkx2-1+/Pax8+ co-expressing cell that also expresses early and mature thyroid markers: thyroglobulin (Tg+), thyroid stimulating hormone receptor (Tsh+), sodium iodine symporter (Nis+), and thyroid peroxidase (Tpo+).

Accordingly, in another embodiment, the disclosure provides an ex vivo or in vitro method for producing a functional thyroid follicular epithelial cell from an endodermal cell. The ex vivo or in vitro method for producing a thyroid follicular epithelial cell comprising (a) culturing an endodermal cell in a thyroid lineage culture medium under condition and time sufficient to differentiate the endodermal cell into the thyroid lineage without exogenously delivered nucleic acid sequences resulting in the forced over-expression of a NK2 homeobox 1 (Nkx2-1) protein and a paired box 8 (Pax8) protein in the endodermal cell, thereby producing a thyroid progenitor cell, wherein the differentiation culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF), thereby producing Nkx2-1 and Pax8 (Nkx2-1+/Pax8+) co-expressing thyroid progenitor cell therefrom, but not a Nkx2-1 expressing or a Pax8 expressing cell: (b) culturing a thyroid progenitor cell in a differentiation medium under condition and time sufficient to further differentiate the thyroid progenitor cell along the thyroid lineage, the differentiation medium comprising fibroblast growth factor 2 (basic) (FGF2); and (c) then culturing the thyroid progenitor cell of step (b) in a thyroid maturation medium comprising dexamethasone and cAMP, dexamethasone and thyroid stimulating hormone (TSH), TSH or fibroblast growth factors (such as FGF2 and FGF10) under condition and time sufficient to produce a Nkx2-1+/Pax8+ co-expressing cell that also express early and mature thyroid markers: thyroglobulin (Tg+), thyroid stimulating hormone receptor (Tsh+), sodium iodine symporter (Nis+), and thyroid peroxidase (Tpo+).

Accordingly, in another embodiment, the disclosure provides an ex vivo or in vitro method for producing a functional thyroid follicular epithelial cell from a pluripotent stem cell (PSC). The ex vivo or in vitro method for producing a thyroid follicular epithelial cell from a PSC cell comprising (a) culturing a pluripotent stem cell (PSC) in a culture medium under conditions sufficient to initiate entry and formation into an endodermal cell; (b) culturing the endodermal cell in a thyroid lineage culture medium under condition and time sufficient to differentiate the endodermal cell into the thyroid lineage without exogenously delivered nucleic acid sequences resulting in the forced over-expression of a NK2 homeobox 1 (Nkx2-1) protein and a paired box 8 (Pax8) protein in the endodermal cell, thereby producing a thyroid progenitor cell, wherein the differentiation culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF), thereby producing Nkx2-1 and Pax8 (Nkx2-1+/Pax8+) co-expressing thyroid progenitor cell therefrom, but not a Nkx2-1 expressing or a Pax8 expressing cell; (c) culturing the thyroid progenitor cell with a differentiation medium under condition and time sufficient to further differentiate the thyroid progenitor cell along the thyroid lineage, the differentiation medium comprising fibroblast growth factor 2 (basic) (FGF2); and (d) culturing the thyroid progenitor cell of step (c) with a thyroid maturation medium comprising dexamethasone and cAMP, dexamethasone and thyroid stimulating hormone (TSH), TSH, or or fibroblast growth factors (such as FGF2 and FGF10) under condition and time sufficient to produce a Nkx2-1+/Pax8+ co-expressing cell that also expresses early and mature thyroid markers: thyroglobulin (Tg+), thyroid stimulating hormone receptor (Tsh+), sodium iodine symporter (Nis+), and thyroid peroxidase (Tpo+).

In one embodiment of the disclosed method, the thyroid progenitor cell is prepared by contacting an endodermal cell with a thyroid lineage culture medium to differentiate the endodermal cell into the thyroid lineage without exogenously delivered nucleic acid sequences resulting in the forced over-expression of the Nkx2-1 protein and the Pax8 protein in the endodermal cell, thereby producing a Nkx2.1+ and Pax8+ thyroid progenitor cell, wherein the thyroid lineage culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF).

In one embodiment of any disclosed method, the thyroid progenitor cell does not comprise an exogenously nucleic acid coding for the transcription factor, NK2 homeobox 1 (Nkx2-1).

In one embodiment of any disclosed method, the thyroid progenitor cell does not comprise an exogenously nucleic acid coding for the transcription factor, paired box 8 protein (Pax8).

In one embodiment of any disclosed method, the thyroid progenitor cell does not comprise exogenously nucleic acids coding for the transcription factors, Nkx2-1 and Pax8.

In one embodiment of any disclosed method, the endodermal cell is an anterior/foregut endodermal cell.

In one embodiment of any disclosed method, the endodermal cell does not comprise an exogenously nucleic acid coding for the transcription factor, NK2 homeobox 1 (Nkx2-1).

In one embodiment of any disclosed method, the endodermal cell does not comprise an exogenously nucleic acid coding for the transcription factor, paired box 8 protein (Pax8).

In one embodiment of any disclosed method, the endodermal cell does not comprise exogenously nucleic acids coding for the transcription factors, Nkx2-1 and Pax8.

In one embodiment of any disclosed method, the differentiation medium further comprising a fibroblast growth factor. In one embodiment, the fibroblast growth factor is FGF10. In another embodiment, the fibroblast growth factor is FGF2.

In one embodiment of any disclosed method, the differentiation medium further comprising BMP4.

In one embodiment of any disclosed method, the differentiation medium further comprising TSH.

In one embodiment of any one of disclosed method, the PSC is an induced pluripotent stem (iPS) cell, or an embryonic stem cell (ESC) having at least a diploid gene locus encoding the homeodomain-containing transcription factor, NK2 homeobox 1 protein (Nkx2-1), whereby a diploid expression of Nkx2-1 is induced.

In one embodiment of any disclosed method, the PSC has previously been developed into an endodermal lineage cell.

In one embodiment of any disclosed method, the PSC has previously been developed or differentiated into an anterior or foregut endodermal lineage cell.

In one embodiment of any disclosed method, the PSC has previously been developed or differentiated into a thyroid progenitor cell.

In one embodiment of any disclosed method, the PSC does not comprise an exogenously delivered nucleic acid coding for the transcription factor, NK2 homeobox 1 (Nkx2-1). In other words, the PSC contain at least an extra copy of a nucleic acid sequence coding for Nkx2-1, in addition to the endogenous diploid copy typical of a diploid cell.

In one embodiment of any disclosed method, the PSC does not comprise an exogenously nucleic acid coding for the transcription factor, paired box 8 protein (Pax8).

In one embodiment of any disclosed method, the PSC does not comprise exogenously nucleic acids coding for the transcription factors, Nkx2-1 and Pax8.

In one embodiment of any disclosed method, the PSC are cultured in the described medium for a period of time, for example, for about 6 to about 20 days.

In one embodiment of any disclosed method, the maturation medium further comprises BMP4 and/or FGF2.

In one embodiment of any disclosed method, the maturation medium is used for a period of time, for examples, for about 1 to about 10 days, for about 6 to about 30 days, or about 14 to about 30 days.

In one embodiment of any disclosed method, the resultant Nkx2-1+/Pax8+/Tg+/Tsh+/Nis+/Tpo+ cells also express Forkhead Box E1 protein (Foxe1) and thyroidally-expressed homeobox protein (Hhex).

In one embodiment of any disclosed method, the resultant Nkx2-1+/Pax8+/Tg+/Tsh+/Nis+/Tpo+ cells can be grown in culture and retain the ability to proliferate and retain their thyroid function, ie., secreting thyroid hormones, responsive to TSH etc. Natural thyroid follicular epithelial cells cannot be dissociated and grown in culture in a stable state.

In one embodiment of any disclosed method, the resultant Nkx2-1+/Pax8+/Tg+/Tsh+/Nis+/Tpo+ cells express lower levels of TPO and NIS compared to natural thyroid follicular epithelial cells.

In one embodiment of any disclosed method, the resultant Nkx2-1+/Pax8+/Tg+/Tsh+/Nis+/Tpo+ cells also express epithelial markers E-Cadhedrin (E-Cad) and epithelial cell adhesion molecule (EpCam).

In one embodiment of any disclosed method, the resultant Nkx2-1+/Pax8+/Tg+/Tsh+/Nis+/Tpo+ cells comprise one or more exogenous copies of nucleic acid sequence that encode a reprogramming factor such as Oct4, Sox2, cMyc, Klf4, Nanog, Lin 28 and Glis1. In some embodiments, combinations of reprogramming factors are used. For example, the cell has a combination of three or four reprogramming factors consisting of Oct4, Sox2, cMyc (optional), and Klf4, or a combination of four reprogramming factors consisting of Oct4, Sox2, Nanog, and Lin 28.

In one embodiment of any disclosed method, the method further comprising selecting for Nkx2-1+/Pax8+ expressing cells obtained and removing Nkx2-1+/Pax8−, Nkx2-1−/Pax8−, and Nkx2-1−/Pax8+ expressing cells.

In one embodiment of any disclosed method, the method further comprising determining diploid expression of Nkx2-1 in the resultant cells.

In one embodiment of any disclosed method, the method further comprising selecting for Nkx2-1+/Pax8+/Tg+/Tsh+/Nis+/Tpo+/expressing cells obtained.

In one embodiment of any disclosed method, the method further comprising selecting for Foxe1+/Hhex+ expressing cells obtained.

In one embodiment of any disclosed method, the method further comprising selecting for E-Cad+/EpCam+ expressing cells obtained.

In one embodiment of any disclosed method, the method further comprising selecting for Sftpc−/Scgb1a1− expressing cells obtained.

In one embodiment of any disclosed method, the Nkx2-1+/Pax8+ expressing cells are cultured in a 3D matrix support material.

In one embodiment of the disclosed method, the 3D matrix support material is matrigel.

In one embodiment, the disclosure provides a population of thyroid follicular epithelial cells produced by any of the methods described herein. In one embodiment, the population of cells further comprises a cryopreservative for cryostorage. In another embodiment, the population of cells further comprises serum or plasma or a pharmaceutically acceptable carrier. In one embodiment, the thyroid follicular epithelial cells carry one or more exogenous copies of a nucleic acid sequence that encode a reprogramming factor such as Oct4, Sox2, cMyc, Klf4, Nanog, Lin 28 and Glis1. In one embodiment, the thyroid follicular epithelial cells can be grown in culture in vitro and retain the ability to proliferate and retain their thyroid function.

In one embodiment of the disclosed population of thyroid follicular epithelial cells of described herein, the cells synthesize and secrete thyroid hormones in vivo. In another embodiment, the thyroid follicular epithelial cells synthesize and secrete thyroid hormones in vitro in culture.

In one embodiment, the disclosure provides a composition comprising a population of thyroid follicular epithelial cells described herein. In one embodiment, the composition further comprises a cryopreservative for cryostorage. In another embodiment, the composition further comprises serum or plasma or a pharmaceutically acceptable carrier. In one embodiment, the cells are the thyroid follicular epithelial cells prepared by any one of the method described herein. In one embodiment, the cells are PSC-derived the thyroid follicular epithelial cells prepared by any one of the method described herein. In another embodiment, the PSC-derived thyroid follicular epithelial cells synthesize and secrete thyroid hormones. In one embodiment, the thyroid follicular epithelial cells carry one or more exogenous copies of a nucleic acid sequence that encode a reprogramming factor such as Oct4, Sox2, cMyc, Klf4, Nanog, Lin 28 and Glis1. In one embodiment, the thyroid follicular epithelial cells can be grown in culture in vitro and retain the ability to proliferate and retain their thyroid function.

In one embodiment, the disclosure provides a pharmaceutical composition comprising a population of thyroid follicular epithelial cells described herein and a pharmaceutically acceptable carrier. In another embodiment, the pharmaceutical composition further comprises serum or plasma. In another embodiment, the pharmaceutical composition does not comprise tissue culture medium. In one embodiment, the cells are the PSC-derived thyroid follicular epithelial cells prepared by any one of the method described herein. In another embodiment, the PSC-derived thyroid follicular epithelial cells synthesize and secrete thyroid hormones. In one embodiment, the thyroid follicular epithelial cells carry one or more exogenous copies of a nucleic acid sequence that encode a reprogramming factor such as Oct4, Sox2, cMyc, Klf4, Nanog, Lin 28 and Glis1. In one embodiment, the thyroid follicular epithelial cells can be grown in culture in vitro and retain the ability to proliferate and retain their thyroid function.

In one embodiment, the disclosure provides a 3-D construct comprising a population of thyroid follicular epithelial cells described herein and a matrix or scaffold material. In one embodiment of the 3-D construct, the thyroid follicular epithelial cells are embedded the matrix or scaffold material and have organized into a 3D organiod structure. In one embodiment, the cells are the PSC-derived thyroid follicular epithelial cells prepared by any one of the method described herein. In another embodiment, the PSC-derived thyroid follicular epithelial cells synthesize and secrete thyroid hormones. In one embodiment, the thyroid follicular epithelial cells carry one or more exogenous copies of a nucleic acid sequence that encode a reprogramming factor such as Oct4, Sox2, cMyc, Klf4, Nanog, Lin 28 and Glis1. In one embodiment, the thyroid follicular epithelial cells can be grown in culture in vitro and retain the ability to proliferate and retain their thyroid function.

In one embodiment, the disclosure provides a method for treating hypothyroidism in a subject in need thereof comprising transplanting a population of thyroid follicular epithelial cells described herein into the subject. In one embodiment, the cells are the PSC-derived thyroid follicular epithelial cells prepared by any one of the method described herein. In another embodiment, the PSC-derived thyroid follicular epithelial cells synthesize and secrete thyroid hormones.

In one embodiment, the disclosure provides a method for treating hypothyroidism in a subject in need thereof comprising transplanting a 3-D construct comprising a population of thyroid follicular epithelial cells and a matrix or scaffold material described herein into the subject. In one embodiment, the cells are the PSC-derived thyroid follicular epithelial cells prepared by any one of the method described herein. In another embodiment, the PSC-derived thyroid follicular epithelial cells synthesize and secrete thyroid hormones.

In one embodiment of the disclosed treatment method described herein, the method further comprises selecting a subject diagnosed of having hypothyroidism.

In one embodiment of the disclosed treatment method described herein, the method further comprises harvesting a population of pluripotent stem cells from the subject to ex vivo produce a population of thyroid follicular epithelial cell for transplantation.

In one embodiment of the disclosed treatment method described herein, the PSCs are harvested from the bone marrow (BM), adipose tissue (AT), peripheral blood (PB), placenta, and umbilical cord blood (UBC). In one embodiment, the cells are harvested from a subject who is also to receive the thyroid follicular epithelial cell produced with the harvested PSCs. The donor of the PSCs is also the recipient of the PSC-derived thyroid follicular epithelial cells. The PSC-derived thyroid follicular epithelial cells are autologous to the recipient subject. When the donor subject is different from the recipient subject, the PSC-derived thyroid follicular epithelial cells are non-autologous to the recipient subject, usually allogenic to the recipient subject when the cells are at least HLA matched.

In one embodiment of the disclosed treatment method described herein, the thyroid follicular epithelial cells are autologous or allogenic to the subject.

In one embodiment of the disclosed treatment method described herein, the thyroid follicular epithelial cells are cryopreserved prior to transplantation into the subject.

In one embodiment, the disclosure provides a population of thyroid follicular epithelial cells produced ex vivo from a population of pluripotent stem cells for use in the treatment of hypothyroidism.

In one embodiment, the disclosure provides a population of thyroid follicular epithelial cells produced ex vivo from a population of thyroid progenitor cells for use in the treatment of hypothyroidism.

In one embodiment, the disclosure provides a population of thyroid follicular epithelial cells produced ex vivo from a population of endodermal cells for use in the treatment of hypothyroidism.

In one embodiment, the disclosure provides a population of thyroid follicular epithelial cells produced ex vivo from a population of thyroid progenitor cells for use in the manufacture of medicament in the treatment of hypothyroidism.

In one embodiment, the disclosure provides a population of thyroid follicular epithelial cells produced ex vivo from a population of endodermal cells for use in the manufacture of medicament in the treatment of hypothyroidism.

In one embodiment, the disclosure provides a population of thyroid follicular epithelial cells produced ex vivo from a population of pluripotent stem cells for use in the manufacture of medicament in the treatment of hypothyroidism.

DEFINITIONS

The term "functional" in the context of the PSC-derived thyroid epithelial cells or any thyroid follicular epithelial cell described herein means that these cells can metabolize iodine, secretes thyroid hormones, express enzymes necessary for thyroid hormone synthesis and iodide metabolism, and respond to the presence of TSH by secreting thyroid hormones.

As used herein, being able to metabolize iodine in reference to a cell means the cell, at the minimum, expresses the enzymes necessary for thyroid hormone synthesis, and uptake and store iodine. In some embodiments, the cells express of sodium/iodine symporter, and/or iodotyrosine deiodinase, and/or thyroid peroxidase, and/or thyroglobulin (Tg).

As used herein, the term "an endodermal cell" refers to a cell from the endoderm. The endoderm is the innermost layer of cells or tissue of an embryo in early development, or the parts derived from this, which include the lining of the gut and associated structures. In some embodiments, an endodermal cell would express at the minimum, but not limited to the following markers: CD184 (CXCR4), SOX17, FOXA2 and c-Kit. In some embodiments, an endodermal cell would lack expression of known ectoderm, mesoderm and pluripotency markers.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a thyroid or lung progenitor cell), which in turn can differentiate into other types of precursor cells further down the pathway (such as a thyroid precursor), and then to an end-stage differentiated cell, such as a thyroid follicular epithelial cell which plays a characteristic role in a certain tissue type, and may or may not retain the capacity to proliferate further.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present disclosure can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

The term "carrier" in the context of a pharmaceutical carrier refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

The term "pharmaceutically acceptable carriers" excludes tissue culture medium. In another embodiment, "pharmaceutically acceptable carriers" includes serum or plasma.

As used herein, the terms "administering" refers to the placement of the PSC-derived thyroid epithelial cells or the composition comprising the PSC-derived thyroid epithelial cells into a subject in need thereof by a method or route which results in at least partial localization of the PSC-derived thyroid epithelial cells at a desired site. The PSC-derived thyroid epithelial cells, or the composition comprising the PSC-derived thyroid epithelial cells, or the 3D constructs comprising thyroid epithelial cells and matrix/scaffold materials can be administered by any appropriate route which results in an effective treatment in the subject. In one embodiment, "administering" refers to direct implanting or transplanting the PSC-derived thyroid epithelial cells into the subject.

The term "effective amount" means an amount of PSC-derived thyroid epithelial cells sufficient to provide at least some amelioration of the symptoms associated with hypothyroidism. In one embodiment, the "effective amount" means an amount of PSC-derived thyroid epithelial cells would increase the thyroid hormones in a subject having hypothyroidism.

As used herein the term "comprising" or "comprises" is used in reference to compositions, methods, and respective component(s) thereof, that are essential to the disclosure, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The PSC cells or the PSC-derived thyroid epithelial cells can be autologous/autogenic ("self") or non-autologous ("non-self," e.g., allogeneic, syngeneic or xenogeneic). "Autologous," as used herein, refers to cells from the same subject.

"Allogeneic," as used herein, refers to cells of the same species that differ genetically to the cell in comparison.

"Syngeneic," as used herein, refers to cells of a different subject that are genetically identical to the cell in comparison.

"Xenogeneic," as used herein, refers to cells of a different species to the cell in comparison. In preferred embodiments, the cells of the disclosure are allogeneic.

A "subject," as used herein, includes any animal that exhibits a symptom of hypothyroidism described herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. In another embodiment, the subject is a human.

In one embodiment, as used herein "treatment" or "treating," includes any beneficial or desirable effect on the symptoms of the hypothyroidism condition, and may include even increase in the amount of thyroid hormones in circulation in the subject. In another embodiment, treatment can involve optionally either the reduction or amelioration of symptoms of the disease or condition. "Treatment" does not necessarily indicate complete eradication or cure of the disease or condition, or associated symptoms thereof.

The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a pluripotent cell which itself is derived from a pluripotent cell, and so on. While each of these pluripotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "pluripotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

As used herein, the term "a progenitor cell" refers to refer to an immature or undifferentiated cell that has the potential later on to mature (differentiate) into a specific cell type, for example, a blood cell, a skin cell, a bone cell, or a hair cells. A progenitor cell also can proliferate to make more progenitor cells that are similarly immature or undifferentiated.

BRIEF DESCRIPTION OF THE DRAWINGS

This patent application file contains at least one drawing executed in color. Copies of this patent or patent application publication with color drawing(s) will be provided by the Office upon request and payment of the necessary fee.

FIG. 1a. Schematic of protocols compared for directed differentiation of ESCs into Nkx2-1+ cells.

FIG. 1b. Representative sort gates used to purify Nkx2-1GFP+ cells on Day 14, showing efficiency of specification in each indicated media.

FIG. 1c. Schematic of wildtype (WT) vs targeted Nkx2-1 alleles in the Nkx2-1GFP and Nkx2-1mCherry reporter ESC lines. Boxes represent exons. WT=wild type allele, UTR=untranslated region, IRES=internal ribosomal entry site, pA=polyadenylation site.

FIG. 1d. Representative sort gate on Day 14 used to sort Nkx2-1mCherry+ cell specified with WB+2.

FIG. 1e. mRNA expression of the indicated markers by real time RT-PCR at several time points of the differentiation, comparing the Nkx2-1GFP and Nkx2-1mCherry ESC lines. Bars indicate average fold change in gene expression over day 0 ESCs±SEM $2^{(-\Delta\Delta CT)}$; n=2 independent experiments). (Note all D14 and D26 RT-qPCR analyses are of sorted cells or their outgrowth, except preS=presorted comparison population.).

FIG. 2a. Representative E14.5 mouse embryo carrying Nkx2-1GFP and Pax8tdTomato trace reporters showing no apparent overlap between Nkx2-1GFP and Pax8tdTomato trace reporter signal.

FIG. 2b. Dissection of E14.5 mouse embryo anterior foregut showing the developing lung and thyroid, with Nkx2-1GFP and Pax8tdTomato trace signal overlapping (merge) in the thyroid but not the lung. Note: spherical Nkx2-1+/Pax8− ultimobranchial bodies adjacent to each of the two Nkx2-1+/Pax8+ thyroid lobes.

FIG. 2c. Schematic of induced pluripotent stem cell (iPSC) derivation from mouse embryonic fibroblasts (MEFs) by lentiviral-mediated transduction of the STEM-CCA vector encoding reprogramming factors, Oct4, Klf4, Sox2, and cMyc. Note that iPSCs can also be obtained with STEMCCA vector encoding three reprogramming factors, Oct4, Klf4, and Sox2.

FIG. 2d. Representative image of the resulting iPSCs, stained for the pluripotency marker Alkaline Phosphatase.

FIG. 2e. Comparison of the four different sorted populations from FIG. 2f. Cells were purified on Day 14 using the gate indicated and replated for differentiation until day 25 (Fold change mRNA expression on D25 over D0 by RT-qPCR; $2^{(-\Delta\Delta CT)}$). Only D14 cells double positive for Nkx2-1GFP+ and Pax8tdTomato trace+ are thyroid competent. Bars indicate average fold change in Nkx2-1 expression over ESCs±SEM (n=3 independent clones).

FIG. 2f. Representative FACS plot on Day 14 of differentiation of the iPSC line from FIGS. 2c-2d.

FIG. 2g. Comparison of the four different sorted populations from FIG. 2f. Cells were purified on Day 14 using the gate indicated and replated for differentiation until day 25 (Fold change mRNA expression on D25 over D0 by RT-qPCR; $2^{(-\Delta\Delta CT)}$). Only D14 cells double positive for Nkx2-1GFP+ and Pax8tdTomato trace+ are thyroid competent. Bars indicate average fold change in Pax 8, Foxe1, Hhex and Thyroglobulin (Tg) expression over ESCs±SEM (n=3 independent clones).

FIGS. 3a-3d show that BMP and FGF signaling are necessary for thyroid lineage specification of ESC-derived definitive endoderm.

FIG. 3a. Representative gates used to sort Nkx2-1mCherry+ cells specified with only FGF2, only BMP4 or FGF2+BMP4 on Day 14 of the differentiation.

FIG. 3b. Fold change mRNA expression on D26 over D0 by RT-qPCR; $2^{(-\Delta\Delta CT)}$. Cells were purified on Day 14 using the gate indicated in FIG. 3a and replated for differentiation until day 26. Cells specified with both BMP4 and FGF2 are highly enriched for thyroid competence.

FIG. 3c. Quantitation by flow cytometry of the % of Nkx2-1mCherry+ cells specified on Day 14 using different specification media (Day 6 to Day 14) containing where indicated 4 tM of Dorsomorphin, 20 tM of PD98059 (PD), 10 tM of SB203580 (SB) or 25 tM of LY294002 (LY). Error bars indicate mean±sd (n=3 biological replicates).

FIG. 3d. mRNA expression of the indicated markers by real time RT-PCR on Day 26 of the differentiation of the Nkx2-1 mCherry ESC line, comparing the specification media used in FIG. 3c and showing Dorsomorphin and LY affected thyroid lineage differentiation. Bars indicate average fold change in gene expression [$2^{(-\Delta\Delta CT)}$] over D0 ESCs±SD (n=3 biological replicates). 2-way ANOVA (FIGS. 3a and 3c) and 1-way ANOVA (b) *p~0.05, p~0.01, *p~0.001, ****p~0.0001.

FIGS. 4a-4d show that BMP and FGF signaling are necessary and sufficient for thyroid specification in *Xenopus*.

FIG. 4a. In vivo pharmacological loss-of-function using antagonists of type I BMP receptor (DMH-1) or FGF receptor (SU5402) activity. Whole embryos were cultured in the antagonists from stage NF13-20 and assayed by in-situ hybridization for the indicated genes at stage NF35. The number of embryos with the displayed phenotype is indicated.

FIG. 4b. FGF and BMP signaling is sufficient to induce thyroid gene expression in dissected *Xenopus* foregut endoderm explants. Explants were dissected at stage NF15, cultured in either BSA alone or in rhFGF2+rhBMP4 protein until stage NF35, and assayed by in-situ hybridization for the indicated genes.

FIG. 4c. Schematic of chemical inhibition of BMP4 or FGF2 signalling blocking thyroid specification.

FIG. 4d. BMP signaling blockade abrogates thyroid bud formation in mouse: whole foreguts from E8.5 embryos (6-8 somites) were cultured for 2-3 days in the presence of either DMSO (vehicle control) or the BMP antagonist DMH-1. As evidenced by co-localization of Nkx2-1 and Pax8, a discrete thyroid bud formed in control cultures. In contrast, no thyroid bud was apparent when BMP signaling was inhibited (left panel). A substantial reduction in pSmad1/5 content demonstrates the efficacy of DMH-1 in blocking BMP signaling (right panel).

FIG. 5b. Effect of extended time in maturation culture on thyroid marker gene expression comparing D26 vs D30. mRNA expression of the indicated markers by real time RT-PCR. Bars indicate average fold change in gene expression over D0 ESCs±SD (cultured cells n=3, post-natal mouse thyroid tissue n=1). Student's t-test **p≤0.01.

FIGS. 5c-5d show the quantification of the mRNA expression of the indicated markers by real time RT-PCR. 3D versus 2D culture conditions results in significantly higher thyroid gene expression (FIG. 5c), maintained epithelial gene expression and decreased mesenchymal markers (FIG. 5d). Bars indicate average fold change in gene expression over ESCs±SD (n=3 biological replicates). Student's t-test *p≤0.05, p≤0.01, *p≤0.001.

FIGS. 5e-5g show the histology on day 30 of outgrowth and differentiation of Nkx2-1mCherry+ cells sorted on D12 as: H&E stained paraffin sections (FIG. 5e), Immunofluorescence microscopy of D30 ESC-derived follicular-like structures after immunostaining for Nkx2-1 and Tg (FIG. 5f), Nkx2-1 and Pax8 (FIG. 5g). Nuclei are counterstained with DAPI (FIGS. 5f-5g). Scale bars 100 μm (FIG. 5e) and 10 μm (FIGS. 5f and 5g).

FIG. 6b. Recovery of circulating total plasma T4 (top panels) and TSH (lower panels) 8 weeks after transplantation of thyroid follicular-like cells derived from ESCs (D30-ESCs) compared to transplantation of undifferentiated (D0) ESCs. Data indicate each individual mouse plasma level (dots, squares, and triangles) as well as mean r SEM for each group. 1-way ANOVA *p≤0.05, p≤0.01, **p≤0.0001. Statistically significant differences between D30 cells recipient-group and controls after surgery are indicated.

FIG. 6c. 8 weeks after D30-ESCs transplantation: MRI shows a mass (red arrow) on the left kidney (left panel), SPECT co-registered with MRI shows overlay of the hot spot with the mass on the MRI (red arrow: right panel).

FIG. 6d. Tc99M SPECT/CT shows signal of the native thyroid gland (green arrow) in a positive control mouse (bottom panel) and a hot spot (red arrow) on the left kidney in a D30-ESCs recipient (top panel) 8 weeks after surgery but no signal of the native thyroid tissue in the ablated mouse (top panel). Tc99M uptake in bladder (*), stomach (**), and submandibular gland (black triangle).

FIGS. 6e-6g show the histological analysis of kidney tissue sections 8 weeks after transplantation of D30-ESCs under the kidney capsule.

FIG. 6e. H&E staining shows transplanted cells between the host kidney and kidney capsule organized in follicular like structures (first panel) expressing nuclear Nkx2-1 protein by immunohistochemistry (second panel), nuclear Pax8 (third panel), and mCherry (forth panel).

FIGS. 6f-6g. Immunoflouresence microscopy after immunostaining for co-expression of Nkx2-1 and Tg (FIG. 6f), or Nkx2-1 and thyroid hormone T4 (FIG. 6g). Nuclei are counterstained with DAPI (FIGS. 6f and 6g). Scale bars 100 μm (FIG. 6e) and 10 μm (FIGS. 6f and 6g).

FIG. 7a. The quantification of the mRNA expression of the indicated markers by real time RT-PCR at several time points of the differentiation of the Nkx2-1GFP ESC line, comparing different specification medias (Day 6 to Day 14) as indicated in the table. Bars indicate average fold change $[2^{(-\Delta\Delta CT)}]$ in gene expression over ESCs±SD (n=3 biological triplicates). Each time and sort group is identical to that indicated in FIG. 1e. Only statistically significant differences on Day 26 DCI+K between different conditions are indicated.

FIG. 7b. Intracellular staining and FACS analysis of Nkx2-1 protein expression vs expression of the GFP reporter on Day 14 of differentiation, comparing Nkx2-1GFP line versus parental line W4/129S6.

FIG. 7c. mRNA expression of the indicated markers by real time RT-PCR on unsorted cells at Day 26 of the differentiation, comparing the Nkx2-1GFP line with the parental W4/129S6 line. Bars indicate average fold change in gene expression over ESCs±SD (n=3 biological replicates). 2-way ANOVA *p≤0.05, p≤0.01, *p≤0.001, ****p≤0.0001. Only statistically significant differences in the Day 26 DCI+K condition are shown.

FIG. 8a. Dissection of a Pax8cre Rosa26-lox-Stop-lox-tdTomato mouse pup showing expression of Pax8tdTomato trace in the indicated organs.

FIG. 8b. Representative iPSC colonies generated for FIG. 2. Bright field image capture, Alkaline Phosphatase staining, SSEA-1 immunofluorescence microscopy, and DAPI nuclear staining are shown.

FIG. 8c. Representative images of Day 25 cells produced by outgrowth of cells sorted on Day 14 using the gates indicated in main FIG. 2d.

FIGS. 10a-10b show the role of BMP and FGF signaling in *Xenopus* thyroid specification.

FIG. 10a. Analysis of phosphorylated ERK1/2 and phosphorylated SMAD1/5/8 during *Xenopus* thyroid development: (A-B') Confocal immunofluorescence analysis on sagittal sections of stage NF20 *Xenopus* embryos showing positive phospho-ERK1/2 and phospho-SMAD1/5/8 signals in the ventral anterior foregut endoderm and mesoderm (anterior left). (C-E") Confocal immunofluorescence analysis at stage NF33/34 on transverse sections through the ventral pharyngeal region show (C-C") that the nascent Nkx2-1+ thyroid primordium budding from the Sox2+ pharyngeal floor stains positive for phospho-SMAD1/5/8 (D-D") and phosphor-ERK1/2 (E-E"). Scale bars: 50 μm FIG. 10b. BMP and FGF, but not RA or Wnt/β-catenin, signals during stage NF13-20 are necessary for induction of thyroid nkx2-1 in *Xenopus*: Whole embryos were cultured in the indicated pathway antagonists from either stage NF13 to NF20 or from stage NF20 to NF35 and assayed by mRNA in-situ hybridization for expression of nkx2-1 at stage NF35. The number of embryos with the displayed phenotype is indicated.

FIGS. 11a-11d show the maturation of thyroid follicular cells in vitro.

FIG. 11a. mRNA expression of the indicated markers by real time RT-PCR at Day 22 and Day 25. Bars indicate average fold change in gene expression over ESCs±SD (n=3 biological replicates). Student's t-test *p~0.05, p~0.01, *p~0.001

FIG. 11b. Schematic of extended culture protocol up to day 30 of differentiation. ESCs were sorted on Day 12 and a pure Nkx2-1mCherry+ population was re-plated in 3D culture conditions and kept in culture up to at least Day 30 of differentiation.

FIG. 11c. Composition of media used from D22 to D26 is summarized (right table). cAMP, TSH and Dexamethasone increase thyroid specific gene expression. The quantification of the mRNA expression of the indicated markers by real time RT-PCR at Day 26. Bars indicate average fold change in gene expression over ESCs±SD (n=3 biological replicates). 1-way ANOVA *p~0.05, p~0.01, *p~0.001.

FIG. 11d. Effect of extended time in maturation culture on thyroid marker gene expression, comparing Day 30 versus Day 52. The quantification of the mRNA expression of the indicated markers by real time RT-PCR at Day 30 and Day 50 and mouse thyroid tissue. Bars indicate average fold change in gene expression over D0 ESCs±SD (cultured cells n=3, post-natal mouse thyroid tissue n=1). Student's t-test *p≤0.05.

FIGS. 12a-12g show the rescue of hypothyroid mice after transplantation of putative ESC-derived thyroid organoids (D30-ESCs).

FIGS. 12a-12c show the kinetics of plasma total T4 (FIG. 12a), TSH (FIG. 12b), and total T3 levels (FIG. 12c) indicates a continuous increase of circulating total T4 and T3 and decrease of TSH beginning 2 weeks after surgery. Data indicate each individual mouse plasma level (dots, squares, and triangles) as well as mean±SEM for each group. 1-way ANOVA *p≤0.05, p≤0.01, **p≤0.0001. Statistically significant differences between D30 cells recipient-group and controls after surgery are indicated.

FIG. 12d. Circulating plasma TSH plotted versus T4 for individual recipients 8 weeks after surgery shows inverse correlation of TSH and total T4 levels in each mouse.

FIG. 12e. TSH response test shows comparable increase of total T4 after injection of exogenous TSH in recipients of D30-ESCs compared with positive control mice 10 weeks after surgery in an additional cohort to that shown in a-d. Sham transplanted recipients served as negative controls. 1-way ANOVA *p≤0.001, **p≤0.0001.

FIG. 12f. Histology of D0-ESCs recipient 8 weeks after transplantation. H&E staining (left panel) of a tissue section from the left kidney shows a large teratoma comprised of different cell morphologies, characteristic of lineages derived from three germ layers. MRI co-registered with SPECT (right panel) shows a large mass (red arrow) in the left kidney region corresponding with the tumor shown in the left panel. Stomach (**), scale bar 100 μm (left panel).

FIG. 12g. Volumetric analysis of native thyroid tissue (yellow arrow) of a positive control mouse compared to a recipient of D30-ESCs (bottom panel). Native thyroid tissue in the positive control has a volume of 28.08 mm$^3$ and mean Tc99M uptake of 2.46E-05 MBq/mm$^3$. Transplanted D30-ESCs 8 weeks after surgery reached a volume of 18.92 mm$^3$ and a mean Tc99M uptake of 2.62E-05 (red arrow, top panel).

DETAILED DESCRIPTION

Figure 1A:
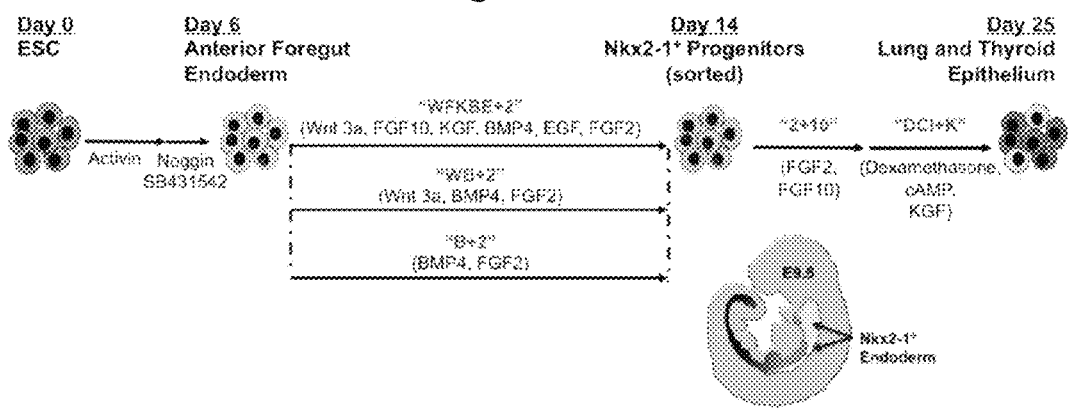
FIGS. 1a-1e show that exogenous BMP4 and FGF2 are sufficient to specify Nkx2-1+ thyroid progenitors from ESC-derived endoderm.

Unless otherwise explained, all technical and scientific terms used herein have the same meaning as commonly understood by one of ordinary skill in the art to which this disclosure belongs. It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Definitions of common terms in biology can be found in The Merck Manual of Diagnosis and Therapy, 19th Edition, published by Merck Sharp & Dohme Corp., 2011 (ISBN 978-0-911910-19-3) or the 2015 digital online edition at merckmanuals.com; Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); and similar reference books, the contents of which are all incorporated by reference herein in their entireties. Further, unless otherwise required by context, singular terms shall include pluralities and plural terms shall include the singular.

Unless otherwise stated, the disclosed embodiments were performed using standard procedures known to one skilled in the art, for example, in Current Protocols in Molecular Biology (CPMB) (Fred M. Ausubel, et al. ed., John Wiley and Sons, Inc.), Current Protocols in Stem Cell Biology, electronic version at onlinelibrary.wiley.com/book/10.1002/9780470151808 (Editor: Hoboken, N.J., John Wiley & Sons, Inc. 2007), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, and Methods in Molecular Biology, Vo. 203, 2003, which are all herein incorporated by reference in their entireties.

It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

The present disclosure relates to in vitro methods of making thyroid cells that secrete thyroid hormone and also are responsive to thyroid stimulating hormone (TSH) from pluripotent stem cells (PSCs) where the methods do not involved the over-expression of NKX2.1 and PAX8 in the PSCs. The present disclosure also relates to and the uses of these thyroid hormone secreting-cells for therapeutic and laboratory research purposes.

The inventors have found a simple way to prepare cells that behave functionally like true thyroid cells by incubation or contacting PSCs in culture with exogenous factors, bone morphogenetic protein BMP4, fibroblast growth factor FGF2, TSH and dexamethasome. The resultant cells behave like true thyroid cells because they would metabolize iodine, make thyroid hormones and release the thyroid hormones in response to the presence of TSH. The inventors have found that a combinatorial BMP and FGF signaling pathways is necessary for the production of PSC-derived mature thyroid cells that would secrete thyroid hormones and would be responsive to the TSH.

This method is unlike that currently known in the art. Thyroid cells have been induced and differentiated from PSCs after exogenous transcription factors were over-expressed in the PSCs. PSCs have been induced into thyroid lineage by providing a cocktail of exogenous growth factors but these cells fail to complete full differentiation into thyroid cells. Early thyroid progenitor/lineage cells derived for PSCs fail to mature into functional thyroid epithelial cells. Functional thyroid epithelial cells metabolizes iodine, secretes thyroid hormone, express enzymes necessary for thyroid hormone and iodide metabolism, and respond to the presence of TSH. Therefore, it has not been possible previously to generate functional thyroid epithelial cells from pluripotent stem cells (PSCs) via directed differentiation. That is, without the over expression of the transcription factors, NKX2.1 and PAX8, via exogenous coding sequences of NKX2.1 and PAX8.

In the body of an organism, the hypothalamic-pituitary-thyroid axis (HPT axis or thyroid homeostasis or thyrotropic feedback control) is part of the neuroendocrine system responsible for the regulation of metabolism. The HPT depends upon the hypothalamus, the pituitary gland, and the thyroid gland. The hypothalamus senses low circulating levels of thyroid hormone (Triiodothyronine (T3) and Thyroxine (T4)) and responds by releasing thyrotropin-releasing hormone (TRH). The TRH stimulates the pituitary to produce thyroid-stimulating hormone (TSH). The TSH, in turn, stimulates the thyroid to produce thyroid hormone until levels in the blood return to normal. Thyroid hormone exerts negative feedback control over the hypothalamus as well as anterior pituitary, thus controlling the release of both TRH from hypothalamus and TSH from anterior pituitary gland.

In the prior work by others, the failure of continued differentiation and maturation in the thyroid lineage of PSCs-derived cells could, in part, be due to an incomplete understanding of signals regulating thyroid development. The inventors sought to identify signaling pathways that regulate early thyroid development in order to accomplish the directed differentiation of PSCs into mature, functional thyroid follicular cells. The inventors identified that the combinatorial bone morphogenetic protein (BMP) and fibroblast growth factor (FGF) signaling as necessary for induction of thyroid fate in developing anterior foregut endoderm in multiple species from amphibians to mammals, and they utilize these pathways to induce thyroid fate sequentially from multipotent PSC-derived endodermal precursors via the technique of directed differentiation. In this present discovery, PSCs, when cultured in serum-free medium containing BMP4 and FGF2, enter and differentiate into the thyroid lineage. Once the thyroid lineage is determined, TSH and dexamethasone then direct the maturation of the PSC-derived thyroid progenitor/lineage cells into mature thyroid hormone secreting and TSH-responsive cells. Moreover, during maturation in 3D culture the resulting cells form thyroid follicular organoids with an organized monolayered epithelium consistent with thyroid follicles, express genes required for iodine metabolism and hormone biosynthesis, and can function in vivo following transplantation into hypothyroid mice, that is, produce and secrete thyroid hormone, and response to TSH.

Thus the inventors have developed an in vitro system able to reveal the basic developmental mechanisms and gene programs of thyroid cells at early stages of embryonic development that are otherwise hard to access in vivo, and they have produced an inexhaustible source of sortable cells with structural and functional thyroid follicular capacity.

Accordingly, in one embodiment, provided herein is an ex vivo or in vitro method for producing a cell that produces and secretes thyroid hormone, and responses to TSH. Such a cell can be derived from a PSC, or an endodermal cell, or a thyroid progenitor cell. Such a cell produces and secretes thyroid hormone, and responses to TSH behaves like a thyroid follicular epithelial cell, and therefore is a functional thyroid follicular epithelial cell. In one embodiment, the cell is a PSC-derived thyroid follicular epithelial cell. A PSC is induced to differentiate and develop into an endodermal cell, preferably, a definitive endodermal cell, which is further induced into entry to the thyroid lineage and subsequent differentiation along the thyroid lineage to a thyroid progenitor cell. The thyroid progenitor cell is then induced to mature to a cell that produces and secretes thyroid hormone, and responses to TSH.

Accordingly, in one embodiment, provided herein is an ex vivo or in vitro method for producing a functional thyroid follicular epithelial cell from a thyroid progenitor cell. The ex vivo or in vitro method for producing a thyroid follicular epithelial cell comprising (a) culturing a thyroid progenitor cell in a differentiation medium under condition and time sufficient to further differentiate the thyroid progenitor cell along the thyroid lineage, wherein the differentiation medium comprising fibroblast growth factor 2 (basic) (FGF2), wherein the thyroid progenitor cell co-expresses a NK2 homeobox 1 (Nkx2-1) protein and a paired box 8 (Pax8) protein, and wherein the co-expression of Nkx2.1 and Pax8 are the products of endogenous genes within the cell, and the Nkx2.1 and Pax8 co-expressing thyroid progenitor cell does not comprise exogenously delivered nucleic acid sequences encoding for the co-expression of Nkx2.1 and Pax8 in the cell; and (b) then culturing the thyroid progenitor cell of step (a) in a maturation medium comprising dexamethasone and cAMP, dexamethasone and thyroid stimulating hormone (TSH), or TSH under condition and time sufficient to produce a Nkx2-1+/Pax8+ co-expressing cell that also expresses early and mature thyroid markers: thyroglobulin (Tg+), thyroid stimulating hormone receptor (Tsh+), sodium iodine symporter (Nis+), and thyroid peroxidase (Tpo+).

Accordingly, in another embodiment, the disclosure provides an ex vivo or in vitro method for producing a functional thyroid follicular epithelial cell from an endodermal cell. The ex vivo or in vitro method for producing a thyroid follicular epithelial cell comprising (a) culturing an endodermal cell in a thyroid lineage culture medium under condition and time sufficient to differentiate the endodermal cell into the thyroid lineage without exogenously delivered nucleic acid sequences resulting in the forced over-expression of a NK2 homeobox 1 (Nkx2-1) protein and a paired box 8 (Pax8) protein in the endodermal cell, thereby producing a thyroid progenitor cell, wherein the differentiation culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF), thereby producing Nkx2-1 and Pax8 (Nkx2-1+/Pax8+) co-expressing thyroid progenitor cell therefrom, but not a Nkx2-1 expressing or a Pax8 expressing cell, (b) culturing a thyroid progenitor cell in a differentiation medium under condition and time sufficient to further differentiate the thyroid progenitor cell along the thyroid lineage, the differentiation medium comprising fibroblast growth factor 2 (basic) (FGF2); and (c) then culturing the thyroid progenitor cell of step (b) in a thyroid maturation medium comprising dexamethasone and cAMP, dexamethasone and thyroid stimulating hormone (TSH), or TSH under condition and time sufficient to produce a Nkx2-1+/Pax8+ co-expressing cell that also express early and mature thyroid markers: thyroglobulin (Tg+), thyroid stimulating hormone receptor (Tsh+), sodium iodine symporter (Nis+), and thyroid peroxidase (Tpo+).

Accordingly, in another embodiment, the disclosure provides an ex vivo or in vitro method for producing a function thyroid follicular epithelial cell from a pluripotent stem cell (PSC). The ex vivo or in vitro method for producing a thyroid follicular epithelial cell from a PSC cell comprising (a) culturing a pluripotent stem cells (PSC) in a culture medium under conditions sufficient to initiate entry and formation into an endodermal cell; (b) culturing the endodermal cell in a thyroid lineage culture medium under condition and time sufficient to differentiate the endodermal cell into the thyroid lineage without exogenously delivered nucleic acid sequences resulting in the forced over-expression of a NK2 homeobox 1 (Nkx2-1) protein and a paired box 8 (Pax8) protein in the endodermal cell, thereby producing a thyroid progenitor cell, wherein the differentiation culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF), thereby producing Nkx2-1 and Pax8 (Nkx2-1+/Pax8+) co-expressing thyroid progenitor cell therefrom, but not a Nkx2-1 expressing or a Pax8 expressing cell; (c) culturing the thyroid progenitor cell with a differentiation medium under condition and time sufficient to further differentiate the thyroid progenitor cell along the thyroid lineage, the differentiation medium comprising fibroblast growth factor 2 (basic) (FGF2); and (d) culturing the thyroid progenitor cell of step (c) with a thyroid maturation medium comprising dexamethasone and cAMP, dexamethasone and thyroid stimulating hormone (TSH), or TSH, under condition and time sufficient to produce a Nkx2-1+/Pax8+ co-expressing cell that also expresses early and mature thyroid markers: thyroglobulin (Tg+), thyroid stimulating hormone receptor (Tsh+), sodium iodine symporter (Nis+), and thyroid peroxidase (Tpo+).

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

In one embodiment of the disclosed method, the PSCs, endodermal cells or thyroid progenitor cells are not transfected with exogenous copies of nucleic acid sequences encoding for the transcription factors Nkx2-1 and Pax8.

In one embodiment of the disclosed method, the thyroid progenitor cell is prepared by contacting an endodermal cell with a thyroid lineage culture medium to differentiate the endodermal cell into the thyroid lineage without exogenously delivered nucleic acid sequences resulting in the forced over-expression of the Nkx2-1 protein and the Pax8 protein in the endodermal cell, thereby producing a Nkx2.1+ and Pax8+ thyroid progenitor cell, and wherein the thyroid lineage culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF).

In one embodiment of any disclosed methods, the thyroid maturation medium comprises at least a fibroblast growth factor.

In one embodiment of any disclosed methods, the fibroblast growth factor in the thyroid maturation medium is FGF2 or FGF10.

In one embodiment of any disclosed methods, the thyroid progenitor cell does not comprise an exogenously nucleic acid coding for the transcription factor, NK2 homeobox 1 (Nkx2-1).

In one embodiment of any disclosed methods, the thyroid progenitor cell does not comprise an exogenously nucleic acid coding for the transcription factor, paired box 8 protein (Pax8).

In one embodiment of any disclosed methods, the thyroid progenitor cell does not comprise exogenously nucleic acids coding for the transcription factors, Nkx2-1 and Pax8.

In one embodiment of any disclosed method, the endodermal cell is an anterior/foregut endodermal cell.

In one embodiment of any disclosed methods, the endodermal cell does not comprise an exogenously nucleic acid coding for the transcription factor, NK2 homeobox 1 (Nkx2-1).

In one embodiment of any disclosed methods, the endodermal cell does not comprise an exogenously nucleic acid coding for the transcription factor, paired box 8 protein (Pax8).

In one embodiment of any disclosed methods, the endodermal cell does not comprise exogenously nucleic acids coding for the transcription factors, Nkx2-1 and Pax8.

In one embodiment of any disclosed methods, the differentiation medium for the thyroid progenitor cells further comprising fibroblast growth factor 10 (FGF10).

In one embodiment of any disclosed methods, the differentiation medium for the thyroid progenitor cells further comprising BMP4.

In one embodiment of any disclosed methods, the differentiation medium for the thyroid progenitor cells further comprising TSH.

In one embodiment of any disclosed methods, the differentiation medium for the thyroid progenitor cells consists essentially of FGF2.

In one embodiment of any disclosed methods, the PSC has previously been developed into an endodermal lineage cell.

In one embodiment of any disclosed methods, the PSC has previously been developed into an anterior endodermal lineage cell.

In one embodiment of any disclosed methods, the PSC does not have an exogenously nucleic acid coding for the transcription factor, NK2 homeobox 1 (Nkx2-1).

In one embodiment of any disclosed methods, the PSC does not have an exogenously nucleic acid coding for the transcription factor, paired box 8 protein (Pax8).

In one embodiment of any disclosed methods, the PSC does not have exogenously nucleic acids coding for the transcription factors, Nkx2-1 and Pax8.

In one embodiment of any disclosed methods, the PSC is an induced pluripotent stem (iPS) cell or an embryonic stem cell (ESC).

In one embodiment of any disclosed methods, the PSC is an iPS cell or an ESC having at least a diploid gene locus encoding the homeodomain-containing transcription factor, Nkx2-1, whereby a diploid expression of Nkx2-1 is induced by the respective culturing medium described herein.

In one embodiment of any disclosed methods, the PSC is an iPS cell or an ESC having exactly a diploid gene locus encoding Nkx2-1, whereby a diploid expression of Nkx2-1 is induced.

In one embodiment of any disclosed methods, the PSC is an iPS cell or an ESC wherein the cell does not comprise an exogenous copy of a nucleic acid sequence encoding Nkx2-1, wherein the exogenous copy has been introduced into the cell.

In one embodiment of any disclosed methods, the PSC is an iPS cell or an ESC having at least a diploid gene locus encoding a transcription factor, Pax8.

In one embodiment of any disclosed methods, the PSC is an iPS cell or an ESC having exactly a diploid gene locus encoding a transcription factor, Pax8.

In one embodiment of any disclosed methods, the PSC is an iPS cell or an ESC wherein the cell does not comprise an exogenous copy of a nucleic acid sequence encoding a transcription factor, Pax8, wherein the exogenous copy has been introduced into the cell.

In one embodiment of any disclosed methods, the iPS cell comprises at least an exogenous copy of a nucleic acid sequence encoding a reprogramming factor selected from the group consisting of genes Oct4 (Pou5f1), Sox2, cMyc, Klf4, Nanog, Lin 28 and Glis1. In some embodiments, combinations of reprogramming factors are used. For example, a combination of three or four reprogramming factors consisting of Oct4, Sox2, cMyc (optional), and Klf4, or a combination of four reprogramming factors consisting of Oct4, Sox2, Nanog, and Lin 28. Methods of producing iPS cell are known in the art, e.g., U.S. Pat. No. 8,058,065, and U.S. Patent Application Nos: 20110223669, 20120214243, 20130059386, and 20130183759, all of which are incorporated herein by reference in their entireties.

Previously, PSC-derived thyroid progenitor or thyroid lineage cells had been produced using a six-growth factor serum free growth medium that include BMP4, FGF2, Wingless-Type MMTV Integration Site Family protein, member 3A (Wnt3A), fibroblast growth factor 10 (FGF10), keratinocyte growth factor (KGF), and epidermal growth factor (EGF). However, these thyroid progenitor/lineage cells fail to continue to mature into thyroid hormone secreting cells.

Here, the inventors found that just the combination of BMP4 and FGF2 is essential for inducing PSC-derived endodermal cell entry into the thyroid lineage to give PSC-derived thyroid progenitor cells. The other growth factors used previously in the six-growth factor serum free growth medium, Wnt3A, FGF10, KGF, and EGF, are not required.

The inventors found that contacting PSC-derived endodermal cells with BMP4/FGF2 produces a thyroid progenitor cell. Plating this progenitor with the presence of a maturation cell medium comprising TSH and dexamethasone results in a thyroid follicular epithelial cell that secretes thyroid hormones, metabolizes iodine and respond to stimulation by TSH.

In one embodiment of any disclosed methods, the differentiation medium, maturation medium, or the thyroid lineage culture used in the cell culture medium described herein does not contain Wnt3A.

In one embodiment of any disclosed methods, the differentiation medium, maturation medium, or the thyroid lineage culture medium used in the cell culture described herein does not contain KGF.

In one embodiment of any disclosed methods, the differentiation medium or maturation medium or the thyroid lineage culture medium used in the cell culture described herein does not contain EGF.

In one embodiment of any disclosed methods, the differentiation medium or the maturation medium or the thyroid lineage culture medium used in the cell culture described herein does not contain Wnt3A, KGF, and EGF.

In one embodiment of any disclosed methods, the differentiation medium or maturation medium or the thyroid lineage culture medium used in the cell culture described herein does not contain FGF10.

In one embodiment of any disclosed methods, the differentiation medium or maturation medium or the thyroid lineage culture medium used in the cell culture described herein does not contain Wnt3A, KGF, FGF10, and EGF.

In one embodiment of any disclosed methods, the Nkx2-1+/Pax8+ expressing cell produced from the thyroid progenitor cells, endodermal cells or PSCs are produced in the absence of any contact with at least one of these growth factors: Wnt3A, FGF10, KGF, and EGF.

In one embodiment of any disclosed methods, the Nkx2-1+/Pax8+ expressing cell produced from the thyroid progenitor cells, endodermal cells or PSCs are produced in the absence of any contact with these growth factors: Wnt3A, KGF, and EGF.

In one embodiment of any disclosed methods, the Nkx2-1+/Pax8+ expressing cell produced from the thyroid progenitor cells, endodermal cells or PSCs are produced in the absence of any contact with these growth factors: Wnt3A, FGF10, KGF, and EGF.

In one embodiment of any disclosed methods, the maturation medium for the thyroid progenitor cell described herein comprises at least two or more of the following compounds: dexamethasone (Dex), cyclic adenosine monophosphate (cAMP), TSH, epidermal growth factor (EGF), FGF2 and FGF10.

In one embodiment of any disclosed methods, the maturation medium for the thyroid progenitor cell described herein comprises Dex and cAMP, Dex and TSH, FGF2 and FGF10, or TSH.

In one embodiment of any disclosed methods, the maturation medium for the thyroid progenitor cell described herein consists essentially of Dex and cAMP; Dex and TSH; FGF2 and FGF10; or TSH.

In one embodiment of any disclosed methods, the maturation medium for the thyroid progenitor cell comprises FGF2, FGF10, Dex and cAMP; FGF2, FGF10, Dex and TSH; FGF2, FGF10, EGF and TSH; or Dex, EGF and TSH.

In one embodiment of any disclosed methods, the maturation medium for the thyroid progenitor cell consists essentially of FGF2, FGF10, Dex and cAMP; FGF2, FGF10, Dex and TSH; FGF2, FGF10, EGF and TSH; or Dex, EGF and TSH.

In one embodiment of any disclosed methods, the maturation medium for the thyroid progenitor cell comprises either TSH or cAMP but not both TSH and cAMP.

In one embodiment of any disclosed methods, the differentiation medium consists essentially of a fibroblast growth factor. For examples, FGF2.

In one embodiment of any disclosed methods, the differentiation medium comprises FGF2. In another embodiment, differentiation medium consists essentially FGF2.

In one embodiment of any disclosed methods, the PSC used has been previously cultured into an endodermal cell prior to culturing in a medium comprising BMP4 and FGF2.

In another embodiment of any disclosed method, the PSC has been previously cultured into an endodermal cell for a period of about 1 to about 5 days prior to culturing in a medium comprising BMP4 and FGF2. In some embodiments, the period for endoderm formation from the PSC can vary from about 2 days, about 2.5 days, about 3 days, about 3.5 days, about 4, days, about 4.5 days and 5 days.

In one embodiment of any disclosed method, the PSC has been previously cultured into an endodermal cell and then to the foregut endoderm prior to culturing in a medium comprising BMP4 and FGF2.

In another embodiment of any disclosed method, the PSC has been previously cultured into an endodermal cell, e.g., for a period of about 1 to about 5 days, and then to the foregut endoderm for a period of another day prior to culturing in a medium comprising BMP4 and FGF2.

In another embodiment of any disclosed method, the PSC has been previously cultured into an endodermal cell for a period of about 1 to about 4 days and to the foregut endoderm for a period of another day prior to culturing in a medium comprising BMP4 and FGF2.

In other embodiment of any disclosed method, the PSC has been previously cultured into an endodermal cell for a period of about 2 to about 4 days and then to the foregut endoderm for a period of another day before induction into thyroid progenitors by culturing in a medium comprising BMP4 and FGF2 for a subsequent about 1 to about 10 days.

Culturing and induction of a PSC into an endodermal cell and further into a foregut endodermal cell can be performed by any method known in the art. For example, by culturing the PSC in a medium comprising activin and Noggin as described in the Example section. Alternatively, methods described in the U.S. Pat. Nos. 7,326,572, 7,772,001, 8,187,878, 8,741,643, 8,785,185, and 8,815,590, and U.S. Patent Publication No: US20140162359, the contents of each are incorporated herein by reference in their entirety. Alternatively, commercial differentiation kits such as "STEMdiff™ Definitive Endoderm Kit" by STEM CELL™ Technologies can be used to induce ex vivo differentiation of PSCs.

Markers characteristics of endodermal lineage are known in the art. For examples, 5T4, GDF-3, HNF-3beta/FoxA2, PDX1/IPF1, SOX7, SOX17 and those described in the Example section and in U.S. Pat. Nos. 7,326,572, 7,772,001, 8,187,878, 8,741,643, 8,785,185, and 8,815,590. The expressions of the markers can be verified by RT-PCR, by Western Blot analysis or by any other methods known in the art.

In one embodiment of any disclosed methods, the endodermal cells are cultured in the described BMP4/FGF2-containing cell culture medium for a period of time to induce the endodermal cells to enter the thyroid lineage. For example, the endodermal cells are cultured in the described BMP4/FGF2-containing cell culture medium for a period of time from about 1 to about 10 days.

In other embodiment of any disclosed method, the endodermal cells are culturing in a medium comprising BMP4 and FGF2 for a period of time from about 1 to about 10 days, about 1 to about 8 days, about 1 to about 6 days, about 1 to about 5 days, about 3 to about 6 days, about 3 to about 8 days, about 5 to about 8 days, about 5 to about 10 days, about 2 to about 5 days, about 2 to about 6 days, about 2 to about 8 days, about 2 to about 10 days, about 4 to about 8 days, about 4 to about 10 days, about 6 to about 10 days, about 6 to about 8 days, about 6 to about 10 days, or about 8 to about 10 days.

In other embodiment of any disclosed methods, the endodermal cells are culturing in a medium comprising BMP4 and FGF2 for a period of time from about 5 days, about 6 days, about 7 days, about 8 days, about 9 days, or about 10 days.

In one embodiment of any disclosed methods, the method further comprises verifying the expression of Nkx2-1 and Pax8 in the resultant cells obtained after culturing in the BMP4/FGF2-containing cell culture medium. Nkx2-1 and Pax8 expression can be determined by any methods known in the art. For example, by RT-PCR, by Western Blot analysis or by the method described in the Example section.

In one embodiment of any disclosed methods, the method further comprises selecting for Nkx2-1 and Pax8 expressing cells in resultant cells obtained after culturing in the BMP4/FGF2-containing cell culture medium. Such cells can be sorted for by any methods known in the art. For example, by FACS.

In one embodiment of any disclosed methods, the method further comprises removing the cells that are not expressing Nkx2-1 and Pax8 in the resultant cells obtained after culturing in the BMP4/FGF2-containing cell culture medium. The product of this removal is Nkx2-1 and Pax8 co-expressing cells.

In one embodiment of any disclosed methods, the method further comprises verifying the expression of Tg, Tsh, Nis and Tpo in the resultant cells obtained after culturing in the thyroid maturation medium. Tg, Tsh, Nis and Tpo expressions can be determined by any methods known in the art. For example, by RT-PCR, by Western Blot analysis or by the method described in the Example section.

In one embodiment of any disclosed methods, the Nkx2-1+ and Pax8+ co-expressing thyroid progenitor cells are cultured in the maturation cell culture medium for a period of time, for example, for about 1 to about 20 days. In one embodiment, this step in to obtain Tg, Tsh, Nis and Tpo expressing cells from the resultant cells obtained after culturing in the thyroid maturation medium.

In other embodiments of any disclosed methods, the Nkx2-1+ and Pax8+ co-expressing thyroid progenitor cells are cultured in the maturation cell culture medium for a period of time from about 1 to about 10 days, about 1 to about 12 days, about 1 to about 14 days, about 1 to about 16 days, about 1 to about 18 days, about 1 to about 8 days, about 1 to about 6 days, about 3 to about 6 days, about 3 to about 8 days, about 3 to about 10 days, about 3 to about 12 days, about 3 to about 14 days, about 3 to about 16 days, about 3 to about 18 days, about 3 to about 20 days, about 5 to about 8 days, about 5 to about 10 days, about 5 to about 11 days, about 5 to about 12 days, about 5 to about 14 days, about 5 to about 16 days, about 5 to about 18 days, about 5 to about 20 days, about 4 to about 14 days, about 4 to about 16 days, about 4 to about 18 days, about 4 to about 20 days, about 2 to about 16 days, about 2 to about 18 days, about 2 to about 20 days, about 4 to about 8 days, about 4 to about 10 days, about 4 to about 12 days, about 6 to about 10 days, about 6 to about 12 days, about 6 to about 14 days, about 6 to about 16 days, about 6 to about 18 days, about 6 to about 8 days, about 8 to about 10 days, about 8 to about 12 days, about 8 to about 14 days, about 8 to about 16 days, about 8 to about 18 days, about 8 to about 20 days, about 10 to about 12 days, about 10 to about 14 days, about 10 to about 16 days, about 10 to about 18 days, about 10 to about 20 days, about 12 to about 14 days, about 12 to about 16 days, about 12 to about 18 days, about 12 to about 20 days, about 14 to about 16 days, about 14 to about 18 days, about 14 to about 20 days, about 16 to about 18 days, about 16 to about 20 days, about 18 to about 20 days, about 4 to about 15 days, about 5 to about 20 days, about 8 to about 15 days, about 14 to about 19 days, about 14 to about 17 days, and about 16 to about 19 days.

In other embodiment of any disclosed methods, the Nkx2-1+ and Pax8+ co-expressing thyroid progenitor cells are cultured in the maturation cell culture medium for a period of time from about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, or about 20 days.

In one embodiment of any disclosed methods, the Nkx2-1+ and Pax8+ co-expressing thyroid progenitor cells are cultured in the maturation cell culture medium for a period of time to induce sustained differentiation and maturation in the thyroid lineage to produce functional thyroid epithelial cells. For example, the Nkx2-1+/Pax8+ co-expressing thyroid progenitor cells are cultured in a maturation cell culture medium containing TSH/dexamethasone for a period of time from about 1 to about 20 days.

In one embodiment of any disclosed methods, the resultant Nkx2-1+/Pax8+/Tg+/Tsh+/Nis+/Tpo+ cells do not express differentiated lung markers. For example, surfactant, pulmonary-associated protein C (Sftpc) and secretoglobin family 1A member 1 (Scgb1a1).

In one embodiment of any disclosed methods, the resultant Nkx2-1+/Pax8+/Tg+/Tsh+/Nis+/Tpo+ cells do not express Sftpc and Scgb1a1.

In one embodiment of any disclosed methods, the resultant Nkx2-1+/Pax8+/Tg+/Tsh+/Nis+/Tpo+ cells also express epithelial markers E-Cadhedrin (E-Cad) and epithelial cell adhesion molecule (EpCam).

In one embodiment of any disclosed methods, the resultant Nkx2-1+/Pax8+/Tg+/Tsh+/Nis+/Tpo+ cells also express Forkhead Box E1 protein (Foxe1) and thyroidally-expressed homeobox protein (Hhex).

In one embodiment of any disclosed methods, the method further comprising selecting for Nkx2-1+/Pax8+ expressing cells obtained and removing Nkx2-1+/Pax8−, Nkx2-1−/Pax8−, and Nkx2-1−/Pax8+ expressing cells.

In one embodiment of any disclosed methods, the method further comprising determining diploid expression of Nkx2-1 in the resultant cells.

In one embodiment of any disclosed methods, the method further comprising selecting for Nkx2-1+/Pax8+/Tg+/Tsh+/Nis+/Tpo+/expressing cells obtained.

In one embodiment of any disclosed methods, the method further comprising selecting for Foxe1+/Hhex+ expressing cells obtained.

In one embodiment of any disclosed methods, the method further comprising selecting for E-Cad+/EpCam+ expressing cells obtained.

In one embodiment of any disclosed methods, the method further comprising selecting for the cells obtained wherein the cells do not express Sftpc and/or Scgb1a1 markers. That is, negative selection for Sftpc and/or Scgb1a1 markers on the resultant cells obtained after culturing in the thyroid maturation medium.

In one embodiment of any disclosed methods, the Nkx2-1+/Pax8+ co-expressing thyroid progenitor cells are cultured in a 3D matrix support or on scaffold material or embedded in scaffold material.

In one embodiment of any disclosed methods, the Nkx2-1+/Pax8+ co-expressing thyroid progenitor cells are cultured in a 2D on a culture dish, with or without a feeder cell layer.

In one embodiment of any disclosed methods, the 3D matrix support or scaffold material gives sufficient support to the maturing thyroid cells in culture to organize themselves into 3D thyroid follicular organoid structures.

In one embodiment of any disclosed method, the 3D matrix support/scaffold material comprises extracellular matrix or a biocompatible scaffold. Examples of extracellular matrix or biocompatible scaffold include but are not limited to polymer scaffolds made of biocompatible materials known in the art such as polyester based absorbable, hyaluronic acid, fibrin, silk, collagen, polyethylene glycol (PEG), HYLAFORM® and CAPTIQUE™, RESTYLANE™, RADIESSE™ (hydroxylapatite), SCULPTRA™, poly-L-Lactic Acid (PLLA), PURAMATRIX™, photo-crosslinkable gelatin methacrylate hydrogels, polymethylmethacrylate beads (PMMA microspheres) and chemically modified alginate. Other matrix or scaffold materials include decellularized tissues such as skin and adiposed tissue. For examples, acellular dermal matrices in the market: Allo-Derm® (LifeCell Corp.), AlloMax™ Surgical Graft (Bard Davol), FlexHD® (Ethicon), DermACELL™ (LifeNet Health), DermaMatrix™ (Synthes), DermaPure™, Graftjacket® Regenerative Tissue Matrix, PriMatrix™ (TEI Biosciences), SurgiMend® PRS (TEI Biosciences), Strattice™ Reconstructive Tissue Matrix (LifeCell Corp.), and Permacol™ (Covidien).

One skilled in the art would be able to select a suitable 3D matrix support/scaffold material which can support to the maturation of the disclosed thyroid cells in culture and the organization of matured thyroid cells into 3D organoid structures.

In one embodiment of any disclosed method, the 3D matrix support material is matrigel or cross-linked collagen.

Support or scaffold material can also be constructed from natural materials: in particular different derivatives of the extracellular matrix have been studied to evaluate their ability to support cell growth. Protein based materials, such as collagen or fibrin, and polysaccharidic materials, like chitosan or glycosaminoglycans (GAGs), have all proved suitable in terms of cell compatibility. Among GAGs hyaluronic acid, possibly in combination with cross linking agents (e.g., glutaraldehyde, water soluble carbodiimide, etc.), is one of the possible choices as scaffold material. Functionalized groups of scaffolds may be useful in the delivery of small molecules (drugs) to specific tissues.

A variety of scaffolds and uses thereof are described in U.S. Pat. Nos. 6,103,255, 6,224,893, 6,228,117, 6,328,990, 6,376,742, 6,432,435, 6,514,515, 6,525,145, 6,541,023, 6,562,374, 6,656,489, 6,689,166, 6,696,575, 6,737,072, 6,902,932 and WO/2005/110050, they are hereby incorporated by reference in their entirety.

As an exemplary in practicing the method described for making thyroid-like cells from PSCs, in one embodiment, the somatic cells or ESCs are isolated from a donor subject. The somatic cells are ex vivo induced in culture into pluripotent stem cells (iPSCs), and then induced to differentiate into endodermal cells, also known as definitive endodermal cells. These endodermal cells are further differentiated to the foregut endodermal cells, after which, they are contacted ex vivo with BMP4 and FGF2, followed by TSH and Dex to produce functional PSC-derived thyroid follicular epithelial cells. The endodermal cells, contacted ex vivo with BMP4 and FGF2, produce thyroid progenitor cells. Followed cell culturing with TSH and Dex, the thyroid progenitor cells produce functional PSC-derived thyroid follicular epithelial cells. The BMP4/FGF2 thyroid progenitor cells cells can be tested for the expression of Nkx2-1/Pax8 co-expression. The BMP4/FGF2 thyroid progenitor cells can also further be selected for the expression of Nkx2-1/Pax8 co-expression. Any BMP4/FGF2 cultured cells that do not express both Nkx2-1 and Pax8 are removed and discarded. In other embodiments, The BMP4/FGF2/TSH/dexamethasome cultured cells can be tested for the expression of Nkx2-1/Pax8/Tg/Tsh/Nis/Tpo. Any BMP4/FGF2TSH/dexamethasome cultured cells that do not express all of Nkx2-1, Pax8, Tg, Tsh, Nis, and Tpo are removed and discarded.

The PSC-derived thyroid follicular epithelial cells are Nkx2-1+/Pax8+/Tg+/Tsh+/Nis+/Tpo+co-expressing cells. These cells are additionally Foxe1+/Hhex+/E-Cad+/EpCam+co-expressing cells. These PSC-derived thyroid follicular epithelial cells may be further cultured to expand the cell population (optional), harvested and transplanted (implantation) back into the same donor subject. Here, the donor subject is also the host/recipient subject. Here is an autologous cell transplant in the subject. When the donor subject is different from the recipient subject, there is an non-autologous, allogenic cell transplant in the subject.

In one embodiment, these PSC-derived thyroid follicular epithelial cells are tested for their ability to organize in tissue culture conditions into 3D structures. For example, after the cells are trypsinized and harvested, they are cultured with in a matrix/scaffold material. Cells that exhibit this characteristic is then harvested for therapeutic and research uses. These cells can be used for implantation into a subject, for example, under the skin, in the neck in the location of the thyroid gland, in muscle tissue, or beneath the kidney capsule.

In one embodiment, these PSC-derived thyroid follicular epithelial cells are admixed with acellular matrices derived from adiposed tissues of a recipient subject to test for the cells' ability to organize in tissue culture conditions into 3D thyroid follicular organoid structures. The 3D tissue construct with the 3D thyroid follicular organoid structures therein can be implanted into the recipient subject.

In one embodiment, provided herein is a population of thyroid follicular epithelial cells produced by any of the methods described herein. The thyroid follicular epithelial cells are PSC-derived thyroid follicular epithelial cells induced by the method described herein. That is, the PSC-derived thyroid follicular epithelial cells were induced by culturing PSC-derived endodermal cells in a differentiation medium comprising BMP4 and FGF2, followed by culturing the cells in a maturation medium comprising TSH and dexamethasome. The PSC-derived thyroid follicular epithelial cells are Nkx2-1+/Pax8+/Tg+/Tsh+/Nis+/Tpo+co-expressing cells. These cells are additionally Foxe1+/Hhex+/E-Cad+/EpCam+co-expressing cells.

In one embodiment, provided herein is a population of thyroid follicular epithelial cells produced ex vivo from a population of pluripotent stem cells for use in the treatment of hypothyroidism.

In one embodiment, provided herein is a population of thyroid follicular epithelial cells produced ex vivo from a population of thyroid progenitor cells for use in the treatment of hypothyroidism.

In one embodiment, provided herein is a population of thyroid follicular epithelial cells produced ex vivo from a population of endodermal cells for use in the treatment of hypothyroidism.

In one embodiment, provided herein is a population of thyroid follicular epithelial cells produced ex vivo from a population of pluripotent stem cells for use in the manufacture of medicament in the treatment of hypothyroidism.

A population of thyroid follicular epithelial cells produced ex vivo from a population of thyroid progenitor cells for use in the manufacture of medicament in the treatment of hypothyroidism.

In one embodiment, provided herein is a population of thyroid follicular epithelial cells produced ex vivo from a population of endodermal cells for use in the manufacture of medicament in the treatment of hypothyroidism.

In one embodiment, provided herein is a composition comprising a population of thyroid follicular epithelial cells described herein. The thyroid follicular epithelial cells are PSC-derived thyroid follicular epithelial cells induced by the method described herein. That is, the PSC-derived thyroid follicular epithelial cells were induced by contacting or culturing PSC-derived endodermal cells in a differentiation medium comprising BMP4 and FGF2 to form thyroid progenitor cells, followed by further culturing the resultant thyroid progenitor cells in a maturation medium comprising dexamethasone and cAMP, dexamethasone and thyroid stimulating hormone (TSH), FGF2 and FGF10, or TSH. The PSC-derived thyroid follicular epithelial cells are Nkx2-1+/

Pax8+/Tg+/Tsh+/Nis+/Tpo+co-expressing cells. These cells are additionally Foxe1+/Hhex+/E-Cad+/EpCam+co-expressing cells.

In one embodiment of the population of thyroid follicular epithelial cells or the composition described herein, the population of cells or composition further comprises a pharmaceutically acceptable carrier. In one embodiment, the pharmaceutically acceptable carrier does not comprise tissue culture medium. In one embodiment, the pharmaceutically acceptable carrier comprises serum or plasma.

In one embodiment of the population of thyroid follicular epithelial cells or the composition described herein, the population of cells or composition further comprises serum or plasma.

In one embodiment of the population of thyroid follicular epithelial cells or the composition described herein, the population of cells or composition further comprises a cryopreservative for cryostorage. For example, DMSO.

Cryoprotective agents and optimal cooling rates can protect against cell injury. Cryoprotective agents which can be used include but are not limited to dimethyl sulfoxide (DMSO) (Lovelock, J. E. and Bishop, M. W. H., 1959, Nature 183:1394-1395; Ashwood-Smith, M. J., 1961, Nature 190:1204-1205), glycerol, polyvinylpyrrolidine (Rinfret, A. P., 1960, Ann. N.Y. Acad. Sci. 85:576), Dextran, trehalose, CryoSoFree (Signa Aldrich Co.) and polyethylene glycol (Sloviter, H. A. and Ravdin, R. G., 1962, Nature 196:548). The preferred cooling rate is 1° to 3° C./minute. After at least two hours, the T-cells have reached a temperature of −80° C. and can be placed directly into liquid nitrogen (−196° C.) for permanent storage such as in a long-term cryogenic storage vessel.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In one embodiment of the population of thyroid follicular epithelial cells or the composition described herein, the population of cells or composition further comprises a matrix or scaffold material, wherein the cells are embedded therein.

In one embodiment, a matrix or scaffold material is a biocompatible material. In one embodiment, a matrix or scaffold material is a decellularized tissue such as adipose tissue.

Two applications of in vitro model systems, deriving from ESCs and iPSCs, are frequently touted: 1) the engineering of cell-based therapies able to durably ameliorate disease or regenerate tissue after a single transplantation treatment, and 2) the production of an inexhaustible supply of purified cells of defined lineage at identifiable developmental stages for basic mechanistic studies. Here the inventors demonstrated the application of ESCs and iPSCs towards both goals as purified Nkx2-1+ endodermal progenitors were generated from PSCs for cell-based therapies as well as for basic developmental studies. The inventors have utilized these cells to produce functional, transplantable thyroid follicular organoids able to produce circulating thyroid hormone in vivo at levels that rescue hypothyroid mouse recipients, and they have produced thyroid precursor cells at an early developmental stage revealing that combinatorial BMP and FGF signaling together are required for thyroid lineage specification from multi-potent definitive endoderm.

While ESC/iPSC model systems frequently have been used to confirm or validate developmental signaling pathways identified in vivo or in explants, the inventors were able to utilize ESCs and iPSCs to discern a novel role for the SMAD-dependent BMP signaling pathway in thyroid development. The present studies support a role for combinatorial BMP and FGF signaling in thyroid lineage specification, and argue against a role for any individual signaling pathway in isolation. The findings are in accordance with previous publications demonstrating a role for FGF signaling in early thyroid development. For example, the inventors' finding of nuclear pERK1/2 protein staining in endodermal Nkx2-1+ thyroid progenitors in *Xenopus* embryos is consistent with prior publications demonstrating active FGF signaling is present in the developing *Xenopus* ventral foregut endoderm beginning from stage NF15 (0 ss) after completion of ventral foregut migration, but prior to detection of endodermal nkx2-1, and continuing through the completion of both thyroid and lung specification (stage NF35; 36 ss), (Shifley et al., 2012). Moreover, a functional role for FGF signaling in inducing thyroid cell fate has been previously demonstrated in mouse endodermal explant studies, where addition of exogenous FGF2 prior to thyroid specification has been reported to induce Nkx2-1 and Tg (Serls et al., 2005). Furthermore, in zebrafish models inhibition of FGF prior to specification leads to absence of a thyroid primordium (Wendl et al., 2007). Additional zebrafish models carrying mutations in hand2, which is upstream of FGF, or mutant ace, which results in deficient FGF8, both result in severe thyroid hypoplasia (Abe et al., 2002; Fagman and Nilsson, 2010; Wendl et al., 2007), and importantly the hand2 mutant thyroid phenotype can be rescued by placing beads soaked with FGF1, 2, or 8 adjacent to developing endoderm. A variety of additional mouse genetic models establish that FGF signaling is required for normal early thyroid development and the adjacent cardiac mesoderm is a likely source of these instructive and permissive signals (Celli et al., 1998; Fagman et al., 2007; Fagman and Nilsson, 2010; Kameda et al., 2009; Lania et al., 2009; Vitelli et al., 2002).

In contrast only two prior studies, featuring Chordin mutant and Twisted mutant mice with perturbed BMP signaling, have reported thyroid hypoplasia, raising the possibility of a role for BMP signaling in thyroid development (Bachiller et al., 2003; Petryk et al., 2004), but these prior reports could not discern whether the thyroid defects were primary effects due to inhibition of lineage specification, reduced later proliferation, or secondary effects due to perturbed development of the cardiac field or other adjacent structures. The inventors here utilized their PSC model system, confirmatory *Xenopus* embryos, and mouse developing foregut endoderm explant models to interrogate the period of thyroid lineage specification from endoderm. The inventors observed that the BMP signal transducers phospho-SMAD1/5/8 are present in the nuclei of endodermal thyroid progenitors at the time of lineage specification, and SMAD-dependent BMP signaling is necessary for induction of the Nkx2-1+ thyroid program. The precise mechanism by which BMP signaling induces thyroid fate warrants further study to determine whether these mechanisms are similar to those found to be active in specification of Nkx2-1+ lung progenitors from endoderm. In the prospective lung primordium of the anterior-ventral foregut, BMP signaling has been proposed to work by directly repressing Sox2 activity via phospho-SMAD binding to the proximal Sox2 promoter, consequently resulting in the induction of lung epithelial cell fate (Domyan et al., 2011). Similarly, in developing *Xenopus* embryos, the inventors found repression of Sox2 within endodermal Nkx2-1+ thyroid progenitors that also expressed nuclear phospho-SMAD1/5/8 proteins around the time of thyroid lineage specification, raising the possibility that this model may also be regulating thyroid cell fate.

Identification of the sequence of developmental signals that promote thyroid development from endoderm allowed the inventors to perform the first known generation of functional thyroid follicular-like epithelial cells by the technique of "directed differentiation" of PSCs. In accordance with prior observations from mouse genetic models (Postiglione et al., 2002), the inventors observed that TSH signaling is dispensable for early thyroid development, including thyroid lineage specification and initial differentiation; however, TSH promoted the maturation of the genetic program necessary for thyroid iodine metabolism. As suggested by observations made in patients with hypothyroidism due to NKX2-1 haploinsufficiency (Krude et al., 2002), the inventors also found thyroid differentiation subsequent to lineage specification to be profoundly sensitive to Nkx2-1 haploinsufficiency in their in vitro mouse model system.

Since the defining feature of thyroid follicular epithelial cells is functional in vivo hormone biosynthesis, their transplantation studies provided an important functional assessment of the thyroid organoids we generated by directed differentiation. After transplantation beneath the kidney capsules of hypothyroid mouse recipients, the inventors found evidence for durable, functional engraftment of the putative organoids which after 8 weeks in vivo: 1. retained recognizable structure; 2. continued to express the molecular phenotype of thyroid follicular epithelia; 3. produced circulating T4 and T3; and 4. were regulated by the hypothalamic-pituitary axis. To prove these grafted organoids derived from Nkx2-1+ endodermal precursors generated through directed differentiation, rather than from non-Nkx2-1 expressing cells, an important aspect of our work involved the sorting to purity of only Nkx2-1mCherry+ endodermal cells prior to transplantation. This sorting algorithm should also help to minimize the chance of teratomas developing in vivo from any residual undifferentiated cells. Indeed, no teratomas were observed arising from the sorted, transplanted cells in any recipient in the studies.

A final outcome of the studies is the production of a novel source of primary-like thyroid progenitors for basic studies. Since thyroid epithelia are difficult to maintain in culture, to our knowledge an expandable source of primary cells for laboratory work has not previously been available. Our sorting strategy to deplete the cells of contaminating mesenchyme and our feeder-free, serum-free culture conditions should provide a valuable source of thyroid lineage cells for basic studies aimed at dissecting the pathways of thyroid hormone biogenesis and the signaling mechanisms involved in thyroid differentiation or oncogenesis.

In one embodiment, provided herein is a method for treating hypothyroidism in a subject in need thereof comprising transplanting an effective amount of a population of thyroid follicular epithelial cells described herein into the subject. The thyroid follicular epithelial cells are PSC-derived thyroid follicular epithelial cells induced by the method described herein. The PSC-derived thyroid follicular epithelial cells are Nkx2-1+/Pax8+/Tg+/Tsh+/Nis+/Tpo+co-expressing cells. These cells are additionally Foxe1+/Hhex+/E-Cad+/EpCam+co-expressing cells. In one embodiment, the cells form 3D thyroid follicular organoid in vivo implantation.

In one embodiment, provided herein is a method for treating hypothyroidism in a subject in need thereof comprising transplanting a composition of thyroid follicular epithelial cells described herein or implanting a 3D construct comprising population of thyroid follicular epithelial cells and a matrix/scaffold material, wherein the thyroid follicular epithelial cells are embedded in the matrix and form 3D thyroid follicular organoid in the matrix. The thyroid follicular epithelial cells are PSC-derived thyroid follicular epithelial cells induced by the method described herein. The PSC-derived thyroid follicular epithelial cells are Nkx2-1+/Pax8+/Tg+/Tsh+/Nis+/Tpo+co-expressing cells. These cells are additionally Foxe1+/Hhex+/E-Cad+/EpCam+co-expressing cells.

In one embodiment, provided herein is a population of thyroid follicular epithelial cells produced ex vivo from a population of pluripotent stem cells for use in the treatment of hypothyroidism. The thyroid follicular epithelial cells are PSC-derived thyroid follicular epithelial cells induced by the method described herein. The PSC-derived thyroid follicular epithelial cells are Nkx2-1+/Pax8+/Tg+/Tsh+/Nis+/Tpo+co-expressing cells. These cells are additionally Foxe1+/Hhex+/E-Cad+/EpCam+co-expressing cells.

In one embodiment, provided herein is a population of thyroid follicular epithelial cells produced ex vivo from a population of pluripotent stem cells for use in the manufacture of medicament in the treatment of hypothyroidism. The thyroid follicular epithelial cells are PSC-derived thyroid follicular epithelial cells induced by the method described herein. The PSC-derived thyroid follicular epithelial cells are Nkx2-1+/Pax8+/Tg+/Tsh+/Nis+/Tpo+co-expressing cells. These cells are additionally Foxe1+/Hhex+/E-Cad+/EpCam+co-expressing cells.

Hypothyroidism means too little thyroid hormone. Hypothyroidism is a condition in which the body lacks sufficient thyroid hormone. Since the main purpose of thyroid hormone is to "run the body's metabolism," it is understandable that people with this condition will have symptoms associated with a slow metabolism. Approximately 10 million Americans have this common medical condition. In fact, as many as 10% of women may have some degree of thyroid hormone deficiency.

Iodine is a constituent of the thyroid hormones, thyroxine (T4) and triiodothyronine (T3). These are made from addition condensation products of the amino acid tyrosine, and are stored prior to release in an iodine-containing protein called thyroglobulin. T4 and T3 contain four and three atoms of iodine per molecule, respectively. The thyroid gland actively absorbs iodine from the blood to make and release these hormones into the blood, actions which are regulated by a second hormone TSH from the pituitary.

There are two fairly common causes of hypothyroidism. The first is a result of previous (or currently ongoing) inflammation of the thyroid gland, which leaves a large percentage of the cells of the thyroid damaged (or dead) and incapable of producing sufficient hormone. The most common cause of thyroid gland failure is called autoimmune thyroiditis (also called Hashimoto's thyroiditis), a form of thyroid inflammation caused by the patient's own immune system.

The second major cause is the broad category of "medical treatments." The treatment of many thyroid conditions warrants surgical removal of a portion or all of the thyroid gland. If the total mass of thyroid producing cells left within the body is not enough to meet the needs of the body, the patient will develop hypothyroidism. Remember, this is often the goal of the surgery for thyroid cancer.

But at other times, the surgery will be to remove a worrisome nodule, leaving half of the thyroid in the neck undisturbed. Sometimes, this remaining thyroid lobe and isthmus will produce enough hormones to meet the demands of the body. For other patients, however, it may become apparent years later that the remaining thyroid just can't quite keep up with demand.

Similarly, goiters and some other thyroid conditions can be treated with radioactive iodine therapy. The aim of the radioactive iodine therapy (for benign conditions) is to kill a portion of the thyroid to prevent goiters from growing larger or producing too much hormone (hyperthyroidism).

Occasionally, the result of radioactive iodine treatment will be that too many cells are damaged so the patient often becomes hypothyroid within a year or two. However, this is usually greatly preferred over the original problem.

Symptoms of hypothyroidism include the following: Fatigue, Weakness, Weight gain or increased difficulty losing weight, coarse, dry hair, dry, rough pale skin, hair loss, cold intolerance compared to those around you, muscle cramps and frequent muscle aches, constipation, depression, irritability, memory loss, abnormal menstrual cycles and decreased libido. Each individual patient may have any number of these symptoms, and they will vary with the severity of the thyroid hormone deficiency and the length of time the body has been deprived of the proper amount of hormone. Most people will have a combination of these symptoms. The skilled physician would be able to diagnose hypothyroidism that is known in the art.

In one embodiment, the disclosed population of thyroid follicular epithelial cells produced by the ex vivo cell culture method described herein functions like the cells of the thyroid gland in a normal, healthy subject. In other words, the disclosed population of thyroid follicular epithelial cells can absorb iodine, metabolize iodine, synthesize and secrete thyroid hormones, and respond to TSH by releasing thyroid hormones.

In one embodiment, the subject is a mammal. In another embodiment, the subject is a primate mammal. In another embodiment, the subject is a human.

In one embodiment of any disclosed population of thyroid follicular epithelial cells described herein, the cells synthesize and secrete thyroid hormones in vitro in culture.

In one embodiment of any disclosed population of thyroid follicular epithelial cells described herein, the cells synthesize and secrete thyroid hormones in vivo. For example, when the cells are implanted into a subject.

In one embodiment of any disclosed population of thyroid follicular epithelial cells described herein, the cells metabolize iodine.

In one embodiment of any disclosed population of thyroid follicular epithelial cells described herein, the thyroid follicular epithelial cells can actively absorbs iodine from the blood to make and release these hormones into the blood in vivo, when the thyroid follicular epithelial cells are transplanted into a subject.

In one embodiment of any disclosed population of thyroid follicular epithelial cells described herein, when the thyroid follicular epithelial cells are transplanted into a subject, the thyroid follicular epithelial cells secrete thyroid hormones in vivo in response to the presence of TSH.

In one embodiment of any disclosed population of thyroid follicular epithelial cells described herein, the cells are Nkx2-1+/Pax8+/Tg+/Tsh+/Nis+/Tpo+co-expressing cells.

In one embodiment of any disclosed population of thyroid follicular epithelial cells described herein, the cells are Foxe1+/Hhex+co-expressing cells.

In one embodiment of any disclosed population of thyroid follicular epithelial cells described herein, the cells are Nkx2-1+/Pax8+/Tg+/Tsh+/Nis+/Tpo+/Foxe1+/Hhex+co-expressing cells In one embodiment of any disclosed population of thyroid follicular epithelial cells described herein, the cells are Nkx2-1+/Pax8+/Tg+/Tsh+/Nis+/Tpo+/E-Cad+/EpCam+co-expressing cells.

In one embodiment of any disclosed population of thyroid follicular epithelial cells described herein, the cells are Foxe1+/Hhex+/E-Cad+/EpCam+co-expressing cells.

In one embodiment of any disclosed population of thyroid follicular epithelial cells described herein, the cells are Nkx2-1+/Pax8+/Tg+/Tsh+/Nis+/Tpo+/Foxe1+/Hhex+/E-Cad+/EpCam+co-expressing cells.

In one embodiment of any disclosed population of thyroid follicular epithelial cells described herein, the cells are Sftpc−/Scgb1a1− expressing cells. That is the thyroid follicular epithelial cells described herein do not express the Sftpc and the Scgb1a1 markers.

In one embodiment of any disclosed population of thyroid follicular epithelial cells described herein, the cells are E-Cad+/EpCam+ and Sftpc−/Scgb1a1− expressing cells.

In one embodiment of any disclosed population of thyroid follicular epithelial cells described herein, the cells are Foxe1+/Hhex+ and Sftpc−/Scgb1a1− expressing cells.

In one embodiment of any disclosed population of thyroid follicular epithelial cells described herein, the cells are Foxe1+/Hhex+/E-Cad+/EpCam+ and Sftpc−/Scgb1a1− expressing cells.

In one embodiment of any disclosed population of thyroid follicular epithelial cells described herein, the cells are Nkx2-1+/Pax8+/Tg+/Tsh+/Nis+/Tpo+ and Sftpc−/Scgb1a1− expressing cells.

In one embodiment of any disclosed population of thyroid follicular epithelial cells described herein, the cells are Nkx2-1+/Pax8+/Tg+/Tsh+/Nis+/Tpo+/E-Cad+/EpCam+ and Sftpc−/Scgb1a1− expressing cells.

In one embodiment of any disclosed population of thyroid follicular epithelial cells described herein, the cells are Nkx2-1+/Pax8+/Tg+/Tsh+/Nis+/Tpo+/Foxe1+/Hhex+ and Sftpc−/Scgb1a1− expressing cells.

In one embodiment of any disclosed population of thyroid follicular epithelial cells described herein, the cells are Nkx2-1+/Pax8+/Tg+/Tsh+/Nis+/Tpo+/E-Cad+/EpCam+/Foxe1+/Hhex+ and Sftpc−/Scgb1a1− expressing cells.

In one embodiment of any disclosed treatment method described herein, the method further comprises selecting a subject diagnosed as having hypothyroidism.

In one embodiment of any disclosed methods described herein, the method further comprises providing a population of PSCs for the ex vivo production of a population of PSC-derived thyroid follicular epithelial cell using the method described herein. That is, provide a population of PSC-derived endodermal cells which would then be cultured ex vivo in the presence of a medium comprising BMP4 and FGF2 to induce the PSC-derived endodermal cells to enter and differentiate in the thyroid lineage, by the induction of the transcription factors Nkx2-1 and Pax8. This is followed by ex vivo culturing the PSC-derived Nkx2-1+/Pax8+ cells in the presence of a medium comprising FGF2 to induce sustained differentiation in the thyroid lineage, followed by culturing in a maturation medium to produce thyroid follicular epithelial cell that metabolizes iodine, secretes thyroid hormone, express enzymes necessary for thyroid hormone and iodide metabolism, and respond to the presence of TSH. The PSCs can come from a subject who is diagnosed with hypothyroidism or from a health donor subject. In one embodiment, the donor subject is at least HLA matched with the potential recipient subject of the PSC-derived thyroid follicular epithelial cells.

In one embodiment of any disclosed methods described herein, the method further comprises harvesting a population of PSCs from a/the subject in order to ex vivo produce a population of PSC-derived thyroid follicular epithelial cell for future transplantation. The population of PSCs is used to produce a population of PSC-derived endodermal cells.

In one embodiment of any disclosed methods described herein, the PSCs are harvested from the bone marrow (BM), adipose tissue (AT), peripheral blood (PB), placenta, amniotic fluid, chorionic villi, peripheral blood, placental blood and umbilical cord blood (UBC).

In one embodiment of any disclosed methods described herein, the PSCs provided is obtained from mobilized peripheral blood from a/the subject.

In one embodiment of any one of the method described, the population of PSCs provided is autologous to the recipient subject of the PSC-derived thyroid follicular epithelial cells.

In one embodiment of any one of the method described, the population of PSCs provided is non-autologous and allogenic to the recipient subject of the PSC-derived thyroid follicular epithelial cells.

In one embodiment of any one of the method described, the population of PSCs provided is non-autologous and xenogeneic to the recipient subject of the PSC-derived thyroid follicular epithelial cells.

In one embodiment of any disclosed treatment method described herein, the PSC-derived thyroid follicular epithelial cells are autologous, xenogeneic or allogenic to the recipient subject of the PSC-derived thyroid follicular epithelial cells.

In one embodiment of any disclosed treatment method herein, the population of PSC-derived thyroid follicular epithelial cells is encapsulated prior to implantation. For example, cells were encapsulated in a biodegradable synthetic extracellular matrix (sECM) and placed in a suitable location in vivo, for example, beneath the skin.

Cell encapsulation or cell microencapsulation technology involves the immobilization of the desired cells within a polymeric semi-permeable membrane that permits the bidirectional diffusion of molecules such as the influx of oxygen, nutrients, growth factors etc. essential for cell metabolism and the outward diffusion of waste products and therapeutic proteins. At the same time, the semi-permeable nature of the membrane prevents immune cells and antibodies from destroying the encapsulated cells regarding them as foreign invaders. The main motive of cell encapsulation technology is to overcome the existing problem of graft rejection in tissue engineering applications and thus reduce the need for long-term use of immunosuppressive drugs after an organ transplant to control side effects.

In one embodiment of any disclosed treatment method described herein, the population of PSC-derived thyroid follicular epithelial cells is encapsulated in a biocompatible polymer or a scaffold material.

In one embodiment of any disclosed treatment method described herein, the biocompatible polymer or a scaffold material forms mechanically and chemically stable semi-permeable matrix.

In one embodiment of any disclosed treatment method described herein, the population of PSC-derived thyroid follicular epithelial cells is encapsulated in a biocompatible polymer or a scaffold material and the cells are cross-linked to the encapsulation polymer to stabilize the capsules.

A variety of biocompatible polymer materials are available and known in the art for cell encapsulation. For examples, alginate, modified alginate having amino acid sequence Arg-Gly-Asp (RGD) for conjugation purposes, alginate-polylysine-alginate (APA), collagen, gelatin, chitosan, agarose and cellulose sulfate to name a few. Hydrogels made with alginate, or collagen, or gelation, or chitosan, or agarose, or cellulose sulfate or combinations of are commonly used. Any method can be used to encapsulate the described population of engineered mammalian cells. For examples, the method described in the Example section, in U.S. Pat. Nos. 4,353,888, 4,409,331, 5,334,640, 5,459,054, and 5,612,207, all of which are incorporated herein by reference in their entireties.

As an exemplary in practicing the treatment method, in one embodiment, the somatic cells are isolated from a subject who is diagnosed with hypothyroidism ie., a host subject, or from a health donor subject. The somatic cells are ex vivo induced in culture into pluripotent stem cells (iPSCs), after which, they are contacted ex vivo with BMP4 and FGF2, followed by TSH and dexamethasome to produce functional PSC-derived thyroid follicular epithelial cells. The PSC-derived thyroid follicular epithelial cells are Nkx2-1+/Pax8+/Tg+/Tsh+/Nis+/Tpo+/expressing cells. These cells are additionally Foxe1+/Hhex+/E-Cad+/EpCam+ expressing cells. These PSC-derived thyroid follicular epithelial cells may be further cultured to expand the cell population (optional), harvested and transplanted (implantation) back into the same host subject diagnosed with hypothyroidism, i.e. an autologous cell transplant. The host subject is both the donor and recipient subject is the same. Alternatively, the thyroid cell population is transplanted (implantation) into the recipient host subject diagnosed with hypothyroidism, wherein the recipient host subject is different from the health donor subject.

In another embodiment, the somatic cells are isolated from a donor who is an HLA-type match with a host (recipient) who is diagnosed with hypothyroidism. Donor-recipient antigen type-matching is well known in the art. The HLA-types include HLA-A, HLA-B, HLA-C, and HLA-D. These represent the minimum number of cell surface antigen matching required for transplantation. That is the transfected cells are transplanted into a different host, i.e., allogeneic to the recipient host subject. The donor's or subject's somatic cells are ex vivo induced in culture into pluripotent stem cells (iPSCs) by any method known in the art, after which, they are differentiated to endodermal cells. The iPSC-derived endodermal cells are then cultured ex vivo in a medium containing BMP4 and FGF2, followed by FGF2, and then followed by TSH and dexamethasome to produce functional iPSC-derived thyroid follicular epithelial cells. The iPSC-derived thyroid follicular epithelial cells are Nkx2-1+/Pax8+/Tg+/Tsh+/Nis+/Tpo+co-expressing cells. These cells are additionally Foxe1+/Hhex+/E-Cad+/EpCam+co-expressing cells. These iPSC-derived thyroid follicular epithelial cells may be further cultured to expand the cell population (optional), harvested and then transplanted (implantation) into the host subject.

As another exemplary in practicing the treatment method, in one embodiment, embryonic stem cells (ESCs) are isolated from a host subject, for example, from a fetus in gestation. For example, from the placenta, amniotic fluid, chorionic villi, placental blood and umbilical cord blood of the newborn. The ESCs are first differentiated in vitro or ex vivo to endodermal cells. The ESC-derived endodermal cells are then contacted ex vivo with a medium containing BMP4 and FGF2, followed by a medium containing FGF2, and then followed by a medium containing TSH and Dex to produce functional ESC-derived thyroid follicular epithelial cells. The ESC-derived thyroid follicular epithelial cells are Nkx2-1+/Pax8+/Tg+/Tsh+/Nis+/Tpo+co-expressing cells. These cells are additionally Foxe1+/Hhex+/E-Cad+/Ep-Cam+co-expressing cells. These ESC-derived thyroid follicular epithelial cells may be further cultured to expand the cell population (optional), harvested and transplanted (implantation) back into the same host, i.e. an autologous cell transplant.

In one embodiment, the ESCs isolated from a host subject are at the minimum HLA antigen type-matched with a recipient subject having hypothyroidism.

In one embodiment, the transplanted cells engrafts in the host subject. In another embodiment, the transplanted cells engrafts in a recipient subject who did not supplied the initial somatic cells or ESCs or PSCs or thyroid progenitor cells or endodermal cells for ex vivo differentiation and maturation to produce functional PSC-derived thyroid follicular epithelial cells.

In some embodiments, the somatic cells isolated from a subject and have been induced in culture into iPSCs can be cryopreserved for storage prior to the ex vivo differentiation and maturation to produce functional PSC-derived thyroid follicular epithelial cells. The iPSCs produced can also be stored, or cryopreserved after cell expansion and stored.

In some embodiments, the ESCs isolated from a subject can be cryopreserved for storage prior to the ex vivo differentiation and maturation to produce functional PSC-derived thyroid follicular epithelial cells. The ESCs can also be stored, or cryopreserved after cell expansion and stored.

Similarly, the thyroid progenitor cells can be cryopreserved for storage prior to the ex vivo differentiation and maturation to produce functional thyroid follicular epithelial cells. The thyroid progenitor cells can also be stored, or cryopreserved after cell expansion and stored.

In some embodiments, the thyroid follicular epithelial cells can also be cryopreserved and stored, or cryopreserved after cell expansion and stored.

In one embodiment of any one of the method described, the population of PSC-derived thyroid follicular epithelial cells used in the treatment of hypothyroidism is at the minimum HLA type matched to the recipient subject.

In one embodiment of any one of method described herein, after the differentiation and maturation into functional thyroid follicular epithelial cells, the resultant PSC-derived thyroid follicular epithelial cells are cryopreserved prior to use, for example, ex vivo expansion and/or implantation into a recipient subject.

In one embodiment of any one of the method described herein, after the differentiation and maturation into functional thyroid follicular epithelial cells, the resultant PSC-derived thyroid follicular epithelial cells are culture expanded ex vivo prior to use, for example, cryopreservation, and/or implantation/engraftment into a recipient subject.

In one embodiment of any disclosed treatment method described herein, the PSC-derived thyroid follicular epithelial cells are cryopreserved prior to transplantation (implantation) into the subject.

In one embodiment, provided herein is a cell culture-based model system comprising PSC-derived thyroid follicular epithelial cells. These cells can organize into a 3D organoid structure. This model system can be used for research purposes. For example, the cells can be used to study basic thyroid hormone biogenesis, the thyroid hormone set point for an individual, the emergence of thyroid cancer from follicular precursors, or the molecular pathways that regulate the self-renewal, maturation, proliferation, response to TSH, or longevity of a thyroid cell. The cells made from the iPS cells of an individual patient can also be used as a "precision medicine" tool to predict the individualized responsiveness of that individual to drugs, or can be used to screen a library of drugs or small molecules to identify new candidate drugs for treating thyroid disease, autoimmune thyroid diseases, hypothyroidism, hyperthyroidism, or thyroid cancers.

In one embodiment, provided herein is a 3D cell construct comprising PSC-derived thyroid follicular epithelial cells and a matrix/scaffold material wherein the cells are embedded in the matrix/scaffold material so that the cells form 3D thyroid follicle organoid structures in the matrix/scaffold material. In one embodiment, the PSC-derived thyroid follicular epithelial cells therein secrete thyroid hormones. In one embodiment, the PSC-derived thyroid follicular epithelial cells therein are stimulated with TSH. In one embodiment, the PSC-derived thyroid follicular epithelial cells therein metabolize iodine. In one embodiment, the PSC-derived thyroid follicular epithelial cells therein express enzymes for the thyroid hormone synthesis.

In one embodiment of any methods described herein, the cells are culture ex vivo in sterile conditions, especially when the intended use of the resultant cells is to implant into a subject.

In one embodiment of any methods described herein, the cells are harvested and collected under sterile conditions for the purpose of subsequent implantation into a subject.

Accordingly, provided herein are therapeutic compositions or pharmaceutical compositions that comprised the described PSC-derived thyroid follicular epithelial cells. Pharmaceutical compositions comprise additionally a pharmaceutically acceptable carrier. The PSC-derived thyroid follicular epithelial cells have an exogenous nucleic acid sequence encoding one or more reprogramming factors selected from the group consisting of Oct4 (Pou5f1), Sox2, cMyc, Klf4, Nanog, Lin 28, and Glis1. In one embodiment, the PSC-derived thyroid follicular epithelial cells have an exogenous nucleic acid sequence encoding the three reprogramming factors Oct4, Sox2, and Klf4.

In one embodiment, the therapeutic compositions or pharmaceutical compositions are sterile. In one embodiment, the therapeutic compositions or pharmaceutical compositions comprise serum or plasma.

The compositions comprising the PSC-derived thyroid thyroid follicular epithelial cells described herein can be administered by any known route. In some embodiments, the compositions can be formulated for local or systemic delivery (e.g., enteral and parenteral). The The compositions comprising the PSC-derived thyroid thyroid follicular epithelial cells described herein may be administered by any convenient route, for example by infusion or bolus injection and may be administered together with other biologically active agents, agents, such as pharmaceutically acceptable surfactants (e.g., glycerides), excipients (e.g., lactose), carriers, diluents and vehicles. In some embodiments, the compositions can be formulated for delivery to specific organs, for example but not limited to the liver, the spleen, the kidney, and the skin. In one embodiment, the compositions are injected directly into the subject, for example, into the liver, the spleen, the kidney, and the skin.

Routes of administration include, but are not limited to direct injection, intradermal, intramuscular, intraperitoneal, intravenous, subcutaneous, transmucosal, buccal, transdermal, and parenteral routes. "Parenteral" refers to a route of administration that is generally associated with injection, including but not limited to intraorbital, infusion, intradermal, intrahepatic, intrarogan, intramuscular, intraperitoneal, intrapulmonary, intravenous, subarachnoid, subcapsular, subcutaneous, transmucosal, or transtracheal. Any other therapeutically efficacious route of administration can be used, for example, infusion or bolus injection, absorption through epithelial or mucocutaneous linings.

The dosage of PSC-derived thyroid thyroid follicular epithelial cells administered to a subject will vary depending upon a variety of factors, including the number of PSC-derived thyroid thyroid follicular epithelial cells available, the level of thyroid hormone released from the PSC-derived thyroid thyroid follicular epithelial cells, and the mode and route of administration of the PSC-derived thyroid thyroid follicular epithelial cells; size, age, sex, health, body weight and diet of the recipient; nature and extent of symptoms of the hypothyroidism, the kind of concurrent treatment, frequency of treatment, and the effect desired.

In some embodiments, treatment of a subject with a therapeutically effective dose can include a single treatment (e.g. the transplantation of PSC-derived thyroid thyroid follicular epithelial cells or a composition comprising PSC-derived thyroid thyroid follicular epithelial cells) or a series of treatments.

In one embodiment, the treatment dosage is at least $1\times10^4$ PSC-derived thyroid thyroid follicular epithelial cells per implantation. In other embodiments, the dosage is at least $5\times10^4$ cells, at least $1\times10^5$ cells, at least $5\times10^5$ cells, at least $1\times10^6$ cells, at least $5\times10^6$ cells, at least $1\times10^7$ cells, at least $5\times10^7$ cells, at least $1\times10^8$ cells, at least $5\times10^8$ cells, at least $1\times10^9$ cells, at least $5\times10^9$ cells, or at least $1\times10^{10}$ cells per implantation into a subject.

In some embodiments, the compositions or pharmaceutical compositions described herein contain about $1\times10^6$ cells to about $30\times10^6$ cells; about $1.0\times10^6$ cells to about $20\times10^6$ cells; about $1.0\times10^6$ cells to about $10\times10^6$ cells, about $2.0\times10^6$ cells to about $30\times10^6$ cells, about $2.0\times10^6$ cells to about $20\times10^6$ cells, or about $2.0\times10^6$ cells to about $10\times10^6$ PSC-derived thyroid thyroid follicular epithelial cells per implantation.

In some embodiments, the compositions or pharmaceutical compositions described herein contain about $1\times10^6$ cells PSC-derived thyroid thyroid follicular epithelial cells, about $2\times10^6$ cells, about $5\times10^6$ cells, about $7\times10^6$ cells, about $10\times10^6$ cells, about $15\times10^6$ cells, about $17\times10^6$ cells, about $20\times10^6$ cells about $25\times10^6$ cells, or about $30\times10^6$ PSC-derived thyroid thyroid follicular epithelial cells per implantation.

Second or subsequent administrations can be administered at a dosage which is the same, less than or greater than the initial or previous dose administered to the individual.

In some embodiments, the dosage of PSC-derived thyroid thyroid follicular epithelial cells administered to a recipient subject is about at least $0.1\times10^5$ cells/kg of bodyweight, at least $0.5\times10^5$ cells/kg of bodyweight, at least $1\times10^5$ cells/kg of bodyweight, at least $5\times10^5$ cells/kg of bodyweight, at least $10\times10^5$ cells/kg of bodyweight, at least $0.5\times10^6$ cells/kg of bodyweight, at least $0.75\times10^6$ cells/kg of bodyweight, at least $1\times10^6$ cells/kg of bodyweight, at least $1.25\times10^6$ cells/kg of bodyweight, at least $1.5\times10^6$ cells/kg of bodyweight, at least $1.75\times10^6$ cells/kg of bodyweight, at least $2\times10^6$ cells/kg of bodyweight, at least $2.5\times10^6$ cells/kg of bodyweight, at least $3\times10^6$ cells/kg of bodyweight, at least $4\times10^6$ cells/kg of bodyweight, at least $5\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, or at least $30\times10^6$ cells/kg of bodyweight of the subject recipient.

In another embodiment, the dosage is at least $2\times10^6$ cells/kg bodyweight of the recipient subject. In other embodiments, the dosage is at least $3\times10^6$ cells/kg of bodyweight, at least $4\times10^6$ cells/kg of bodyweight, at least $5\times10^6$ cells/kg of bodyweight, at least $6\times10^6$ cells/kg of bodyweight, at least $7\times10^6$ cells/kg of bodyweight, at least $8\times10^6$ cells/kg of bodyweight, at least $9\times10^6$ cells/kg of bodyweight, at least $10\times10^6$ cells/kg of bodyweight, at least $15\times10^6$ cells/kg of bodyweight, at least $20\times10^6$ cells/kg of bodyweight, at least $25\times10^6$ cells/kg of bodyweight, or at least $30\times10^6$ cells/kg of bodyweight of the subject recipient.

In another embodiment, the dosage is at least greater than $5\times10^6$ cells/kg bodyweight of the recipient subject.

In another embodiment, the dosage is at least greater than $10\times10^6$ cells/kg bodyweight of the recipient subject.

Second or subsequent administrations can be administered at a treatment dosage which is the same, less than or greater than the initial or previous dose administered to the individual.

A second or subsequent administration may be required during or immediately prior to relapse or a flare-up of symptoms of hypothyroidism. For example, second and subsequent administrations can be given between about one day to 30 weeks from the previous administration of PSC-derived thyroid thyroid follicular epithelial cells. Two, three, four or more total administrations can be delivered to the individual, as needed.

The skilled artisan will appreciate that certain factors may influence the dosage and timing required to effectively treat a subject, including but not limited to hypothyroidism disorder, previous treatments, the general health and/or age of the subject, and other diseases present.

The precise dose to be employed in the formulation will also depend on the route of administration, and the seriousness of the hypothyroidism disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. For example, scoring the severity of the various symptoms associated with hypothyroidism and/or analysis of the level of thyroid hormones in the blood of the subject being treated. Measurements of the degree of severity of a number of symptoms associated with hypothyroidism are noted prior to the start of a treatment and then at later specific time period after the start of the treatment. For example, systematic and periodic monitoring of the thyroid hormones in the blood of the subject before and after receiving the transplanted PSC-derived thyroid follicular epithelial cells. An increase in the blood thyroid hormones levels after transplantation indicates that the treatment is effective in replacing the missing thyroid hormones in the subject.

Induced Pluripotent Stem Cells

In some embodiments, the PSCs described herein are derived from isolated pluripotent stem cells (iPSCs). An advantage of using iPSCs is that the cells can be derived from the same subject to which the progenitor cells are to be administered, thus allowing autologous cell therapy. That is, a somatic cell can be obtained from a subject, reprogrammed to an induced pluripotent stem cell, and then re-differentiated into a thyroid progenitor cell to be administered to the subject (e.g., autologous cells). Since the progenitors are essentially derived from an autologous source, the risk of engraftment rejection or allergic responses is reduced compared to the use of cells from another subject or group of subjects. In some embodiments, the thyroid progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a thyroid stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed disclosure. Thus, any method that re-programs a somatic cell to the pluripotent phenotype would be appropriate for use in the methods described herein.

Reprogramming methodologies for generating pluripotent cells using defined combinations of transcription factors have been described induced pluripotent stem cells. Yamanaka and Takahashi converted mouse somatic cells to ES cell-like cells with expanded developmental potential by the direct transduction of Oct4, Sox2, Klf4, and c-Myc. iPSCs resemble ES cells as they restore the pluripotency-associated transcriptional circuitry and muc of the epigenetic landscape. In addition, mouse iPSCs satisfy all the standard assays for pluripotency: specifically, in vitro differentiation into cell types of the three germ layers, teratoma formation, contribution to chimeras, germline transmission, and tetraploid complementation.

Subsequent studies have shown that human iPS cells can be obtained using similar transduction methods, and the transcription factor trio, OCT4, SOX2, and NANOG, has been established as the core set of transcription factors that govern pluripotency. The production of iPS cells can be achieved by the introduction of nucleic acid sequences encoding stem cell-associated genes into an adult, somatic cell, historically using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-C-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Somatic Cells for Reprogramming

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of thyroid progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sall14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15, Stat3; Grb2; β-catenin, and Bmi1. Such cells can also be characterized by the down-regulation of markers characteristic of the somatic cell from which the induced pluripotent stem cell is derived.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

The disclosure described herein, in a preferred embodiment, does not concern the destruction of a human embryo.

The present disclosure can be defined in any of the following numbered paragraphs:

[1] An ex vivo or in vitro method for producing a thyroid follicular epithelial cell comprising: (a) culturing a thyroid progenitor cell in a differentiation medium under condition and time sufficient to further differentiate the thyroid progenitor cell along the thyroid lineage, wherein the differentiation medium comprising fibroblast growth factor 2 (basic) (FGF2), wherein the thyroid progenitor cell co-expresses a NK2 homeobox 1 (Nkx2-1) protein and a paired box 8 (Pax8) protein, wherein the co-expression of Nkx2.1 and Pax8 are the products of endogenous genes within the cell, and the Nkx2.1 and Pax8 co-expressing thyroid progenitor cell does not comprise exogenously delivered nucleic acid sequences encoding for the co-expression of Nkx2.1 and Pax8 in the cell; and (b) then culturing the thyroid progenitor cell of step (a) in a maturation medium comprising dexamethasone and cAMP, dexamethasone and thyroid stimulating hormone (TSH), or TSH, under condition and time sufficient to produce a Nkx2-1+/Pax8+ co-expressing cell that also expresses early and mature thyroid markers: thyroglobulin (Tg+), thyroid stimulating hormone receptor (Tsh+), sodium iodine symporter (Nis+), and thyroid peroxidase (Tpo+).

[2] The method according to paragraph 1, wherein the thyroid progenitor cell is prepared by contacting an endodermal cell with a thyroid lineage culture medium to differentiate the endodermal cell into the thyroid lineage without exogenously delivered nucleic acid sequences resulting in the forced over-expression of the Nkx2-1 protein and the Pax8 protein in the endodermal cell, thereby producing a Nkx2.1+ and Pax8+ thyroid progenitor cell, wherein the thyroid lineage culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF).

[3] An ex vivo or in vitro method for producing a thyroid follicular epithelial cell comprising: (a) culturing an endodermal cell in a thyroid lineage culture medium under condition and time sufficient to differentiate the endodermal cell into the thyroid lineage without exogenously delivered nucleic acid sequences resulting in the forced over-expression of a NK2 homeobox 1 (Nkx2-1) protein and a paired box 8 (Pax8) protein in the endodermal cell, thereby producing a thyroid progenitor cell, wherein the differentiation culture medium comprising: (i) bone morphogenetic protein 4 (BMP4), and (ii) fibroblast growth factor 2 (basic) (FGF2), wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF), thereby producing Nkx2-1 and Pax8 (Nkx2-1+/Pax8+) co-expressing thyroid progenitor cell therefrom, but not a Nkx2-1 expressing or a Pax8 expressing cell; (b) culturing a thyroid progenitor cell in a differentiation medium under condition and time sufficient to further differentiate the thyroid progenitor cell along the thyroid lineage, the differentiation medium comprising fibroblast growth factor 2 (basic) (FGF2); and (c) then culturing the thyroid progenitor cell of step (b) in a thyroid maturation medium comprising dexamethasone and cAMP, dexamethasone and thyroid stimulating hormone (TSH), or TSH under condition and time sufficient to produce a Nkx2-1+/Pax8+ co-expressing cell that also express early and mature thyroid markers: thyroglobulin (Tg+), thyroid stimulating hormone receptor (Tsh+), sodium iodine symporter (Nis+), and thyroid peroxidase (Tpo+).

[4] An ex vivo or in vitro method for producing a thyroid follicular epithelial cell from a pluripotent stem cell (PSC) comprising: (a) culturing a pluripotent stem cells (PSC) in a culture medium under conditions sufficient to initiate entry and formation into an endodermal cell; (b) culturing the endodermal cell in a thyroid lineage culture medium under condition and time sufficient to differentiate the endodermal cell into the thyroid lineage without exogenously delivered nucleic acid sequences resulting in the forced over-expression of a NK2 homeobox 1 (Nkx2-1) protein and a paired box 8 (Pax8) protein in the endodermal cell, thereby producing a thyroid progenitor cell, wherein the differentiation culture medium comprising: (i) bone morphogenetic protein 4 (BMP4), and (ii) fibroblast growth factor 2 (basic) (FGF2); wherein the thyroid lineage culture medium does not contain: (iii) Wingless-Type MMTV Integration Site Family protein, member 3A, (Wnt3A), (iv) fibroblast Growth Factor 10 ((FGF10), (v) keratinocyte Growth Factor (KGF), and (vi) epidermal growth factor (EGF), thereby producing Nkx2-1 and Pax8 (Nkx2-1+/Pax8+) co-expressing thyroid progenitor cell therefrom, but not a Nkx2-1 expressing or a Pax8 expressing cell; and (c) culturing the thyroid progenitor cell with a differentiation medium under condition and time sufficient to further differentiate the thyroid progenitor cell along the thyroid lineage, the differentiation medium comprising fibroblast growth factor 2 (basic) (FGF2); and (d) culturing the thyroid progenitor cell of step (c) with a thyroid maturation medium comprising dexamethasone and cAMP, dexamethasone and thyroid stimulating hormone (TSH), or TSH, under condition and time sufficient to produce a Nkx2-1+/Pax8+ co-expressing cell that also expresses early and mature thyroid markers: thyroglobulin (Tg+), thyroid stimulating hormone receptor (Tsh+), sodium iodine symporter (Nis+), and thyroid peroxidase (Tpo+).

[5] The method according to paragraph 2, 3 or 4, wherein the endodermal cell is an anterior/foregut endodermal cell.

[6] The method according to any one of paragraphs 1-5, wherein the differentiation medium further comprising fibroblast growth factor 10 (FGF10).

[7] The method according to any one of paragraphs 1-6, wherein the differentiation medium further comprising BMP4.

[8] The method according to any one of paragraphs 1-7, wherein the differentiation medium further comprising TSH.

[9] The method according to any one of paragraphs 1-8, wherein the maturation medium further comprising at least a fibroblast growth factor.

[10] The method according to paragraph 9, wherein the fibroblast growth factor is FGF2 or FGF10.

[11] The method according to any one of the preceding paragraphs, wherein the resultant Nkx2-1+/Pax8+/Tg+/Tsh+/Nis+/Tpo+ cells do not express differentiated lung markers: surfactant, pulmonary-associated protein C (Sftpc) and secretoglobin family 1A member 1 (Scgb1a1).

[12] The method according to any one of the preceding paragraphs, wherein the resultant Nkx2-1+/Pax8+/Tg+/Tsh+/Nis+/Tpo+ cells also express Forkhead Box E1 protein (Foxe1) and thyroidally-expressed homeobox protein (Hhex).

[13] The method according to any one of the preceding paragraphs, wherein the resultant Nkx2-1+/Pax8+/Tg+/Tsh+/Nis+/Tpo+ cells also express epithelial markers E-Cadhedrin (E-Cad) and epithelial cell adhesion molecule (EpCam).

[14] The method according to any one of the preceding paragraphs, the method further comprising selecting for Nkx2-1+/Pax8+ expressing cells obtained and removing Nkx2-1+/Pax8−, Nkx2-1−/Pax8−, and Nkx2-1−/Pax8+ expressing cells.

[15] The method according to any one of the preceding paragraphs, the method further comprising determining diploid expression of Nkx2-1 in the resultant cells.

[16] The method according to any one of the preceding paragraphs, the method further comprising selecting for Nkx2-1+/Pax8+/Tg+/Tsh+/Nis+/Tpo+/expressing cells obtained.

[17] The method according to any one of the preceding paragraphs, the method further comprising selecting for Foxe1+/Hhex+ expressing cells obtained.

[18] The method according to any one of the preceding paragraphs, the method further comprising selecting for E-Cad+/EpCam+ expressing cells obtained.

[19] The method according to any one of the preceding paragraphs, the method further comprising selecting for Sftpc−/Scgb1a1− expressing cells obtained.

[20] The method according to any one of the preceding paragraphs, wherein in the Nkx2-1+/Pax8+ expressing cells are cultured in a 3D matrix support material.

[21] The method according to paragraph 20, wherein in 3D matrix support material is matrigel.

[22] A population of thyroid follicular epithelial cells produced by the method of any one of the preceding paragraphs.

[23] The population of thyroid follicular epithelial cells of paragraph 22, wherein the cells synthesize and secrete thyroid hormones in vivo.

[24] A composition comprising a population of thyroid follicular epithelial cells of paragraph 22 or 23.

[25] A method for treating hypothyroidism in a subject in need thereof comprising transplanting a population of thyroid follicular epithelial cells of paragraph 22 or 23 into the subject.

[26] A method for treating hypothyroidism in a subject in need thereof comprising transplanting a composition of thyroid follicular epithelial cells of paragraph 24.

[27] The treatment method of paragraph 25 or 26, the method further comprises selecting a subject diagnosed of having hypothyroidism.

[28] The treatment method of paragraph 25 or 26, the method further comprises harvesting a population of pluripotent stem cells from the subject to ex vivo produce a population of thyroid follicular epithelial cell for transplantation.

[29] The treatment method of paragraph 28, wherein the pluripotent stem cells are harvested from the bone marrow (BM), adipose tissue (AT), peripheral blood (PB), placenta, and umbilical cord blood (UBC).

[30] The treatment method of paragraph 25 or 26, wherein the thyroid follicular epithelial cells are autologous or allogenic to the subject.

[31] The treatment method of paragraph 25 or 26, wherein the thyroid follicular epithelial cells are cryopreserved prior to transplantation into the subject.

[32] A population of thyroid follicular epithelial cells produced ex vivo from a population of pluripotent stem cells for use in the treatment of hypothyroidism.

[33] A population of thyroid follicular epithelial cells produced ex vivo from a population of thyroid progenitor cells for use in the treatment of hypothyroidism.

[34] A population of thyroid follicular epithelial cells produced ex vivo from a population of endodermal cells for use in the treatment of hypothyroidism.

[35] A population of thyroid follicular epithelial cells produced ex vivo from a population of pluripotent stem cells for use in the manufacture of medicament in the treatment of hypothyroidism.

[36] A population of thyroid follicular epithelial cells produced ex vivo from a population of thyroid progenitor cells for use in the manufacture of medicament in the treatment of hypothyroidism.

[37] A population of thyroid follicular epithelial cells produced ex vivo from a population of endodermal cells for use in the manufacture of medicament in the treatment of hypothyroidism.

This disclosure is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the disclosure described herein. Such equivalents are intended to be encompassed by the following claims.

EXAMPLE

Materials and Methods
Animal Maintenance

All mouse studies involving mice carrying GFP and tdTomato reporters were approved by the Institutional Animal Care and Use Committee of Boston University School of Medicine. All murine transplantation experiments were approved by Beth Israel Deaconess Medical Center Institutional Animal Care and Use Committee. We previously published the generation of Nkx2-1GFP mice (C57BL/6j) (Longmire et al., 2012). Pax8cre mice were a generous gift from Meinrad Busslinger (Research Institute of Molecular Pathology, Vienna Biocenter, Austria) (Bouchard et al., 2004)). All transplantation experiments described were performed in female 129X1/SvJ mice (Jackson Labs 000691).

ESC/iPSC Mouse Lines

The Nkx2-1GFP reporter mouse ESC line was generated as described previously by targeting the enhanced GFP reporter to one allele of the endogenous Nkx2-1 locus by homologous recombination in W4/129S6 ESCs (Longmire et al., 2012), replacing endogenous sequences from the second ATG start site through the end of the Nkx2-1 homeobox (positions 7957-9480 in GenBank locus MMU19755). The Nkx2-1mCherry ESC line was generated as previously described (Bilodeau et al., 2014) by targeting an internal ribosomal entry site (IRES) coupled to the mCherry reporter cDNA into the Nkx2-1 locus 3'UTR in RI mESCs. All ESC and iPSC lines were maintained in the undifferentiated state on mouse embryonic fibroblast feeder layers using serum containing media supplemented with LIF (ESGRO Chemicon ESG-1106).

ESC and iPSC Differentiation

Definitive endoderm induction was performed in complete serum-free differentiation medium (cSFDM) consisting of 75% IMDM (Invitrogen 12440) and 25% Ham's Modified F12 medium (Cellgro 10-080-CV) supplemented with N2 and B27+RA (Invitrogen 17502-048 and 17504-44), 0.05% BSA (Invitrogen 15260-037), 200 mM L-glutamine (Invitrogen 25030-081), 0.05 mg/ml ascorbic acid (Sigma A4544) and $4.5 \times 10-4M$ MTG (Sigma M6145) as previously described (Gouon-Evans et al., 2006, Longmire et al., 2012). Undifferentiated ESCs were trypsinized to form a single cell suspension and plated onto Petri dishes (500,000 cells/10 cm dish) resulting in the formation of embryoid bodies (EBs) over 60 hours. EBs were dissociated by trypsinization (0.05%, 1 min, 37° C.) and plated as single cells into cSFDM supplemented with 50 ng/ml Activin A (R&D systems 338-AC) for an additional 60 hours.

For Anteriorization of endoderm, on day 5 (120 total hours of differentiation) EBs were plated onto p100 Petri dishes in Nog/SB media: cSFDM supplemented with 100 ng/ml mNoggin (R&D 1967-NG) and 10 µM SB431542 (Sigma S4317) as previously described (Longmire et al., 2012). For Nkx2-1+ endoderm induction, EBs were plated on gelatin coated 6 well plates at the equivalent density of 200,000 cells/well in Specification media: cSFDM supplemented as stated in the text with 100 ng/ml mWnt3a (R&D 1324-WN), 10 ng/ml hFGF10 (R&D 345-FG), 10 ng/ml mKGF (R&D 5028-KG), 10 ng/ml mBMP4 (R&D 5020-BP), 20 ng/ml hEGF (R&D 236-EG), 250 ng/ml mFGF2 (R&D 3139-FB) and 100 ng/ml Heparin Sodium Salt (Sigma H4784). Nkx2-1GFP+, Nkx2-1mCherry+ cells, or the populations otherwise indicated in the text were sorted using MoFlo or FACSARIA II SORP high speed cell sorters and replated onto gelatin-coated 24 well plates on day 12-14 at a density of $5 \times 10^4$ cells/well. Where indicated in the text, small molecule inhibitors were dissolved in DMSO according to manufacturer's instructions and added to the culture media from day 6 to 14 at the following working concentrations: Dorsomorphin 4 µM (Sigma P5499), PD98059 20 µM, SB203580 10 µM (both from Cell Signaling Technology, PHZ1164 and 5633), and LY294002 25 tM (Promega V1201).

Further differentiation and maturation of Nkx2-1+ sorted cells was performed in either 2D or 3D culture conditions, as indicated in the text. For 2D differentiation cells sorted on day 14 were replated and grown for 8 more days in cSFDM supplemented with 250 ng/ml mFGF2, 100 ng/ml hFGF10 and 100 ng/ml Heparin Sodium Salt. On day 22, the media was changed to DCI+K: Ham's F12 media, 15 mM HEPES (pH 7.4), 0.8 mM $CaCl_2$ (Sigma C1016), 0.25% BSA, ITS supplement (5 µg/ml insulin, 5 µg/ml transferrin, 5 ng/ml Sodium Selenite; BD 354352), 50 nM Dexamethasone (Sigma D4902), 0.1 mM 8-Br-cAMP (Sigma B7880), 0.1 mM IBMX (Sigma 15879) and 10 ng/ml KGF.

For 3D culture and transplantation studies ESC-derived cells were sorted on day 12 of differentiation and purified Nkx2-1+ cells were re-plated in pure growth factor reduced Matrigel drops (Matrigel Basement Membrane Matrix Growth Factor Reduced, Phenol Red Free, Corning 356231) at a density of 65,500 cells in 105 µl Matrigel per well in a 24-well plate. From day 12 to 26 cells were grown in cSFDM supplemented with 250 ng/ml mFGF2, 100 ng/ml hFGF10, 100 ng/ml Heparin Sodium Salt, 50 ng/ml mIGF-1 (R&D 791-MG), 10 µg/ml insulin (Sigma 10516), 25 ng/ml hEGF and 1 mU/ml bTSH (Los Angeles Biomedical Research Institute, National Hormone and Peptide Program, Torrance, Calif.). During the first 48 hours after sorting media was supplemented with 10 µM Y27632 (Sigma Y0503). From day 20-26 5 µg/ml ITS was included in the media. On days 26-30 media was changed to thyroid maturation media [Ham's F12 supplemented with 15 mM HEPES, 0.8 mM CaCl2, 100 ng/ml Heparin Sodium Salt, 0.25%, BSA, 50 ng/ml mIGF-1, 5 µg/ml insulin, 5 µg/ml ITS, 25 ng/ml hEGF, 50 nM Dexamethasone, and 100 mU/ml bTSH]. For cultures longer than 30 days, cells were splitted using Dispase (Corning 354235) on Day 30 and re-embedded in pure Matrigel, and fed with thyroid maturation media until the harvest day indicated in the text.

Generation of Nkx2-1GFP/Pax8tdTomato Trace Bifluorescent Reporter Mice and iPSC Line Double Nkx2-1GFP reporter Pax8tdTomato trace mice were generated by breeding a Rosa26-lox-Stop-lox-tdTomato reporter mouse (Jackson Labs 007909) with a Pax8cre/+ mouse and breeding double mutant male mice of the offspring with Nkx2-1GFP/+ females (C57Bl6j background). Whole mounts of dissected lung and thyroid tissue harvested at the time points indicated in the text were imaged with an Olympus stereo fluorescence imaging microscope (model SZX16, Olympus America, Central Valley, Pa.) at the Cellular Imaging Core of Boston University. For iPSC line derivation, a triple mutant E14.5 embryo (Nkx2-1GFP reporter Pax8tdTomato trace) was dissected and mouse embryonic fibroblasts were expanded. Passage 3 fibroblasts were co-infected with a previously published reprogramming system (Sommer et al., 2009), consisting of a Doxycycline-inducible mouse STEMCCA lentiviral vector (encoding Oct4, Klf4, Sox2, and cMyc) and a CMV-rTTA lentiviral vector. Cells were incubated with ESC media supplemented with LIF, and treated with Doxycycline (Sigma D9891) at 1 µg/ml for 10 days. At day 20 of culture (10 days after Doxycycline withdrawal) colonies were picked to establish iPSC lines. Candidate iPSC clones surviving passaging were stained for Alkaline Phosphatase and SSEA-1 to assess expression of pluripotency markers (ES Cell Characterization Kit, Millipore SCR001). Passage 15-20 was used for differentiation experiments.

Xenopus Embryo Experiments

Xenopus embryos were generated by in vitro fertilization and assayed by in situ hybridization or confocal immunostaining as previously described (Rankin et al., 2015). Small molecule inhibitors were dissolved in DMSO according to manufacturer's instructions and added to the embryo culture saline at the following working concentrations: 10 µM SU5402 (Tocris Bioscience), 40 µM DMH-1 (Sigma), 50 µM XAV939 (Sigma) and 10 µM BMS493 (Tocris Bioscience). Foregut explants were dissected from stage NF15 and treated with Dispase (BD Pharmingen) for 15 minutes and then the mesoderm was manually removed. Foregut endoderm was then cultured in 0.5× Modified Barth's Saline with 0.1% BSA with or without 500 ng/ml rhFGF2 and 50 ng/ml rhBMP4 (R&D systems).

Mouse Foregut Explants

Whole foreguts were dissected from E8.5 embryos (6-8 somite pairs) in Hank's balanced salt solution (HBSS) then explanted onto 8 µm pore size Whatman Nucleopore Track-Etch Membranes (Millipore). Explants were cultured for 2-3 days in a base medium (BGJb medium (Gibco)+10% fetal bovine serum (FBS, Sigma) and 0.2 mg/ml ascorbic acid) containing either the BMPR inhibitor DMH-1 (1.5 µM, Tocris) or DMSO as a vehicle control. Whole mount immunostaining was performed using a modification of the method of Ahnfelt-Ronne et al. (Ahnfelt-Ronne et al., 2007). The primary antibodies used were: guinea pig anti-Nkx2-1 (Seven Hill Bioreagents; 1:500), rabbit anti-Pax8 (Protein Tech; 1:500) and rat anti-Ecad (R&D; 1:2000). After staining, samples were cleared with Murray's clear (2:1 benzyl benzoate: benzyl alcohol) and imaged using a Nikon A1Rsi inverted laser confocal microscope. Imaris software was used to analyze the images. DMH-1 treated and control explants were harvested and lysed in Laemmli buffer after 24 hours of treatment. Lysates were electrophoresed on a 10-20% Tris-glycine gel under reducing conditions, Western blotted, and probed with antibodies (Cell Signaling) to detect total Smad1/5 and pSmad 1/5 content; β-actin content served as a loading control.

Thyroid Ablation

Generation of hypothyroid mice was performed as described previously (Abel et al., 1999). In brief, 6 week old female mice were put on a low iodine diet (Harlan Laboratories TD.95007Teklad) for 8 days. Thereafter they were given a single intraperitoneal injection of 150 PCi of I311 (Cardinal Health). Three weeks after RAI administration hypothyroidism was confirmed and 4 weeks after thyroid ablation surgery was performed.

Cell Preparation for In Vivo Transplantation

Nkx2-1+ cells sorted on day 12 and then cultured in 3D conditions in Matrigel® drops in 24-well plates until day 30 of differentiation were washed with PBS and incubated with 500 µl of Dispase for 40-50 minutes at 37° C. Cells were transferred to a 15 ml falcon tube and washed twice with IMDM and centrifuged at 300 g for 1 minute at each step. The cell pellet was re-suspended in 40 µl of thyroid maturation media (see ESC/iPSC differentiation above) and transferred to a Polyethylene tube (PE50 36FT, Braintree Scientific Inc.) and centrifuged at 300 g for 2 minutes. 8-10 µl of a pellet (corresponding to 2.5-3 million cells) were transplanted under the left kidney capsule.

Kidney Capsule Transplantation Surgery

Mice were anesthetized with ketamine (100 mg/kg, i.p.; Fort Dodge Animal Health) and Xylazine (10 mg/mg, i.p.; LLoryd Laboratories). The lateral site of the left abdomen was shaved, scrubbed with antiseptic solution and a vertical subcostal incision of the skin, muscle and peritoneum was made (approximately 2.5 cm; dorsolateral approach). The left kidney was exposed by blunt dissection and cells were injected under the left kidney capsule using a Hamilton micro syringe under a dissecting microscope. The abdominal wall was closed and the skin sutured.

Blood Chemistry and Hormonal Analyses

Blood was taken from the submandibular vein and collected in EDTA-treated tubes. Cells were removed from plasma by centrifugation for 10 minutes at 9000 g using a refrigerated centrifuge. Total plasma T4 and T3 were measured by solid-phase RIA (Coat-a-Count, Siemens Diagnostic Products Corp., Los Angeles, Calif.) according to the manufacturer's instructions in 25 and 50 µl of plasma, respectively. Circulating TSH was measured via Milliplex MAP (rat thyroid hormone TSH panel; Millipore) in 2-10 µl of sample. T3 was measured only when at least 50 Pl of plasma were left after measuring total T4 and TSH.

Imaging

Mice were anesthetized using isoflurane and a standard protocol for SPECT imaging was performed, where approximately 0.300 mCi Tc99-Pertechnatate was injected retroorbitally one hour before imaging on the NanoSPECT/CT (inVICRO). Animals were imaged 1 hour post-injection at the Longwood Small Animal Imaging Facility, Boston, Mass. SPECT/CT imaging was performed using a Minerve anesthesia bed on a NanoSPECT/CT™ imaging system (inVICRO, Boston, Mass.). The acquisition software used was Nucline (Mediso, Budapest, Hungary). After SPECT imaging, anesthetized mice were then imaged by MRI system (ASPECT), without moving the mouse. The common mouse bed, exchangeable between the MRI and SPECT/CT systems, was placed inside the ASPECT standard 35 mm mouse coil. MR images were acquired using a Ti weighted SE Classic multislice sequence (TE=11.4, TR=400, slice thickness=1 mm, FOV=40 mm). The acquisition software used was NRGSYS (ASPECT, Israel). Resulting SPECT/MR images were analyzed and co-registered manually using Vivoquant software (inVICRO).

TSH Response Test

To suppress endogenous production of T4 and TSH, T3 (4 µg per 100 g body weight (BW); Sigma T6397) was given daily by intraperitoneal injection for 4 days. 15 hours after the last injection, blood was taken from the submandibular vein to measure T4 and TSH after which a single injection of highly purified bTSH (Los Angeles Biomedical Research Institute, National Hormone and Peptide Program. Torrance, Calif.) at 30 mU per 100 g BW was given. 3 hours later blood samples were taken to assess the increase of total T4. Five mice per group (positive control group, Sham, and D30 ESCs recipients) were included in the experiment.

Histological Analyses

Cultured cells and kidneys fixed in 4% paraformaldehyde or formalin, were embedded in paraffin and 5 µm sections prepared. Standard methods for Hematoxylin and Eosin (H&E) staining were performed (AML Labs, Inc, Baltimore, Md.). For immunohistochemistry sections were deparaffinized and rehydrated. Antigen retrieval was performed by heating the sections in antigen retrieval solution (Dako S-1699). Sections were incubated at 4° C. overnight with the following primary antibodies: anti-Nkx2-1 (rabbit monoclonal, Abcam ab76013 and mouse monoclonal, Dako M3575; 1:200-600), anti-Pax8 (rabbit monoclonal, Abcam ab122944; 1:50), anti-Tg (mouse monoclonal, Abcam ab80783; 1:100), anti-T4 (mouse monoclonal, Thermo Scientific Pierce Products MA5-14716; 1:50) and anti-mCherry (rat monoclonal, Life technologies Ml 1217, 1:100). The staining was detected with either Alexa Fluorophore-conjugated secondary antibodies for immunofluorescence (donkey anti-mouse, donkey anti-rabbit: 1:200, Molecular probe, Invitrogen) or with the ImmPRESS Reagent (Vector Labs MP 7401 and MP 7444) for immunohistochemistry followed by incubation with diaminobenzidine peroxidase substrate (DAB, Vector Labs SK-4100) according to the manufacturer's instructions. Fluorescent and phase contrast images were captured on a Nikon Eclipse Ni upright microscope using Nikon Elements D4.00 software.

*Xenopus* embryo tissue sections were immunostained with anti-phospho-ERK1/2-Thr202/Tyr204 (rabbit polyclonal, Cell Signaling 9101), anti-phospho-Smad1/5/8 (rabbit polyclonal, Cell signaling 9511), anti-Nkx2-1 (rabbit polyclonal, Santa cruz sc-13040) and anti-Sox2 (mouse monoclonal, Abcam 79351) as previously described (Rankin et al., 2015).

Intracellular Staining of Nkx2-1 Protein for Flow Cytometry

Cells were monodispersed with trypsin and fixed in suspension in 1.6% PFA at 37° C., washed twice in FACS buffer (1x PBS, 0.5% BSA and 0.02% NaN3), and permeabilized with Permeabilization Wash Buffer (Biolegend 421002). Primary antibody rabbit anti-human Nkx2-1 (Abcam 76013) was used at a 1:50 dilution in the same buffer for 30 min at RT. After washing twice, Alexa 647 conjugated goat-anti-rabbit antibody (Invitrogen A21245) was used as secondary at 1:100 dilution, washed twice and resuspended in FACS buffer for flow cytometry analysis using a BD FACSCalibur (BD Bioscience).

Real Time Quantitative Polymerase Chain Reaction (qPCR)

RNA (for FIGS. 1 to 3 and 11c) was extracted from cells using the RNeasy kit (Qiagen 74104) following the manufacturer's protocol. 150 ng of RNA was reverse transcribed to cDNA using TaqMan reverse transcription reagents (Applied Biosystems N8080234) and the manufacturer's protocol. cDNA template was diluted 1:4, and 2 µl of the diluted template was used per 25 µl real time PCR reaction using Taqman Fast Universal PCR Master Mix (Applied Biosystems 4352042) and run in technical triplicates up to 40 cycles of PCR on the Applied Biosystems StepOne machine. Alternatively, 1 µl of the diluted template was used per 13 µl real time reaction on the Applied Biosystems 7900HT Real Time PCR System. Relative gene expression, normalized to 18S control, was calculated as fold change in 18S-normalized gene expression, over baseline, using the $2^{(-\Delta\Delta C_T)}$ method. Baseline, defined as fold change=1, was set to undifferentiated embryonic stem cell levels, or if undetected, a cycle number of 40 was assigned to allow fold change calculations.

Figure 11B:
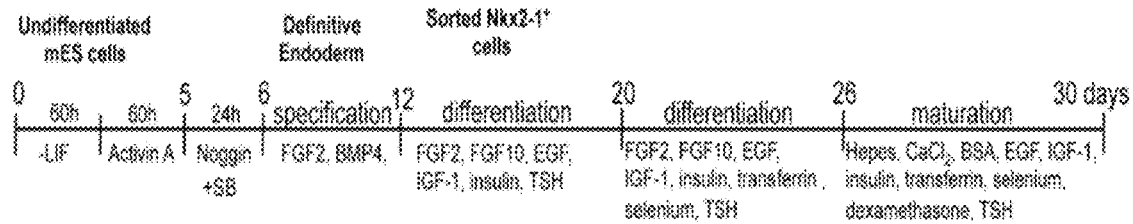
Figure 11C:
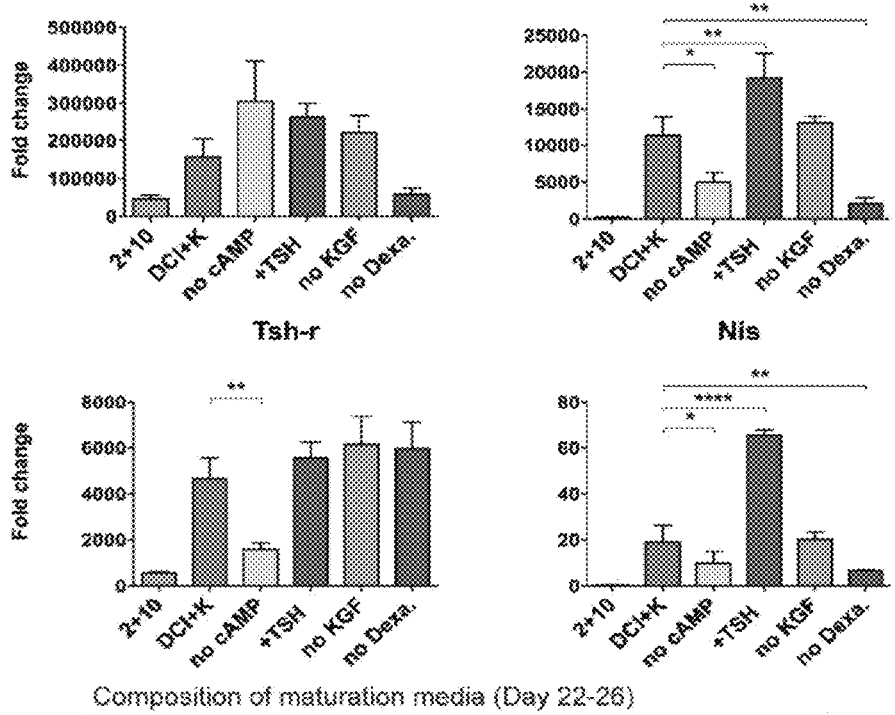

For FIGS. 5 and 11 (except FIG. 11c) total RNA was extracted from cultured cells using Stat-60 reagent (Tel-Test Cs-502). Then, 150 ng of total RNA was reverse transcribed using a SuperScript Vilo cDNA synthesis kit from Invitrogen. qPCR was performed in duplicate using the 800HT thermal cycler (Applied Biosystems). Relative mRNA levels were calculated using the standard curve method and normalized to peptidylprolyl isomerase A (cyclophilin). Cyclophilin expression was quantified with custom-made primers and probe (Forward primer: GGT GGA GAG CAC CAA GAC AGA, SEQ. ID. NO: 1), Reverse primer: GCC GGA GTC GAC AAT GAT G, SEQ. ID. NO: 2; Probe: AGC-CGGGACAAGCCACTGAAGGAT, SEQ. ID. NO: 3).

TaqMan gene expression assays for all mRNAs were purchased from Applied Biosystems and are listed in the following Table 1:

| | | |
|---|---|---|
| 18S rRNA | Applied Biosystems | 4313413e |
| Nkx2-1 | Applied Biosystems | Mm00447558_m1 |
| Pax8 | Applied Biosystems | Mm00440623_m1 |
| Tg | Applied Biosystems | Mm00447525_m1 |
| Tsh-r | Applied Biosystems | Mm00442027_m1 |
| Slc5a5 (Nis) | Applied Biosystems | Mm00475074_m1 (FIG. 1-3) |
| | | Mm01351811_m1 (FIG. 5) |
| Tpo | Applied Biosystems | Mm00456355_m1 |
| Foxe1 | Applied Biosystems | Mm00845374_s1 |
| Hhex | Applied Biosystems | Mm00433954_m1 |

Statistical Analysis

Data are presented as sample means and standard deviations (SD) or standard errors of the mean (SEM), as indicated in the text and in each figure legend. Sample numbers are stated specifically within the text or figure legends. Differences between groups were measured, which included unpaired 2-tailed Students t-test, 1-way or 2-way analysis of variance (ANOVA) with Tukey's multiple-comparison post hoc test.

Ingenuity Pathway Analysis and interrogation of global mRNA expression profiles Previously published data sets (Longmire et al., 2012) (generated with Affymetrix GeneChip Mouse Gene 1.0 ST arrays) were re-analyzed to generate lists of differentially expressed genes comparing Nkx2-1GFP+vs Nkx2-1GFP− sorted ESC-derived cells on day 14 of differentiation. Briefly, three biological replicates were prepared by sorting cell pellets of Nkx2-1GFP+vs Nkx2-1GFP− cells on day 14 of differentiation. Total RNA was extracted using miRNeasy Mini Kit (Qiagen). Quality-assessed RNA samples were hybridized to Affymetrix GeneChip® Mouse Gene 1.0 ST arrays based on Affymetrix standard microarray operating procedure. All raw data files obtained by Affymetrix scanner passed data quality control steps prior to robust multiarray averaging (RMA) normalization through the Affymetrix expression console. The normalized data underwent statistical analysis using a linear model for microarray data analysis package to determine differentially expressed genes between the GFP+ and GFP− populations, with a false discovery rate (FDR)-adjusted p-value cutoff of <0.05 (resulting in identification of 1267 genes that were differentially expressed between GFP+vs GFP-populations. The data discussed in this publication have been deposited in NCBIs Gene Expression Omnibus and are accessible through GEO Series accession number at the world wide website for the National Center for Biotechnology Information located at the United States National Library of Medicine, a division of the National Institutes of Health, under the Accession number GSE35063. The list of 1267 genes that passed filter criteria and were differentially expressed were then analyzed through the use of QIAGEN's Ingenuity® Pathway Analysis software (IPA®, QIAGEN Redwood City) according to the manufacturer's instructions in order to identify lists of candidate pathways active in the day 14 cell populations.

Results

Nkx2-1+ Thyroid Cells are Specified from ESC-Derived Endodermal Precursors Upon Stimulation with Exogenous BMP4 and FGF2

Figure 7A:
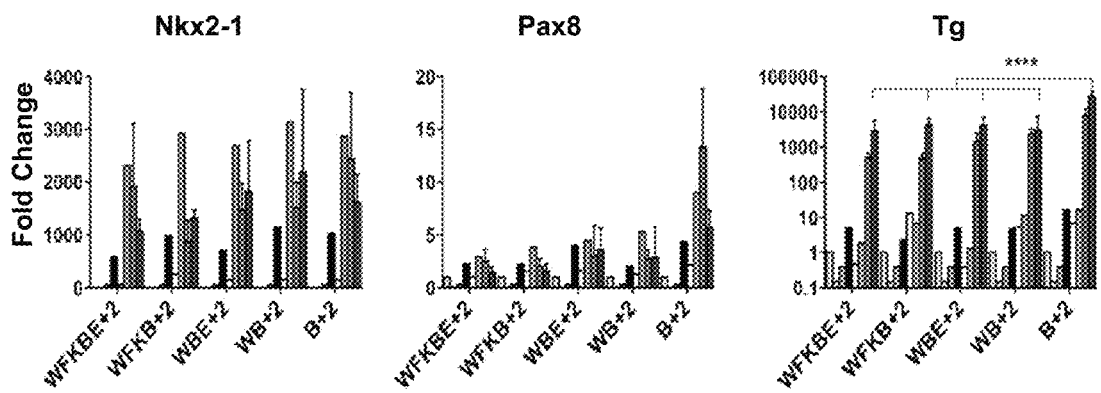
FIGS. 7a-7c show that BMP4 and FGF2 are sufficient to specify Nkx2-1GFP+ endodermal cells with thyroid potential, and Nkx2-1 haploinsufficiency does not affect initial specification of Nkx2-1+ endodermal precursors.
Figure 7A:
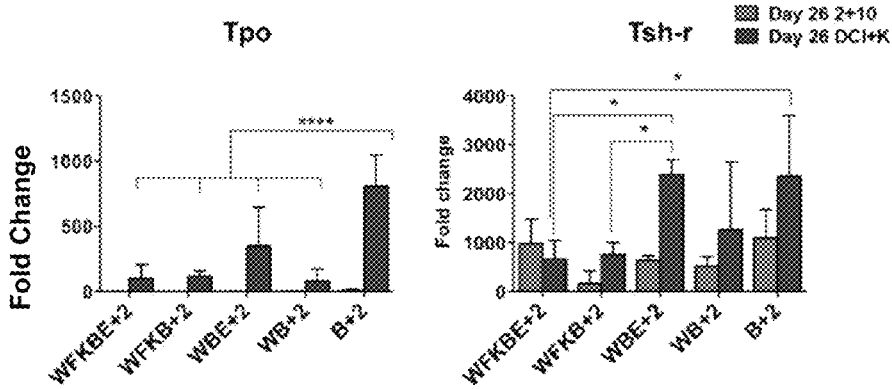

We previously developed a directed differentiation protocol to produce ESC-derived definitive endodermal cells that were competent to form thyroid and lung epithelial lineages in serum-free media (Longmire et al., 2012). We employed an ESC line (Nkx2-1GFP) engineered to carry a knock-in GFP reporter cDNA targeted to the locus encoding the homeodomain-containing transcription factor Nkx2-1 (also known as thyroid transcription factor-1; Ttf1 or Titf1), a transcriptional regulator essential for thyroid and lung development. Within endoderm, Nkx2-1 is only expressed in lung or thyroid epithelia and is the first known protein to be induced upon endodermal specification to lung or thyroid fates, making induction of this locus an ideal reporter of lung or thyroid lineage specification. Nkx2-1+ cells induced from ESC-derived endoderm using our previously published (Longmire et al., 2012) 6 factor cocktail (WFKBE+2; FIG. 1a) expressed thyroid epithelial-specific genes, such as thyroglobulin (Tg). However, these cells did not display full thyroid maturation as the genes encoding all proteins required for iodine metabolism and thyroid hormone biosynthesis were not robustly expressed, such as the sodium iodine symporter (Nis) and thyroid peroxidase (Tpo), (FIG. 7a and data not shown). Microarray analysis of the global mRNA expression profiles of these ESC-derived Nkx2-1GFP+ endodermal progenitors (containing both lung and thyroid lineages) sorted on day 14 of differentiation, compared to the sorted GFP negative population (Longmire et al., 2012, FIG. 1a, and Tables 2 and 3), revealed multiple signaling pathways were active in culture at this early stage of differentiation, soon after thyroid cell fate induction, but prior to the expression of thyroid differentiation genes. Ingenuity Pathway Analysis revealed differentially expressed genes indicative of significant activation of BMP, Wnt, EGF, and FGF signaling pathways were present on day 14 of differentiation (Tables 2 and 3).

Figure 1B:
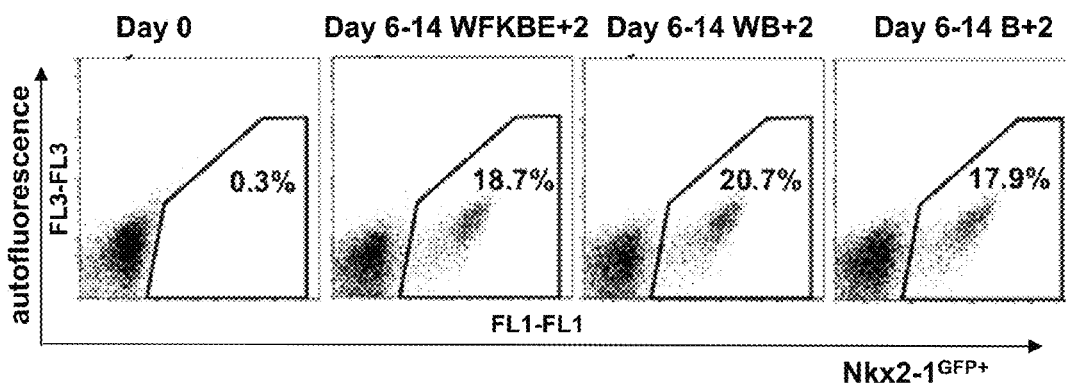

Through sequential withdrawal of each individual factor from the WFKBE+2 cocktail, we found BMP4 and FGF2 (Longmire et al., 2012) to be the only factors that were indispensible for efficient Nkx2-1+ endodermal induction. Although we previously observed that Wnt3a augments proliferation rates in this protocol (Longmire et al., 2012), it too was dispensable for Nkx2-1 induction efficiency from ESC-derived endoderm (FIG. 1b). An induction media composed of BMP4, FGF2 and Wnt3a led to the maximum efficiency of Nkx2-1+ cell specification by day 14 and sorted Nkx2-1GFP+ cells at this time point, either with or without Wnt3a, were competent to subsequently express thyroid differentiation markers, Tg and Tsh-r (thyroid stimulating hormone receptor), and maturation markers, Nis and Tpo (FIGS. 1b and 7a). Therefore, we concluded that BMP4 and FGF2 are sufficient to specify endodermal cells in vitro towards Nkx2-1+ endodermal progenitor cells with thyroid potential.

Figure 1C:
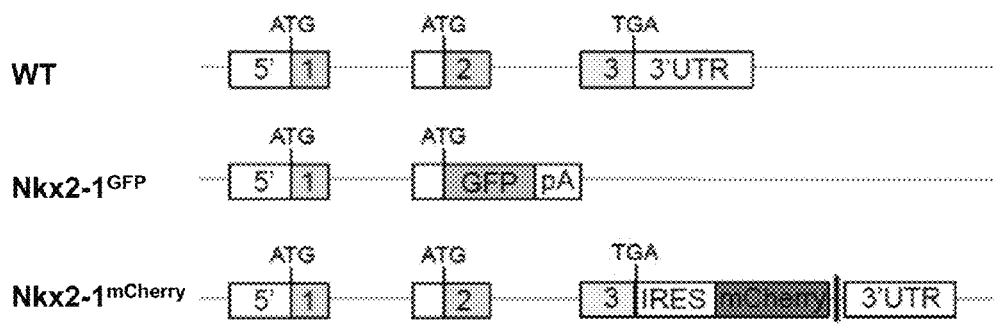
Figure 1D:
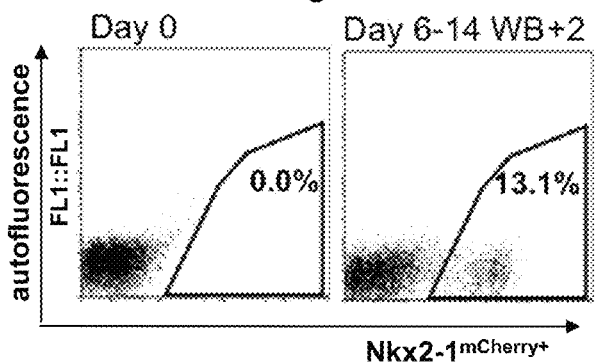
Figure 1E:
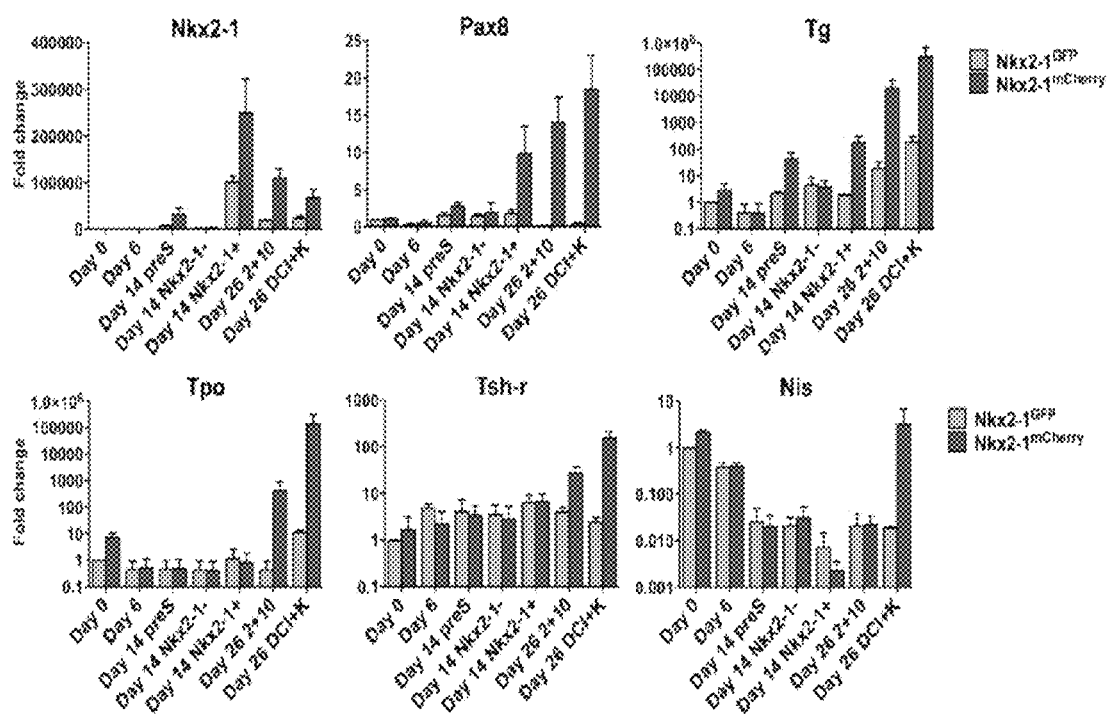
Figure 7B:
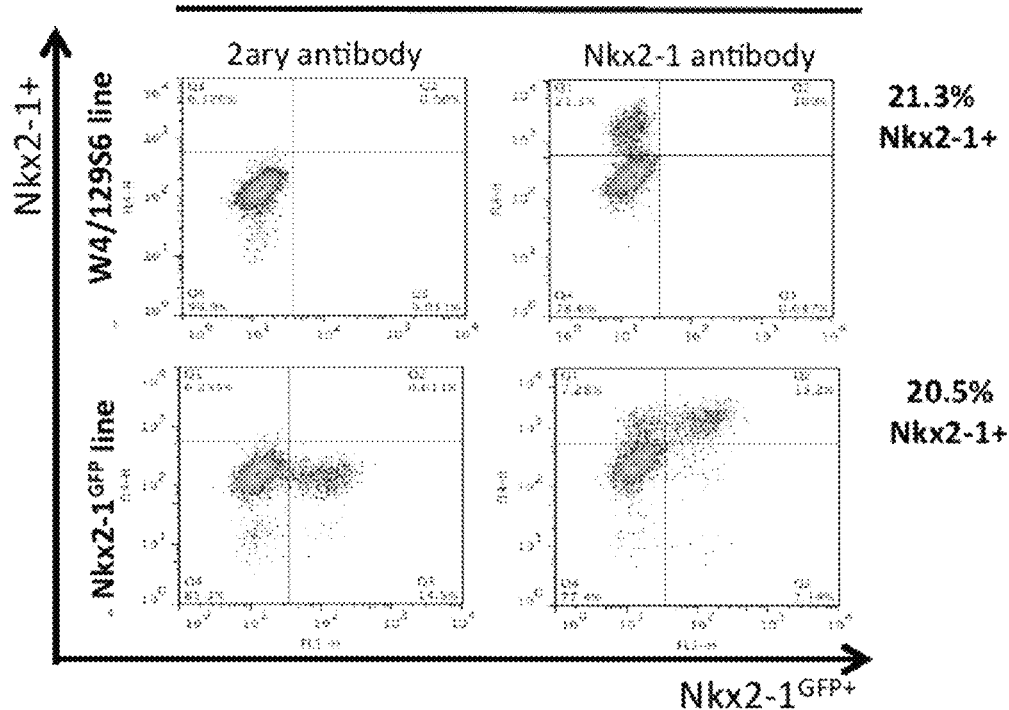
Figure 7C:
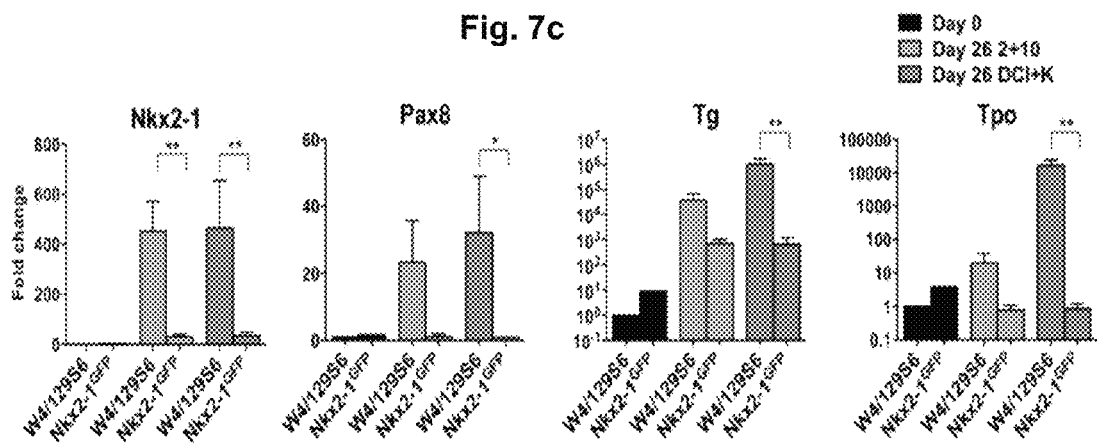

Nkx2-1 Haploinsufficiency Affects the Differentiation of Thyroid Epithelial Cells, but not the Efficiency of Initial Nkx2-1+ Endodermal Lineage Specification Because the Nkx2-1GFP knock-in reporter in our engineered ESCs replaced one allele's endogenous Nkx2-1 coding sequences, potentially creating haploinsufficiency (FIG. 1c), we sought to test the effects of Nkx2-1 gene dosage on thyroid differentiation in our in vitro model system. We compared the potentially haploinsufficient Nkx2-1GFP ESC line to a non-haploinsufficient Nkx2-1mCherry ESC line (Bilodeau et al., 2014), carrying an mCherry reporter targeted to the 3'-untranslated region of Nkx2-1 without disrupting the open reading frame of the gene (FIG. 1c). Hence comparison of Nkx2-1GFP versus Nkx2-1mChery lines allows direct comparison of the expression profiles of pure Nkx2-1+ progenitors with vs. without Nkx2-1 haploinsufficiency. The two lines were differentiated in parallel using the protocol shown in FIG. 1a (WB+2), and Nkx2-1GFP+ or Nkx2-1mCherry+ cells were sorted to purity on day 14 (FIG. 1d), at which time the expression of Nkx2-1 mRNA was approximately 50% lower in the haploinsufficient Nkx2-1GFP+ cells than in the non-haploinsufficient Nkx2-1 mCherry+ cells (FIG. 1e). Following outgrowth from equal numbers of sorted Nkx2-1+ cells from day 14 to 26, the expression of both early (Pax8) as well as all mature thyroid markers analyzed (Tg, Tsh-r, Nis, and Tpo) was diminished in Nkx2-1 haploinsufficient cells (FIG. 1e). In contrast we did not detect any difference in the rates of lineage specification of Nkx2-1+ endodermal cells on day 14, comparing haploinsufficient to normal ESC lines. Specifically the percentages and cell numbers of Nkx2-1+ cells arising from endodermal precursors by day 14 was similar when comparing the Nkx2-1GFP line to its parental syngeneic, non-haploinsufficient clone (FIGS. 7b and 7c) or to the Nkx2-1mCherry line (data not shown). We concluded that Nkx2-1 haploinsufficiency does not affect lineage specification of Nkx2-1+ endodermal cells, but does affect subsequent maturation of thyroid epithelial cells. This is supported by observations in mice and humans who have Nkx2-1 haploinsufficiency and hypothyroidism (Krude et al., 2002).

Figure 2A:
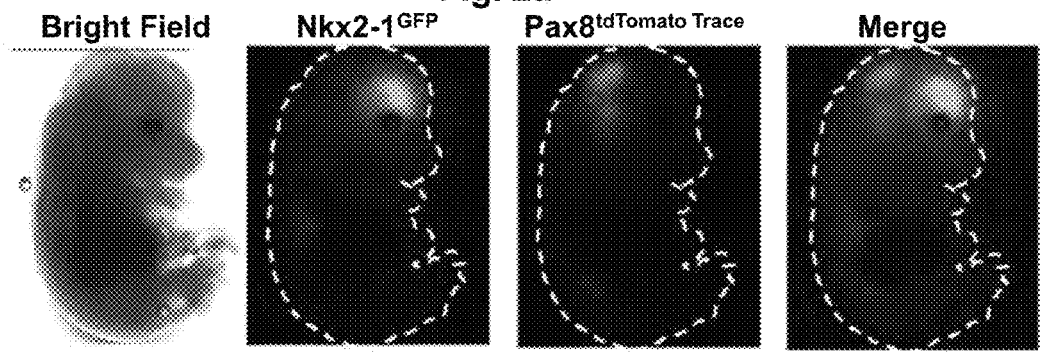
FIGS. 2a-2g show that thyroid lineage specification in developing embryos and in iPSC-derived endodermal precursors is restricted to cells co-expressing Nkx2-1 and Pax8.
Figure 2B:
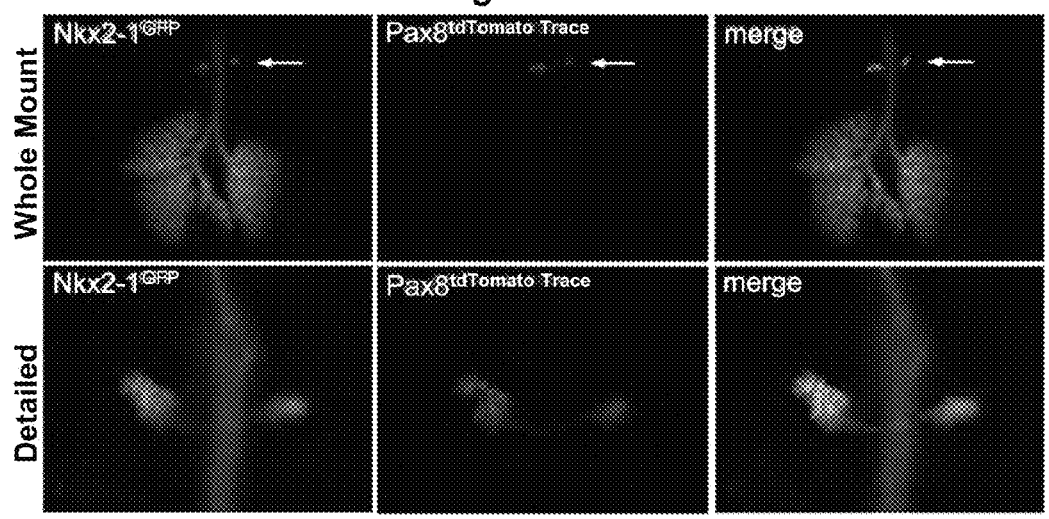
Figure 2C:
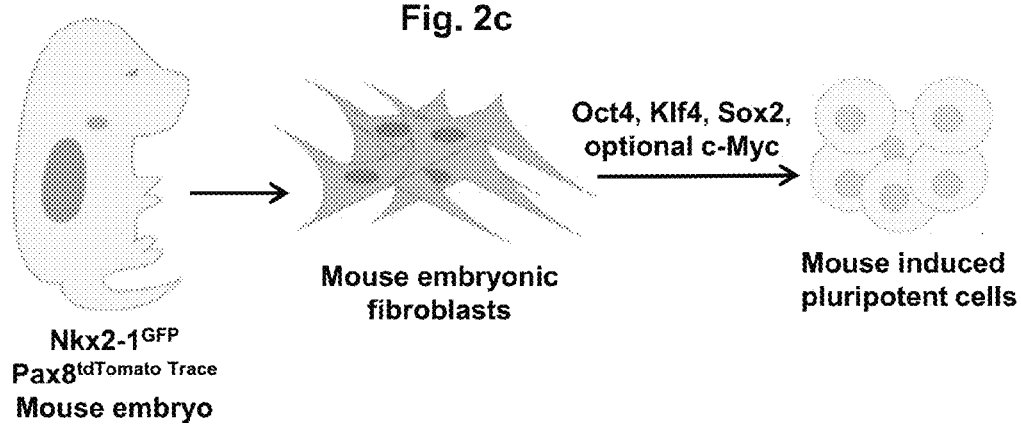
Figure 2D:
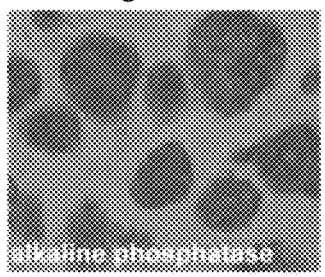
Figure 2E:
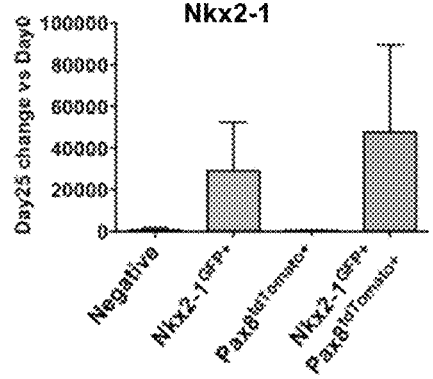
Figure 2F:
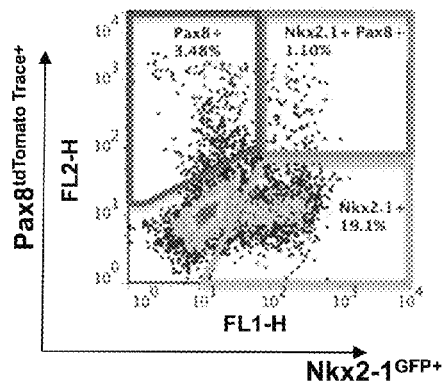
Figure 2G:
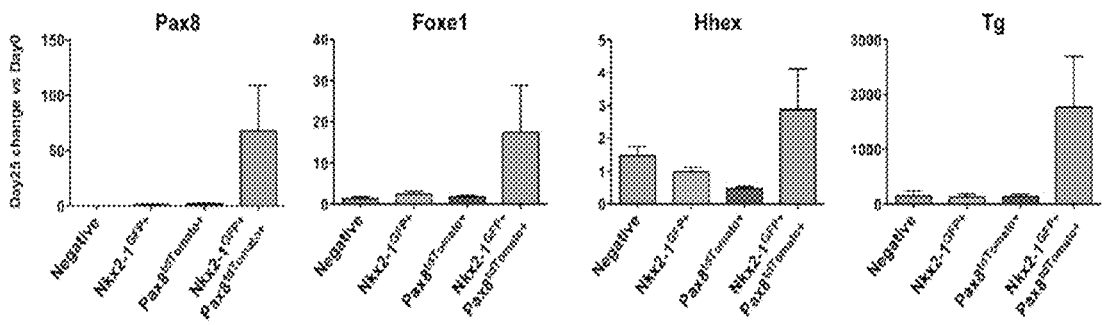
Figure 8A:
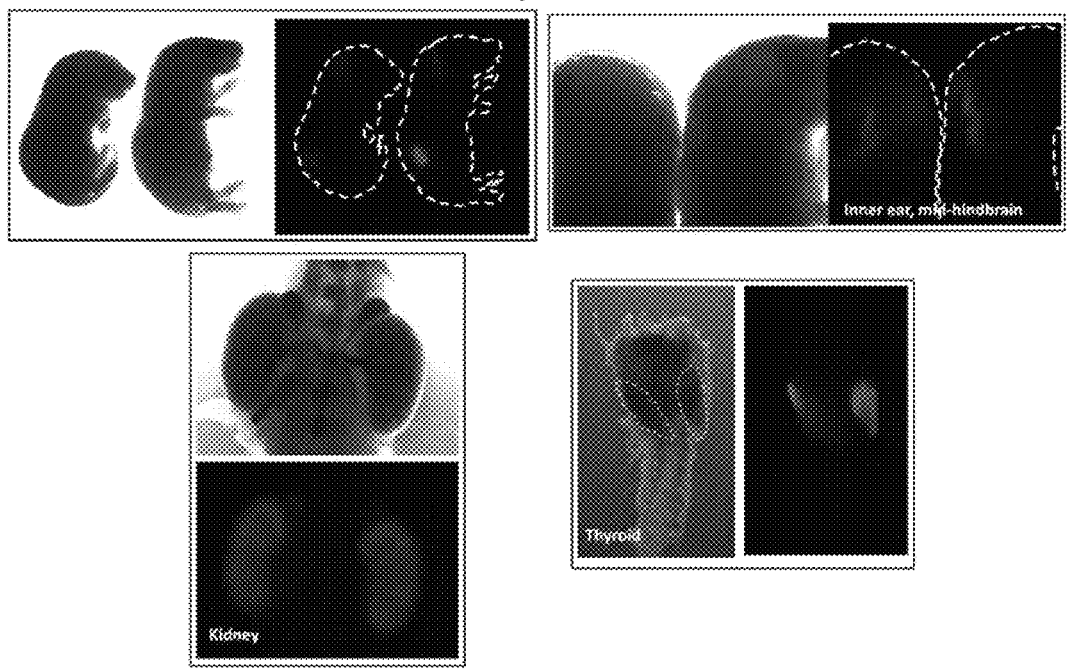
FIGS. 8a-8c shows that Pax8 is expressed in the thyroid, kidney, inner ear and mid-hindbrain in the postnatal mouse.
Figure 8B:
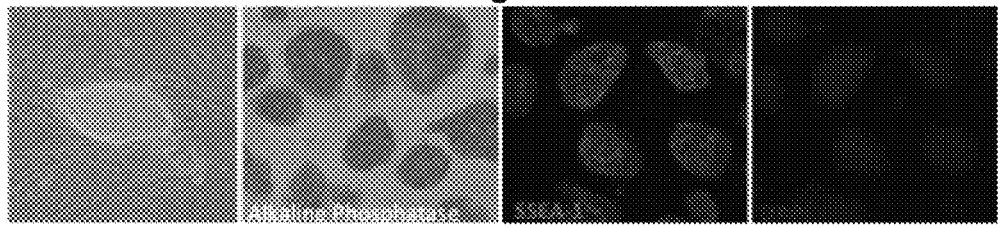
Figure 8C:
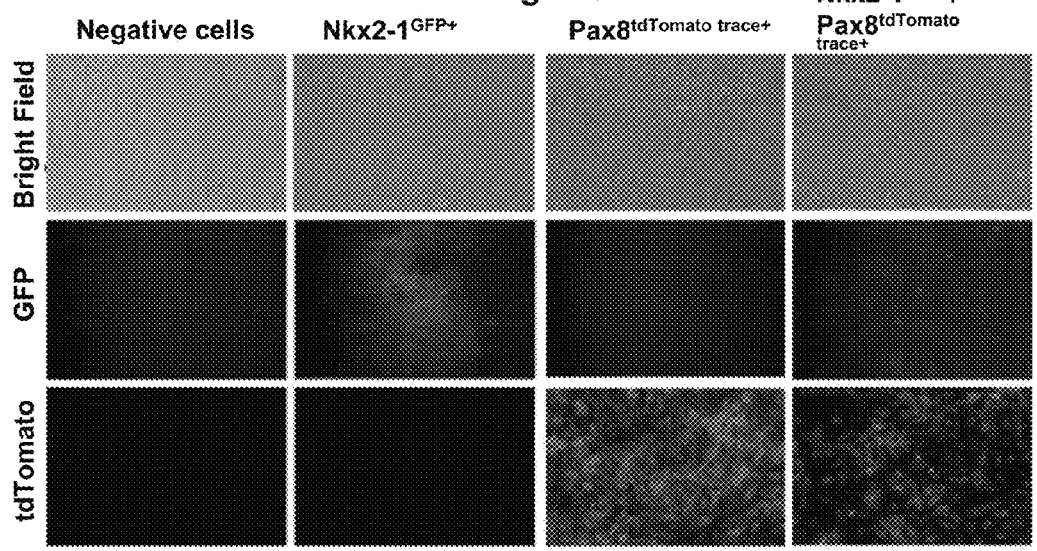

The Expression of Pax8 Distinguishes a Subpopulation within Nkx2-1+ Endodermal Cells with Thyroid Potential Having established a protocol able to produce putative thyroid cells, next we sought to determine whether thyroid and lung lineage specification were occurring in distinct endodermal Nkx2-1+ precursors as is thought to occur in vivo. Pax8 is a transcription factor that is co-expressed with Nkx2-1 only in thyroid epithelial cells, beginning at mouse embryonic day E8.5 in the foregut endoderm within the region of the prospective thyroid primordium (Fagman and Nilsson, 2010; Trueba et al., 2005). In contrast Pax8 is not known to be expressed at any developmental stage in lung epithelial cells. Hence, we developed a bifluorescent reporter system to track thyroid and non-thyroid fates in Nkx2-1+ cells by breeding mice engineered to contain the GFP reporter targeted to the Nkx2-1 locus (Nkx2-1GFP (Longmire et al., 2012), Cre recombinase targeted to the Pax8 locus (Pax8Cre (Bouchard et al., 2004)), and a conditional Rosa26 tdTomato reporter (lox-stop-lox-tdTomato). As expected, these mice (hereafter Nkx2-1GFP; Pax8tdTomato trace) co-expressed both GFP and tdTomato reporters only in the thyroid epithelium (FIGS. 2a and 2b), whereas GFP without tdTomato was expressed throughout the developing respiratory epithelium (FIGS. 2a and 2b). As previously reported, GFP was also expressed within developing ectoderm in the ventral forebrain (Longmire et al., 2012), and tdTomato without GFP was expressed in tissues known to express Pax8 but not Nkx2-1, including the kidney, hindbrain, midbrain, and inner ear (FIG. 8a and as previously published (Bouchard et al., 2004)). We generated 11 iPSC clones carrying Nkx2-1 GFP; Pax8tdTomato trace reporters by reprogramming mouse embryonic fibroblasts (MEFs) isolated from the bifluorescent mouse (FIGS. 2c, 2d and 8b) and differentiated 6 lines in vitro using our Wnt3a, BMP4, and FGF2 Nkx2-1 induction protocol (FIGS. 2e and 2f). By day 14 all clones exhibited induction of the Nkx2-1GFP reporter with kinetics and efficiency similar to our previous report (Longmire et al., 2012) and Pax8tdTomato trace+ cells represented approximately 4.9% (+/−4.7) of all Nkx2-1+ cells. Based on GFP and tdTomato expression, we sorted four distinguishable populations on day 14 (FIG. 2f) and replated each population separately for further differentiation in our protocol until day 25 (FIGS. 2e and 8c). Analysis of cells at the time of sorting (day 14) as well as after outgrowth until the full 25 days of differentiation of 3 independent clones revealed that only the sorted population that co-expressed both the GFP and tdTomato reporters on day 14 gave rise to cells expressing the constellation of 4 transcription factors (Parlato et al., 2004) that together uniquely identifies thyroid epithelia (Nkx2-1, Pax8, Foxe1, and Hhex) and the differentiated marker Tg (FIG. 2e). In contrast, this population was depleted of cells competent to express differentiated lung marker genes, Sftpc and Scgb1a1 (data not shown). In separate experiments using ESC lines that lack Pax8 reporters, we used FACS analyses of intracellular protein to verify that Pax8 protein is expressed in approximately 5% of Nkx2-1+ESC-derived cells (data not shown). We conclude that, as in the developing embryo, the thyroid lineage is specified in a distinct Nkx2-1+ endodermal progenitors and in this directed differentiation protocol thyroid primordial cells represent the minority (~5%) of the total Nkx2-1+ endodermal population generated from PSCs.

BMP and FGF signaling are necessary for thyroid lineage specification from mouse and *Xenopus* anterior foregut endoderm or ESC-derived definitive endoderm.

Figure 3A:
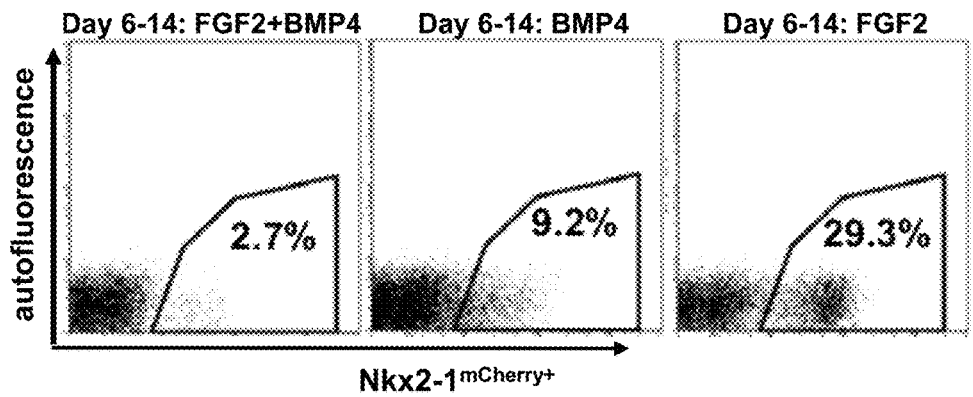
Figure 9:
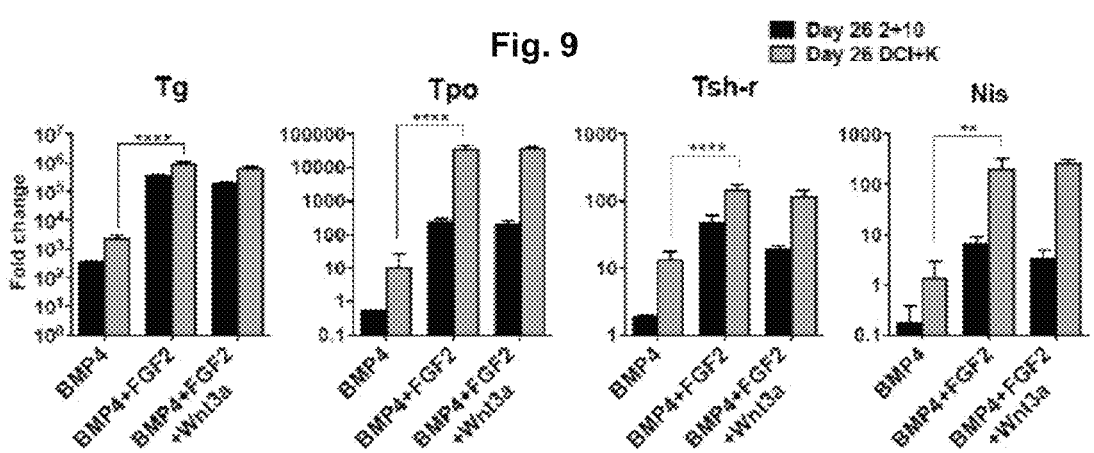
FIG. 9. Addition of Wnt3a does not alter thyroid lineage specification. mRNA expression of the indicated markers by real time RT-PCR at Day 26 of the differentiation of the Nkx2-1 mCherry ESC line, comparing the different specification media (Day 6 to Day 14) indicated. Bars indicate average fold change in gene expression [$2^{(-\Delta\Delta CT)}$] over ESCs±SD (n=3 biological replicates). 2-way ANOVA *p≤0.05, p≤0.01, *p≤0.001, ****p≤0.0001.

Having demonstrated that Pax8+/Nkx2-1+ thyroid progenitors were induced from PSC-derived endoderm by addition of just three factors, Wnt3a, BMP4, and FGF2 (WB+2) from day 6-14, we next sought to determine whether each pathway was necessary for thyroid lineage specification. In keeping with prior publications suggesting Wnt is not required for thyroid specification from endoderm in vivo (Goss et al., 2009), we found day 14 sorted Nkx2-1GFP+ cells (FIG. 7a) or sorted Nkx2-1mCherry+ cells (FIG. 9) derived with BMP4 and FGF2 induction media (day 6-14) in the absence of Wnt3a displayed undiminished subsequent expression of thyroid differentiation and maturation markers after outgrowth. Only the combination of BMP4 and FGF2 together induced robust thyroid lineage specification. While either BMP4 or FGF2 alone induced low numbers of Nkx2-1+ cells with little thyroid competence (FIG. 9), combinatorial use of BMP4 and FGF2 induced the highest percentage of thyroid competent Nkx2-1+ progenitors, as evidenced by subsequent robust expression of all early and mature thyroid markers including Pax8, Tsh-r, Tpo, or Nis (FIGS. 3a and 9). Consistent with these results, withdrawal of Wnt3a and/or addition of Wnt inhibitors Dkk1 or XAV-939 had no significant impact on the efficiency of lineage specification of Nkx2-1GFP+; Pax8tdTomato trace+ iPSC-derived cells by day 14, whereas there was a significant decrease in the percent yield of GFP+/tdTomato+ cells when either BMP or FGF2 was removed from the Nkx2-1 induction media (data not shown).

Figure 3B:
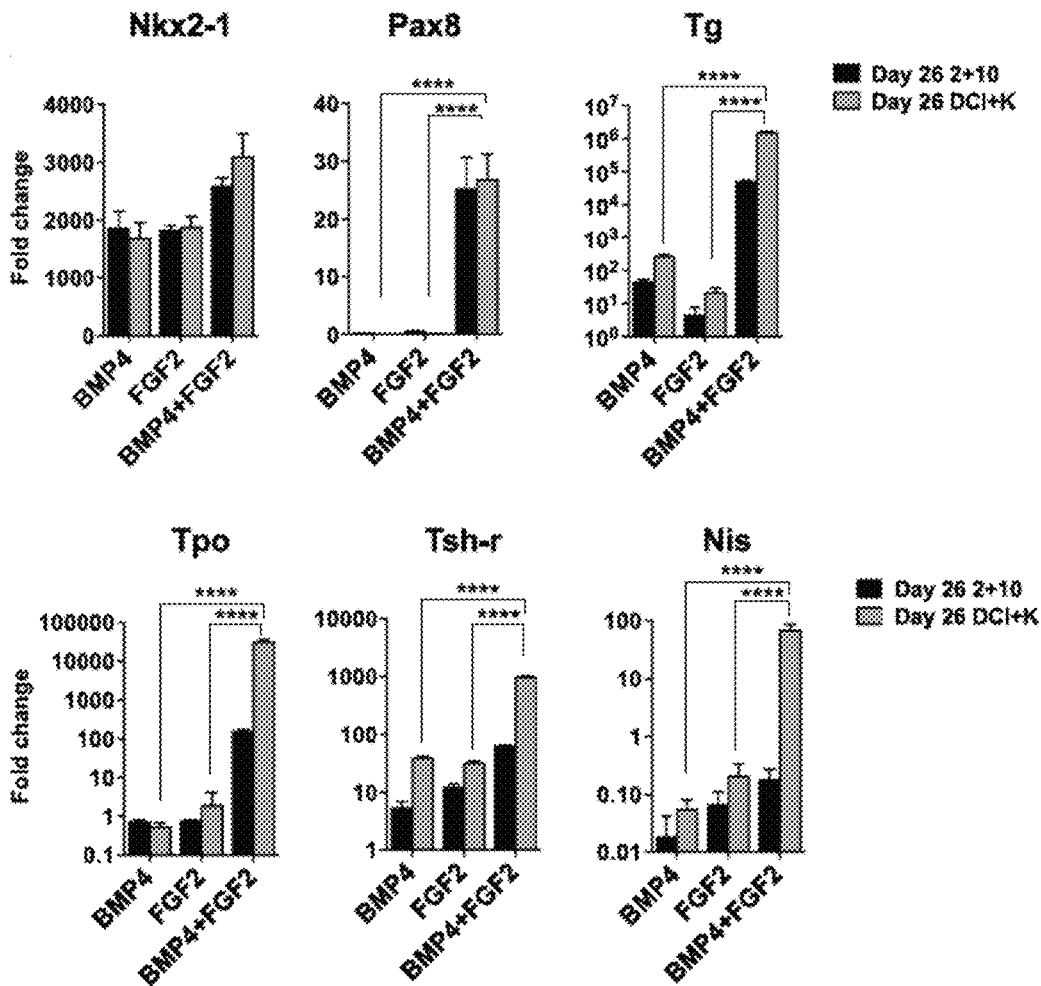

To determine which downstream BMP and FGF signaling cascades were required for induction of thyroid fate, we supplemented the BMP4+FGF2 media with specific inhibitors of either SMAD-dependent BMP signaling (Dorsomorphin), MEK 1/2-dependent FGF or BMP signaling (PD98059; hereafter PD), PI3 kinase (PI3K)-dependent FGF signaling (LY294002; hereafter LY), or p38-MAPK-dependent BMP signaling (SB203580). On day 14 of differentiation we found significantly reduced numbers and percentages of Nkx2-1 positive cells in conditions supplemented with Dorsomophin or LY, where either SMAD-signaling or PI3K-signaling, respectively, were inhibited (FIG. 3b). Furthermore, when the rare Nkx2-1+ cells that were induced in the presence of these inhibitors were sorted to purity on day 14 and cultured further to allow completion of the protocol (after removal of any inhibitors), the progeny of these rare Nkx2-1+ cells demonstrated significantly reduced capacity through day 26 to express thyroid markers, such as Tg and Tpo (FIG. 3d).

Figure 10A:
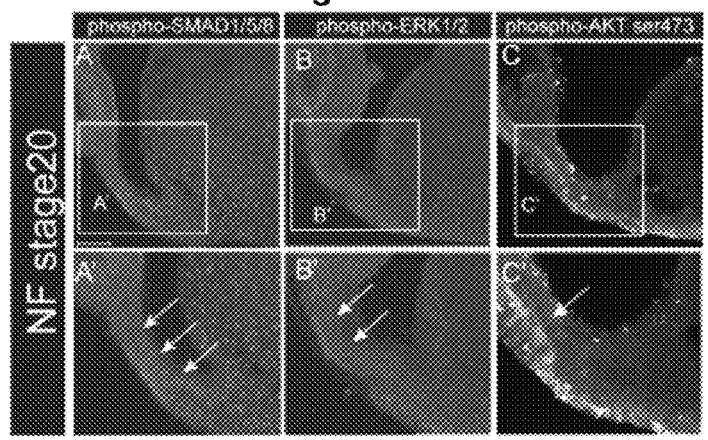

Taken together, our findings in the ESC/iPSC in vitro model systems suggested that during embryonic development canonical Wnt signaling is dispensable for thyroid lineage specification but combinatorial SMAD-dependent BMP signaling together with FGF signaling may be required. To test this hypothesis in primary cells of the developing embryo, we employed both the murine and *Xenopus* models of embryonic foregut endoderm development. First, in developing *Xenopus* embryos we found evidence in support of active BMP and FGF signaling by immunostaining embryos for nuclear phospho-SMAD1/5/8 as well as nuclear phospho-ERK1/2 proteins during early thyroid specification (FIG. 10a). Both pSMAD1/5/8 and pERK1/2 were present in the nuclei of anterior foregut epithelium prior to and during the evagination of Nkx2-1+ cells of the developing thyroid anlage as well as in the surrounding mesenchyme (FIG. 10a; stages NF20 and NF33). Because recent work has suggested that BMP signaling regulates the induction of endodermal Nkx2-1+ lung cell fate via pSMAD1/5/8 repressive binding to the proximal Sox2 promoter (Domyan et al., 2011), we also immunostained *Xenopus* foregut endoderm for Sox2 and found specific reduction of Sox2 staining localized to Nkx2-1+ thyroid progenitors around the time of lineage specification (FIG. 10a). These findings are consistent with prior work showing similar repression of Sox2 in developing thyroid anlage of the endodermal ventral pharyngeal floor at the time of thyroid lineage specification in the chick embryo (Ishii et al., 1998).

To assess whether FGF and BMP signaling are required for thyroid lineage specification, we incubated developing *Xenopus* embryos in small molecule inhibitors of SMAD-dependent BMP signaling (DMH-1) or FGF receptor signaling (SU5402) vs. vehicle control (DMSO), starting just after gastrulation (stage NF13) until stage NF20 (6-7 somite stage; ss). Embryos were then removed from the inhibitor, allowing embryos to develop until stage NF34 (36 ss; a time by which both thyroid and lung lineage specification are known to have occurred (Shifley et al., 2012). In situ hybridization for markers of pharyngeal endoderm and thyroid lineage specification, foxe1, nkx2-1, pax2, and hhex, revealed that loss of function of either BMP or FGF signaling abrogated induction of all four thyroid markers in the vast majority of embryos (FIG. 4a). In contrast, when embryos were incubated from stage NF13 through NF35 in inhibitors of canonical Wnt signaling (XAV939) or retinoic acid (RA) signaling (BMS493), we observed normal nkx2-1 induction in the developing thyroid primordium (FIG. 10b), indicating that Wnt and RA signaling at these developmental stages are dispensable for *Xenopus* thyroid specification.

To assess the stage dependence of these signaling requirements we varied the timing of BMP and FGF loss of function during foregut endoderm development. We observed that early inhibition of BMP or FGF signaling beginning at stage NF13 (analogous to mouse E7.5) blocked induction of nkx2-1, whereas inhibition beginning later (at stage NF20) did not, suggesting that the requirement for BMP and FGF signaling in thyroid lineage specification is restricted to a narrow developmental window between stages NF13-20 (FIG. 10b).

We next asked whether exogenous FGF2 and BMP4 were sufficient to induce thyroid development in *Xenopus* foregut endoderm (FIG. 4b). Foregut explants were micro-dissected at stage NF15, prior to thyroid specification and the mesoderm, which is known to express a number of FGF and BMP ligands, was removed. The foregut endoderm explants were then cultured in saline until stage NF35 either without growth factors or with a combination of FGF2 and BMP4 added to the medium. In situ hybridization revealed that while the control explants did not express any thyroid markers, explants incubated with FGF2 and BMP4 expressed nkx2-1, pax2, and hhex (FIG. 4b). We did not detect expression of sftpc in explants from sibling embryos (data not shown) suggesting that the nkx2-1 expression was thyroid and not respiratory epithelium. Thus, like in the ESC/iPSC in vitro model, FGF2 together with BMP4 was sufficient to induce thyroid fate in isolated *Xenopus* foregut endoderm (FIG. 4b).

To assess the requirement for SMAD-dependent BMP signaling in mouse thyroid lineage specification of primary foregut cells, we dissected developing foreguts from mouse embryos at 6-8 ss (~E8.0) prior to thyroid lineage specification. We incubated these foreguts for 2 or 3 days in explant cultures with or without the SMAD-inhibitor, DMH-1. Consistent with our findings in developing *Xenopus*, DMH-1 blocked induction of both Nkx2-1 and Pax8 in the region of the endodermal thyroid primordium (FIG. 4d). In addition DMH-1 caused a marked reduction in phosphorylation of SMAD1/5/8 compared to control vehicle when foreguts were analyzed by western blot (FIG. 4d, right panel). In the absence of DMH-1, thyroid lineage specification was easily detected by co-expression of Nkx2-1 and Pax8 by immunostaining, and phosphorylated SMAD1/5/8 was easily detected (FIG. 4d). Taken together these results from *Xenopus* and mouse embryo models extended our observations made in differentiating ESCs and iPSCs, confirming that FGF and BMP signaling are required for the specification of thyroid fate from developing endoderm (FIG. 4c).

Thyroid Stimulating Hormone and 3D Culture Promotes ESC-Derived Thyroid Follicular Maturation and Organoid Formation Having interrogated the growth factor-induced signals required for the induction of thyroid fate both in vivo and in vitro, next we focused on augmenting the maturation state of thyroid epithelial progenitors generated in our protocol from PSCs, employing the Nkx2-1mCherry ESC line. In contrast to thyroid lineage specification and early gland development, the expression of thyroid genes necessary for iodine metabolism, Nis and Tpo, is associated with later gland maturation (FIG. 5a) and has been demonstrated in vivo to require TSH receptor activation (Postiglione et al., 2002). Hence we tested the effect of adding TSH to each differentiation media at various developmental stages of our in vitro protocol, either during induction of Nkx2-1+ progenitors (day 9-12) or during outgrowth of sorted Nkx2-1+ cells following lineage specification (days 14-22). We found addition of TSH prior to lineage specification (day 9-12) had no detectable effect on the efficiency of thyroid lineage specification or the competence of thyroid cells to subsequently differentiate (data not shown). In contrast, we found addition of TSH after lineage specification had occurred (day 14-22) resulted in significant augmentation of Nis, Tsh-r, and Tpo expression (FIG. 11a), but no significant change in the expression of lineage markers Nkx2-1 and Pax8 (data not shown). An additional 3 days of culture maturation in the presence of TSH was accompanied by further augmentation of Nis and Tsh-r expression (FIG. 11a).

Figure 5A:
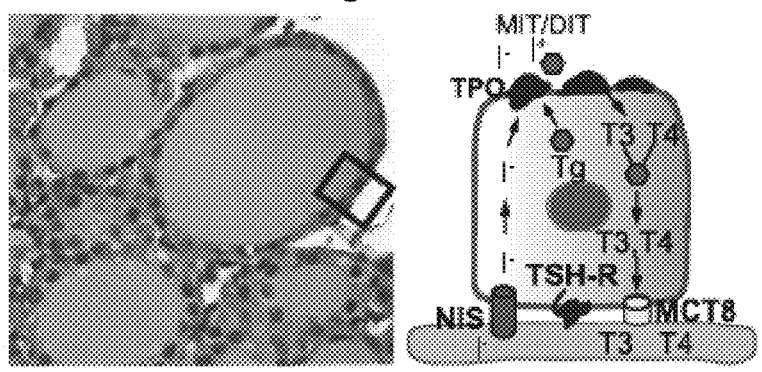
FIGS. 5a-5g show that in vitro development of ESC derived thyroid follicular cells by directed differentiation FIG. 5a. Representative image of Hematoxilin & Eosin (H&E) staining of a sectioned mouse thyroid tissue (left panel) and schematic of a thyroid follicular cell (right panel). Thyroid hormone (T4 and T3) synthesis is dependent on iodine uptake into the thyroid gland via the sodium/iodine symporter (NIS). Ultimately the iodine is integrated into tyrosines (MIT, DIT) present on the Thyroglobulin (Tg), which is then proteolyzed to release T4 and T3 from the follicular cell, in part, through the MCT8 transporter. Thyroid hormone synthesis in the follicular cell requires the presence of TSH, which acts through its receptor, TSH-R.
Figure 5B:
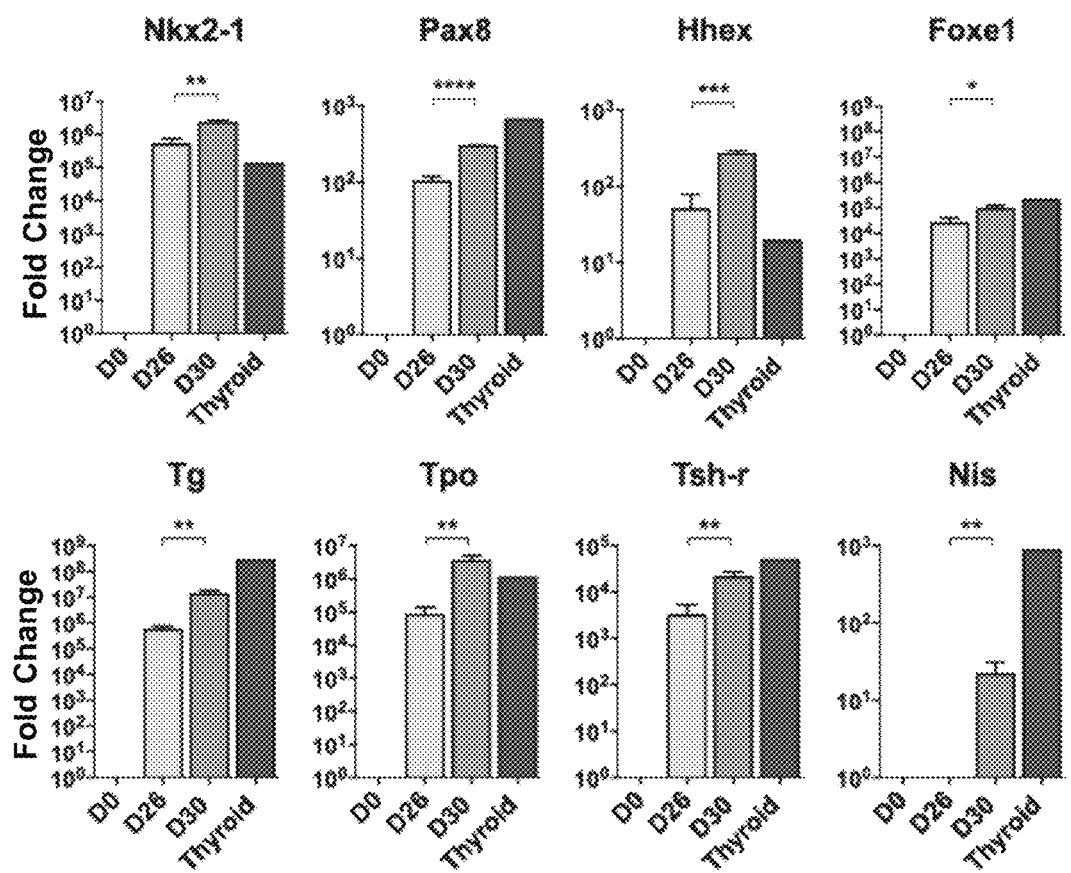
Figure 5C:
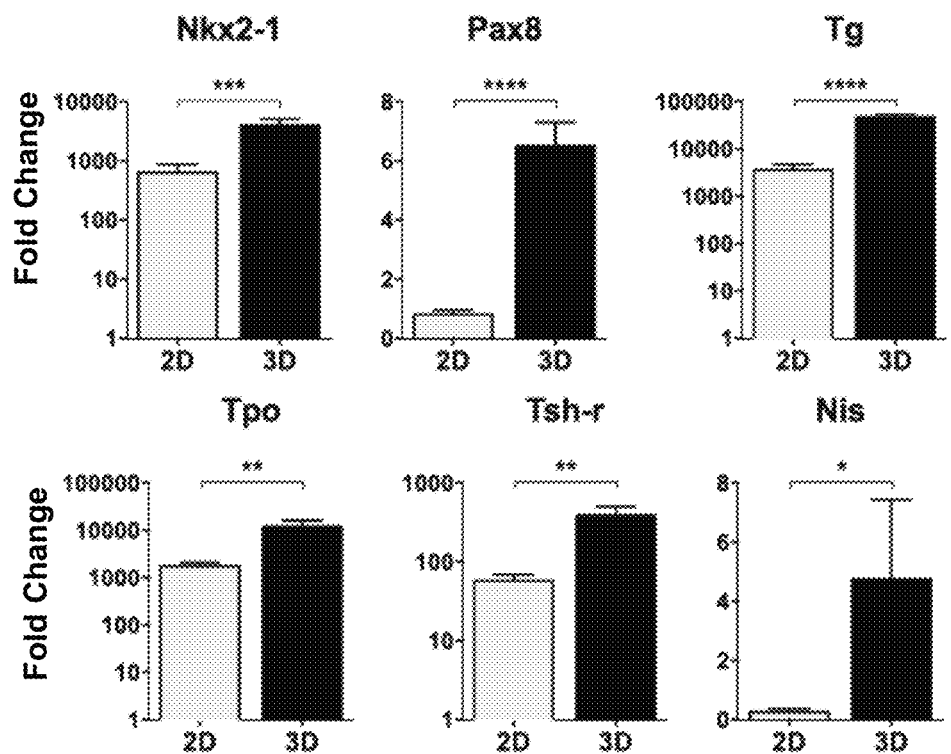

We previously published augmented thyroid gene expression in ESC-derived Nkx2-1+ cells when using a thyroid media containing IGF-1, insulin, transferrin, and selenium (Longmire et al., 2012). Therefore, in addition to TSH supplementation, we optimized our "thyroid outgrowth media," including these additives in our prior base media of FGF2+FGF10, starting immediately after replating sorted Nkx2-1+ cells on day 12 (FIG. 11b). For our final maturation stage following expansion of sorted cells in "thyroid outgrowth media" we sought to further optimize expression of the maturation markers, Nis and Tpo. Since we had observed evidence of augmentation of these maturation markers in response to either DCI+K (FIG. 1e) or in response to TSH, we tested the effect of combinations of each of these factors (FIG. 11c; day 22-26). We found that withdrawal of either cAMP or dexamethasone from the DCI+K cocktail adversely affected maturation (FIG. 5c), however substitution of TSH for cAMP in the DCI+K media retained maturation and resulted in the most robust augmentation of the thyroid maturation marker, Nis (FIG. 5c). Thus, the combination of dexamethasone and TSH was included in the final 4 days of maturation (day 26-30; FIG. 5b), resulting in the thyroid directed differentiation protocol summarized in FIG. 11b and achieving the derivation from ESCs of a population of cells expressing thyroid marker transcripts at levels similar to post-natal murine thyroid control tissue (FIG. 5b).

Figure 5D:
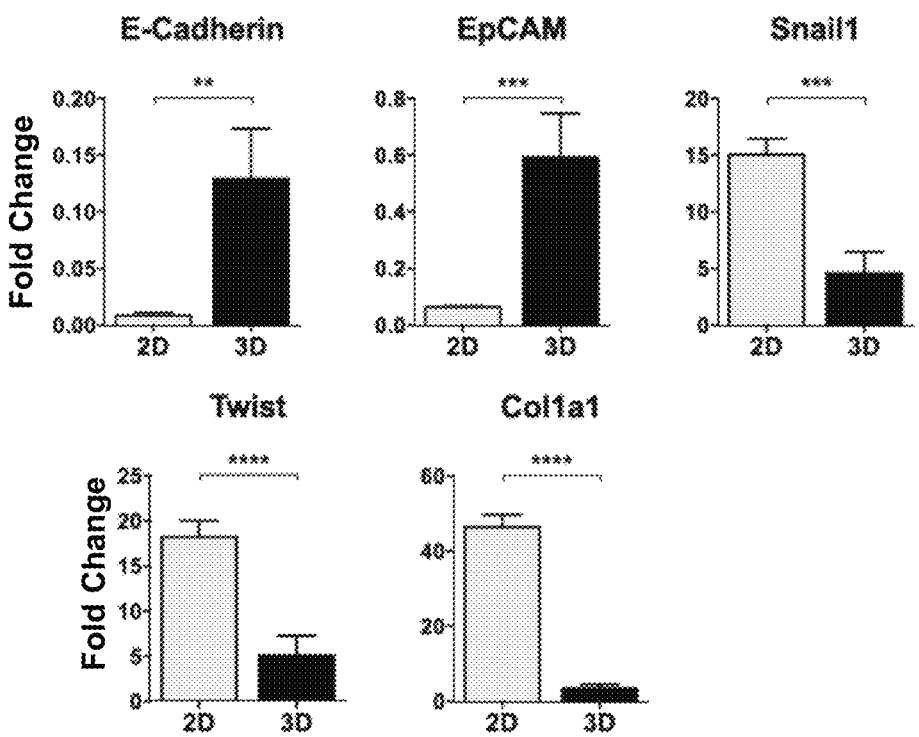
Figure 5E:
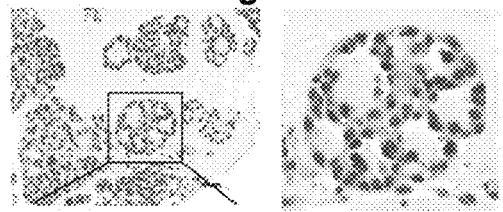
Figure 5F:
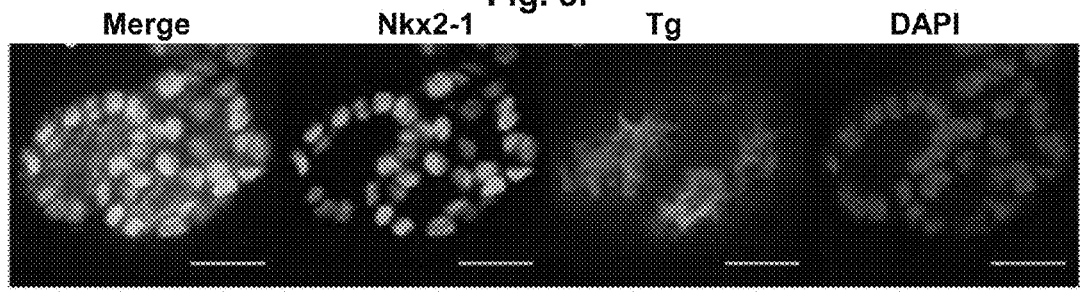
Figure 5G:
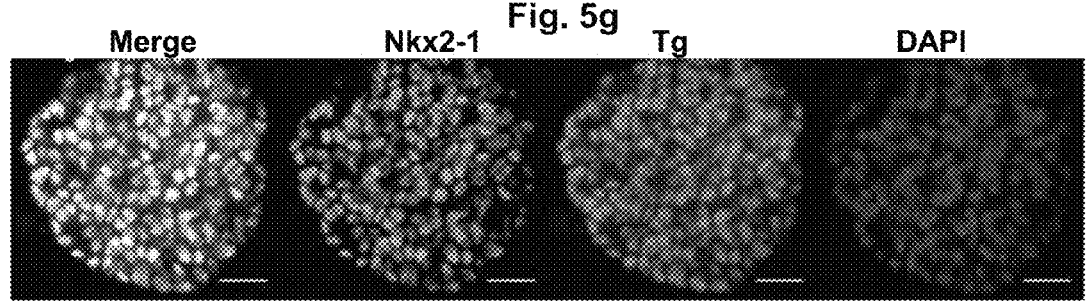
Figure 11D:
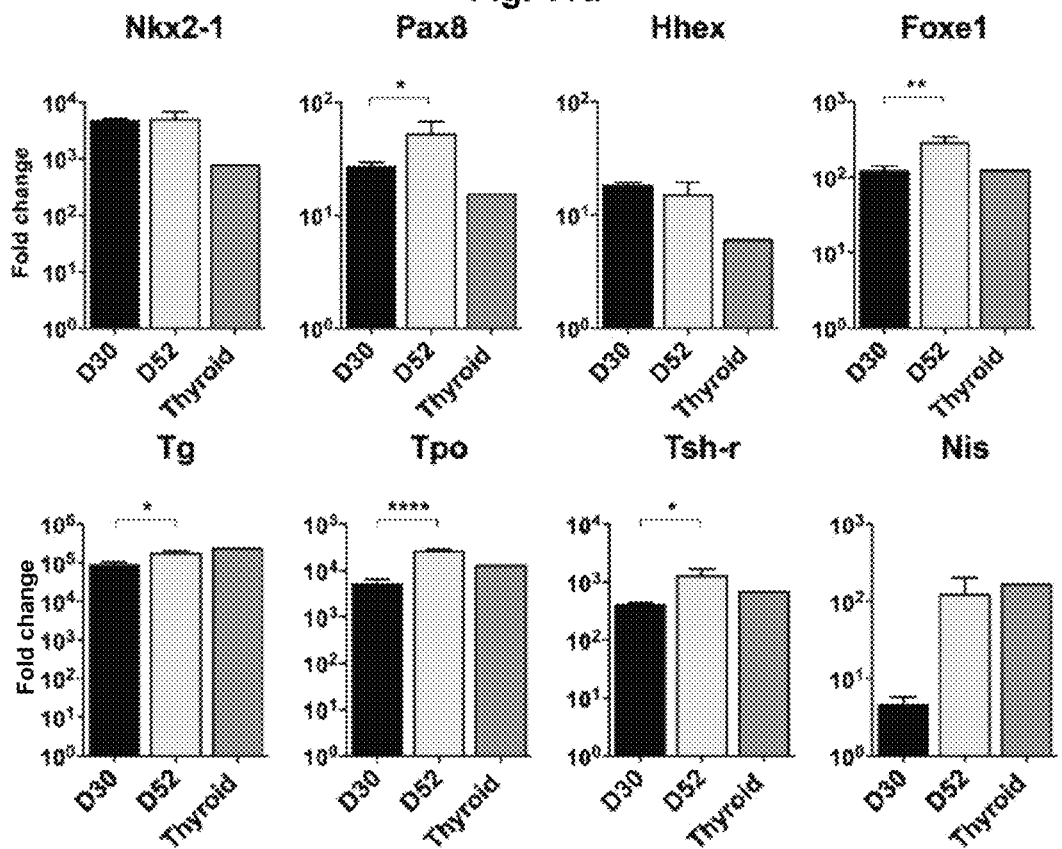

To facilitate thyroid follicular structural formation during outgrowth of ESC-derived Nkx2-1+ sorted cells, based on prior reports of Matrigel as a favorable thyroid culture substrate (Martin et al., 1993), we tested the effect of 3D culture in Matrigel during cell outgrowth (days 12-30; FIGS. 5c and 5d). Compared to 2D culture on gelatin-coated plastic, we found culture of purified Nkx2-1mCherry+ cells in 3D Matrigel conditions resulted in significantly augmented expression of thyroid genes by qPCR (Nkx2-1, Pax8, Tg, Tsh-r, Tpo, and Nis; FIG. 5c), improved maintenance of epithelial gene expression (augmented E-Cadherin and EpCam expression with reduced induction of mesenchymal markers, Snail1, Twist, and Col1a1; FIG. 5d), and facilitated the emergence of follicular-like clusters of cells (FIG. 5e). By day 30 we observed 130+/−17 follicular clusters emerging starting from 65,500 sorted Nkx2-1mCherry+ cells plated per well of a 24-well plate on day 12. By day 30 in culture, 50% of the progeny of the Nkx2-1mCherry+ sorted cell outgrowth expressed Pax8 protein by FACS, 46% expressed thyroglobulin, and 96% continued to express Nkx2-1 by either microscopy or FACS for the mCherry reporter (data not shown). Most importantly, phenotyping of the resulting clusters, hereafter referred to as organoids, revealed them to have the 3D structure and molecular phenotype typical of thyroid follicles, including formation of organized monolayered epithelia surrounding a lumen filled with thyroglobulin, and co-expression of nuclear Nkx2-1 and Pax8 protein (FIGS. 5f and 5g). These organoids could be further passaged and maintained in these culture conditions with stable or increased expression of Nkx2-1, Pax8, Tg, Nis, and Tpo until at least Day 52 in culture (FIG. 11d).

Figure 6A:
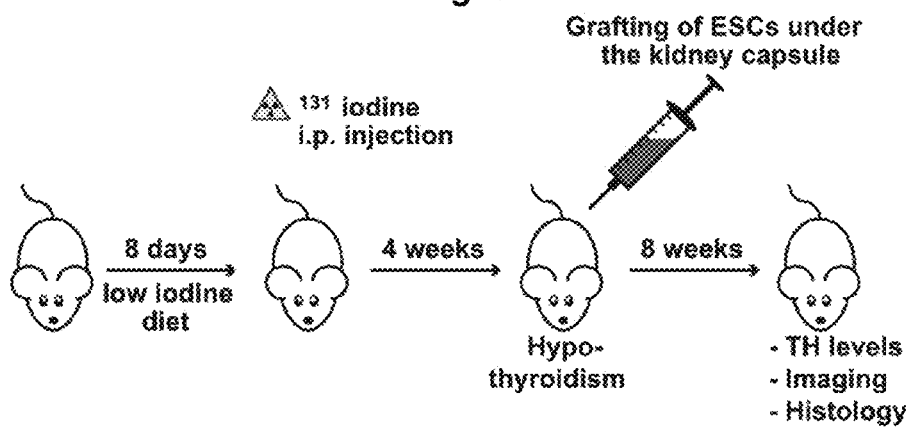
FIGS. 6a-6g show that in vivo function of transplanted ESC-derived putative thyroid follicles in hypothyroid mice FIG. 6a. Schematic summarizing ESCs transplantation under the left kidney capsule of hypothyroid syngeneic mice.
Figure 6B:
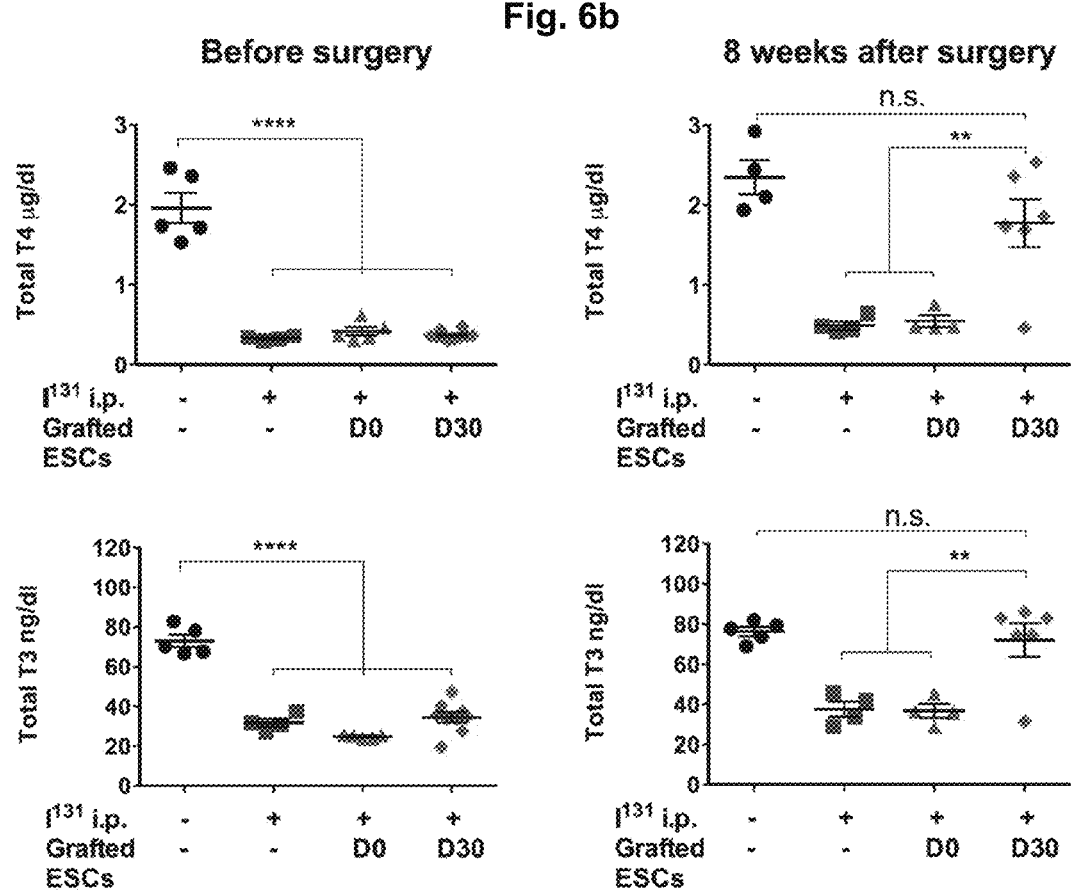

In Vivo Function of Purified ESC-Derived Thyroid Follicular Organoids Following Transplantation into Hypothyroid Mouse Recipients The defining functional characteristic of thyroid follicular epithelial cells is their capacity to synthesize and secrete thyroid hormones in vivo. Hence, we sought to test whether ESC-derived Nkx2-1mCherry+ thyroid progenitors sorted on day 12 of differentiation and further matured into organoids until day 30 could function in vivo after transplantation, and moreover whether these cells could rescue hypothyroid mice. Syngeneic mouse recipients underwent radioiodine ablation of their native thyroid tissue after 8 days of a low iodine diet in order to induce severe hypothyroidism, evident as significantly reduced circulating plasma T4 levels accompanied by markedly elevated circulating TSH levels (FIGS. 6a and 6b). Four weeks later, we prepared 1 positive control mouse group (n=5) that had not undergone radioiodine ablation, 1 negative control group that received sham surgery (hereafter "sham"; n=4), and 2 experimental recipient groups that received either undifferentiated (day 0 ESCs; hereafter "D0-ESCs" n=5) or differentiated ESCs that had been sorted on day 12 based on Nkx2-1mCherry+ expression and further differentiated until day 30 in our complete 3D protocol (hereafter D30-ESCs; n=10). Following ESC transplantation beneath the left kidney capsule of each mouse recipient we followed all recipient groups for at least 8 weeks post transplantation monitoring circulating T4, T3, and TSH levels, and we employed both MRI and SPECT/CT imaging to screen for in vivo graft growth and function (FIGS. 6 and 12).

Figure 6C:
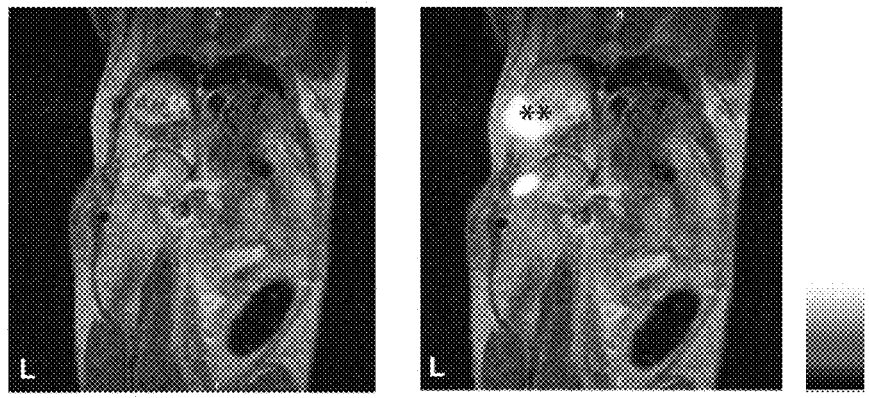
Figure 12A:
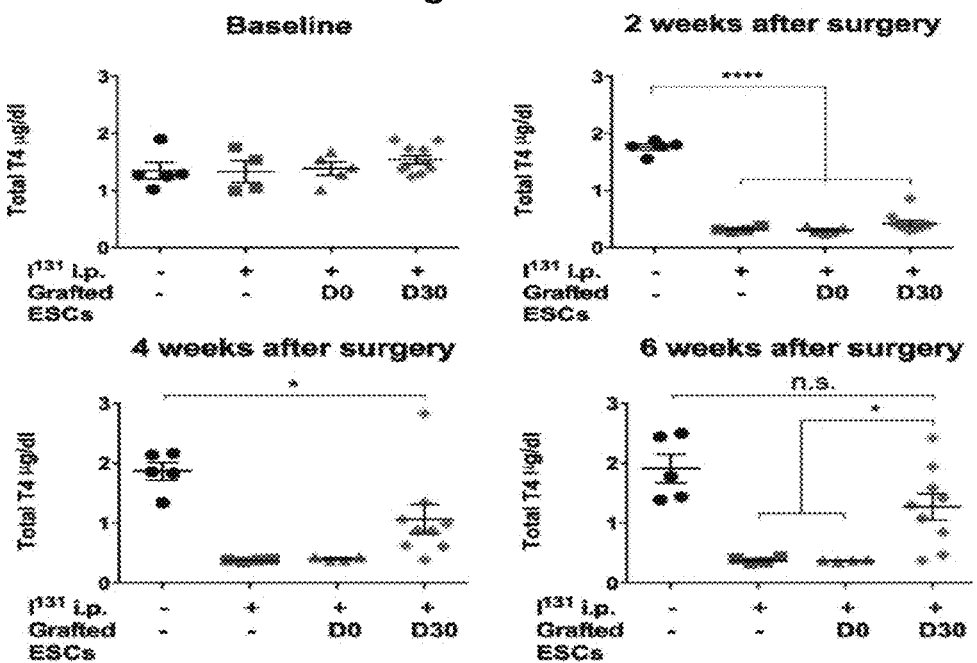
Figure 12D:
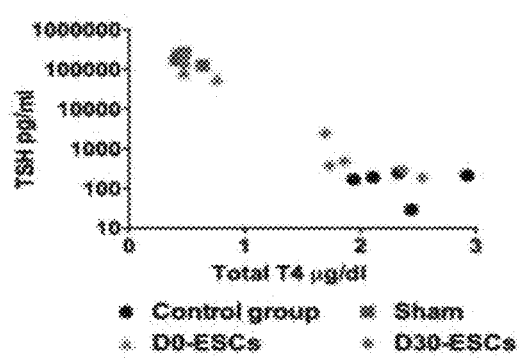
Figure 12E:
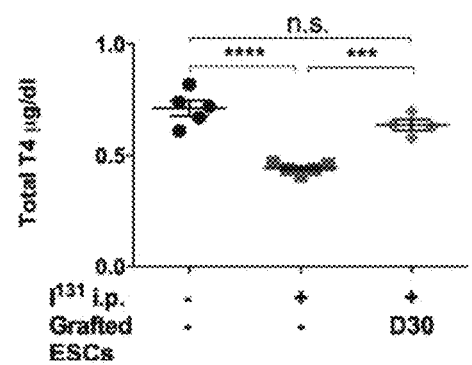
Figure 12F:
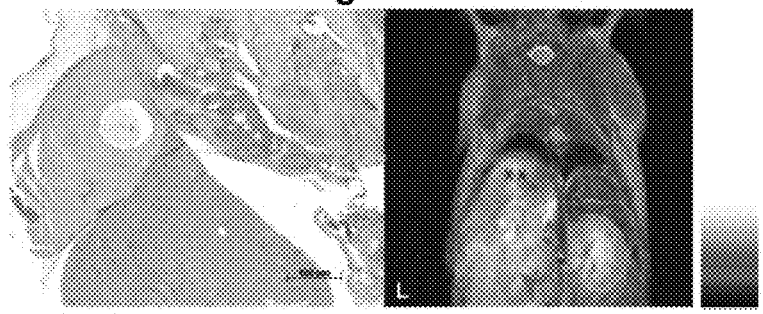

Starting 2-4 weeks post transplantation, recipients of D30-ESCs displayed significantly augmented circulating T4 and T3 levels that continued to increase over time until they approached normal levels by 8 weeks after transplantation (FIGS. 6b, 12a and 12c). Reconstitution of T4 levels was accompanied by significant amelioration of the previously elevated plasma TSH levels (FIGS. 6b, 12b and 12d), further emphasizing that physiologic rescue was occurring. In contrast, we observed no reconstitution of circulating thyroid hormone levels in either sham transplanted controls or recipients of D0-ESCs, excluding the possibility that either residual undifferentiated cells or re-growth of native thyroid tissue was responsible for the return of circulating T4 or the dampening of the TSH response. The kidney capsule grafts could be visualized by MRI in recipients of D30-ESCs and, as expected, in recipients of D0-ESCs who were predicted to form large teratomas based on the known pluripotency of undifferentiated D0-ESCs (FIGS. 6c and 12f).

Figure 6D:
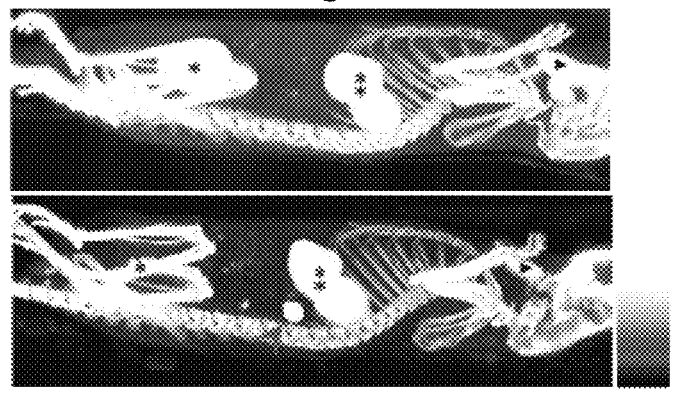
Figure 12G:
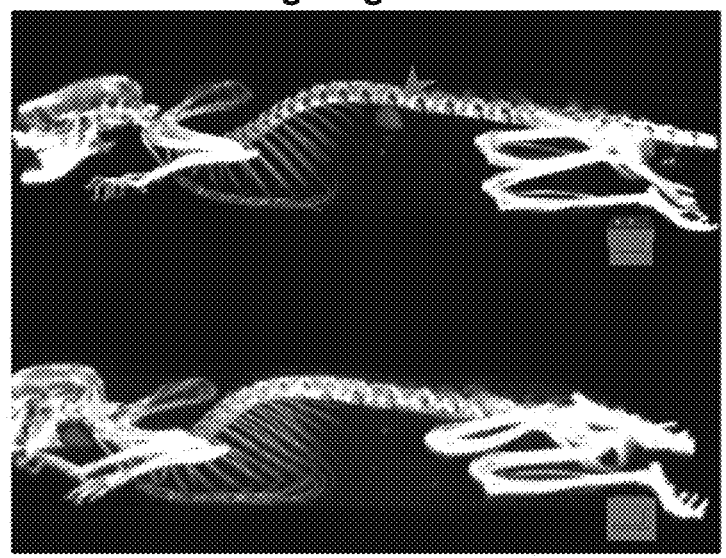

To further evaluate the function of the transplanted cells we incorporated imaging with sodium pertechtenate (Tc99M) and SPECT/CT co-registered with MRI imaging. Importantly the uptake of Tc99M into thyroid tissue is mediated by Nis allowing its visualization to be a surrogate for iodine uptake (Zuckier et al., 2004). In recipients of D30-ESCs we observed significant Tc99M uptake occurring in the region of the kidney capsule grafts (FIGS. 6c, 6d and 12g). We also observed low levels of Tc99M uptake in the large masses that derived from kidney capsule transplantation of D0-ESCs (FIG. 12f), but in no D0-ESC recipient was this signal accompanied by detectable return of circulating T4 levels. As expected, Tc99M uptake was not detected in the native thyroid tissue of any ablated recipient (FIGS. 6d and 12g), further suggesting that return of thyroid function in D30-ESC recipients was not due to regrowth of native thyroid tissue.

Figure 6E:
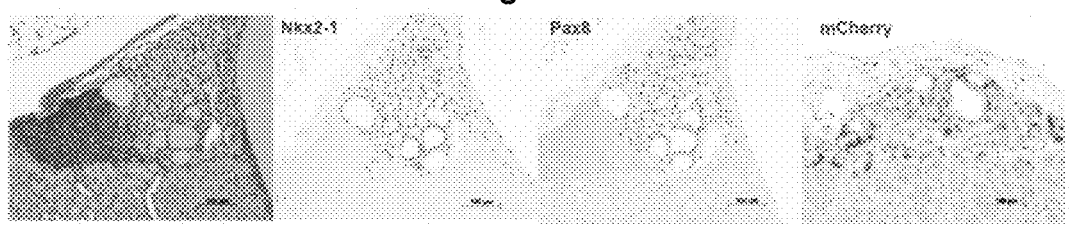
Figure 6F:
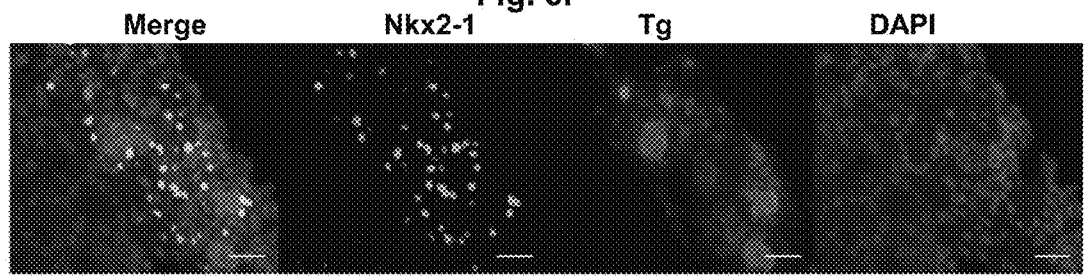
Figure 6G:
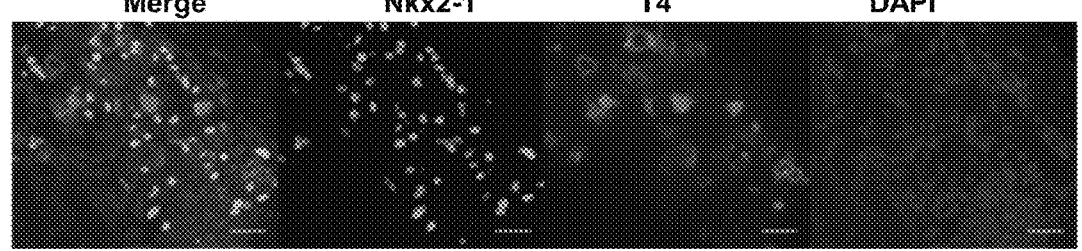

To confirm the presence of engrafted D30-ESCs in vivo we evaluated the histology of the renal lesions that had been visualized by MRI and SPECT (FIGS. 6e-6g). Recipients of D0-ESCs displayed large teratomas (FIG. 12f) without evidence of organized follicles and only rare, if any, cells expressed nuclear Nkx2-1 protein (data not shown). In contrast, recipients of D30-ESCs displayed persistent grafted cells beneath their kidney capsules organized into many follicular-like structures per high power field that were morphologically reminiscent of thyroid epithelial follicles (FIG. 6e). These structures consisted of mCherry+ epithelial cells expressing nuclear Nkx2-1 and Pax8 proteins by immunostaining, and these cells surrounded central lumens filled with colloid-like material that stained positively for Tg and T4 (FIGS. 6e-6g).

Finally, to assess whether the engrafted D30-ESCs functioned in a regulated fashion we exposed additional D30-ESC transplanted mice, negative sham controls, as well as positive normal controls (n=5 per group) to a high dose of exogenous T3 expected to fully suppress endogenous TSH and hence T4 production (data not shown). Indeed in all groups administration of T3 resulted in TSH suppression and abrogated T4 secretion. To further interrogate TSH responsiveness (FIG. 12e), we then injected each mouse with exogenous bovine TSH and three hours later observed an increase in circulating T4 in positive control mice as well as in recipients of D30-ESCs, but not in sham controls, consistent with the regulation of engrafted cells by TSH.

These results indicate that ESC-derived thyroid follicular epithelial cells prepared by directed differentiation in serum-free, feeder-free conditions exhibit in vivo functional potential, including the capacity to rescue hypothyroid mice who otherwise lack native functional thyroid tissue.

The references cited herein and throughout the specification are incorporated herein by reference.

REFERENCES

Abe, M., et al., (2002). Tooth-type specific expression of dHAND/Hand2: possible involvement in murine lower incisor morphogenesis. Cell Tissue Res 310, 201-212.

Abel, E. D., et al., (1999). Divergent roles for thyroid hormone receptor beta isoforms in the endocrine axis and auditory system. J Clin Invest 104, 291-300.

Ahnfelt-Ronne, J., et al., (2007). An improved method for three-dimensional reconstruction of protein expression patterns in intact mouse and chicken embryos and organs. The journal of histochemistry and cytochemistry: official journal of the Histochemistry Society 55, 925-930.

Antonica, F., et al. (2012). Generation of functional thyroid from embryonic stem cells. Nature 491, 66-71.

Arufe, M. C., et al., (2006). Directed differentiation of mouse embryonic stem cells into thyroid follicular cells. Endocrinology 147, 3007-3015.

Arufe, M. C., et al., (2009). Differentiation of murine embryonic stem cells to thyrocytes requires insulin and insulin-like growth factor-1. Biochem Biophys Res Commun 381, 264-270.

Bachiller, D., et al., E. M. (2003). The role of chordin/Bmp signals in mammalian pharyngeal development and DiGeorge syndrome. Development 130, 3567-3578.

Bilodeau, M., et al., (2014). Identification of a proximal progenitor population from murine fetal lungs with clonogenic and multilineage differentiation potential. Stem cell reports 3, 634-649.

Bouchard, M., et al., (2004). Tissue-specific expression of cre recombinase from the Pax8 locus. Genesis 38, 105-109.

Celli, G., et al., (1998). Soluble dominant-negative receptor uncovers essential roles for fibroblast growth factors in multi-organ induction and patterning. EMBO J 17, 1642-1655.

Cheng, X., et al. (2012). Self-renewing endodermal progenitor lines generated from human pluripotent stem cells. Cell Stem Cell 10, 371-384.

Domyan, E. T., et al., (2011). Signaling through BMP receptors promotes respiratory identity in the foregut via repression of Sox2. Development 138, 971-981.

Fagman, H., et al., (2007). The 22q11 deletion syndrome candidate gene Tbx1 determines thyroid size and positioning. Hum Mol Genet 16, 276-285.

Fagman, H., and Nilsson, M. (2010). Morphogenesis of the thyroid gland. Molecular and cellular endocrinology 323, 35-54.

Goss, A. M., et al. (2009). Wnt2/2b and beta-catenin signaling are necessary and sufficient to specify lung progenitors in the foregut. Dev Cell 17, 290-298.

Gouon-Evans, V., et al. (2006). BMP-4 is required for hepatic specification of mouse embryonic stem cell-derived definitive endoderm. NatBiotechnol 24, 1402-1411.

Hilfer, S. R., et al., (1968). Follicle formation in the embryonic chick thyroid. II. Reorganization after dissociation. Zeitschrift fur Zellforschung und mikroskopische Anatomie 92, 256-269.

Ishii, Y., et al. (1998). Region-specific expression of chicken Sox2 in the developing gut and lung epithelium: regulation by epithelial-mesenchymal interactions. Dev Dyn 213, 464-475.

Jiang, N., et al. (2010). Differentiation of E14 mouse embryonic stem cells into thyrocytes in vitro. Thyroid 20, 77-84.

Kameda, Y., et al. (2009). FRS2alpha is required for the separation, migration, and survival of pharyngeal-endoderm derived organs including thyroid, ultimobranchial body, parathyroid, and thymus. Dev Dyn 238, 503-513.

Krude, H., et al. (2002). Choreoathetosis, hypothyroidism, and pulmonary alterations due to human NKX2-1 haploinsufficiency. J Clin Invest 109, 475-480.

Lancaster, M. A., and Knoblich, J. A. (2014). Organogenesis in a dish: modeling development and disease using organoid technologies. Science 345, 1247125.

Lania, G., et al. (2009). Early thyroid development requires a Tbx1-Fgf8 pathway. Dev Biol 328, 109-117.

Longmire, T. A. et al. (2012). Efficient derivation of purified lung and thyroid progenitors from embryonic stem cells. Cell Stem Cell 10, 398-411.

Ma, R., et al. (2009). Thyrotropin-independent induction of thyroid endoderm from embryonic stem cells by activin A. Endocrinology 150, 1970-1975.

Ma, R., et al. (2015). Human embryonic stem cells form functional thyroid follicles. Thyroid.

Mallette, J. M., and Anthony, A. (1966). Growth in culture of trypsin dissociated thyroid cells from adult rats. Experimental cell research 41, 642-651.

Martin, A., et al. (1993). Preservation of functioning human thyroid organoids in the scid mouse: 1. System characterization. The Journal of clinical endocrinology and metabolism 77, 305-310.

McCracken, K. W., et al. (2014). Modelling human development and disease in pluripotent stem-cell-derived gastric organoids. Nature.

Murry, C. E., and Keller, G. (2008). Differentiation of embryonic stem cells to clinically relevant populations: lessons from embryonic development. Cell 132, 661-680.

Pagliuca, F. W., et al. (2014). Generation of functional human pancreatic beta cells in vitro. Cell 159, 428-439.

Parlato, R., et al. (2004). An integrated regulatory network controlling survival and migration in thyroid organogenesis. DevBiol 276, 464-475.

Petryk, A., et al. (2004). The mammalian twisted gastrulation gene functions in foregut and craniofacial development. Dev Biol 267, 374-386.

Postiglione, M. P., et al. (2002). Role of the thyroid-stimulating hormone receptor signaling in development and differentiation of the thyroid gland. Proc Natl Acad Sci USA 99, 15462-15467.

Rankin, S. A., et al. (2015). A Molecular atlas of *Xenopus* respiratory system development. Dev Dyn 244, 69-85.

Serls, A. E., et al. (2005). Different thresholds of fibroblast growth factors pattern the ventral foregut into liver and lung. Development 132, 35-47.

Shifley, E. T., et al. (2012). Prolonged FGF signaling is necessary for lung and liver induction in *Xenopus*. BMC Dev Biol 12, 27.

Sommer, C. A., et al. (2009). Induced pluripotent stem cell generation using a single lentiviral stem cell cassette. In Stem Cells, pp. 543-549.

Trueba, S. S., et al. (2005). PAX8, TITF1, and FOXE1 gene expression patterns during human development: new insights into human thyroid development and thyroid dysgenesis-associated malformations. The Journal of clinical endocrinology and metabolism 90, 455-462.

Vitelli, F., et al. (2002). A genetic link between Tbx1 and fibroblast growth factor signaling. Development 129, 4605-4611.

Wendl, T et al. (2007). Early developmental specification of the thyroid gland depends on han-expressing surrounding tissue and on FGF signals. Development 134, 2871-2879.

Zuckier, L. S., et al. (2004). Kinetics of perrhenate uptake and comparative biodistribution of perrhenate, pertechnetate, and iodide by NaI symporter-expressing tissues in vivo. Journal of nuclear medicine: official publication, Society of Nuclear Medicine 45, 500-507

Table 2

Ingenuity Pathway Analysis of 1267 transcripts differentially expressed at day 14 between GFP positive vs GFP negative sorted populations; GEO accession number GSE35063: see sheet 2 for list of gene names and probes. Pathways reaching statistical significance are shown in first column.

| Ingenuity Canonical Pathways | −log(p-value) | Ratio | Molecules |
|---|---|---|---|
| Molecular Mechanisms of Cancer | 4.2E00 | 1.01E−01 | MAPK3, TFDP1, ARHGEF3, WNT5A, NOTCH1, PRKD1, CAMK2D, BMP5, BMPR1B, FZD6, ADCY2, FOS, GLI1, CCNE1, SHC1, JAK3, BMP7, ADCY8, MAPK10, ARHGEF6, PLCB1, PRKDC, MAP3K5, SMAD3, FYN, CDKN1B, GNAZ, IRS1, RHOB, FZD2, RHOU, JUN, FZD5, GAB2, LEF1, CTNNA2, CCND3, BMP4 |
| Biosynthesis of Steroids | 3.99E00 | 6.45E−02 | FDPS, FDFT1, SQLE, IDI1, DHCR7, HMGCR, LSS, MVD |
| Axonal Guidance Signaling | 3.52E00 | 9.32E−02 | MAPK3, ADAM15, TUBB3, WNT5A, EPHA2, PRKD1, HERC2, EPHA3, FIGF, EIF4E, BMP5, FZD6, GNG3, UNC5D, IGF1, GLI1, SHC1, BMP7, LINGO1, PLXNC1, ARHGEF6, SEMA4F, GLI3, PLCB1, SLIT2, CXCL12, ITGA4, FYN, GNAZ, PLXND1, FZD2, SEMA4D, FZD5, EPHA4, EPHB2, NTF3, UNC5B, EPHA7, TUBB2B, BMP4 |
| Role of Osteoblasts, Osteoclasts and Chondrocytes in Rheumatoid Arthritis | 3.41E00 | 1.09E−01 | MAPK3, WNT5A, DKK3, COL1A1, CAMK4, BMP5, BMPR1B, FZD6, DKK1, IGF1, FOS, RUNX2, BMP7, MAPK10, DKK2, MAP3K5, ADAMTS5, DLX5, FZD2, SFRP2, JUN, FZD5, CHUK, LEF1, GSN, BMP4 |

-continued

| Ingenuity Canonical Pathways | −log(p-value) | Ratio | Molecules |
|---|---|---|---|
| 4-1BB Signaling in T Lymphocytes | 2.96E00 | 2.06E−01 | MAPK3, MAP3K5, JUN, CHUK, MAP3K1, IKBKAP, MAPK10 |
| cAMP-mediated signaling | 2.93E00 | 1.11E−01 | ADRB2, MAPK3, PTGER3, AGTR2, CAMK1D, PDE8A, CAMK2D, HTR1B, PDE9A, DUSP9, CAMK4, PDE7B, PDE4D, ADORA2A, ADCY2, RGS7, S1PR3, DUSP1, PDE11A, ADORA1, PDE3A, P2RY14, PTH1R, ADCY8 |
| Amyotrophic Lateral Sclerosis Signaling | 2.82E00 | 1.19E−01 | GRIA1, RNF19A, GRIK3, NEFL, NOS1, FIGF, GRIK1, CACNA1A, GRIK2, GRIA3, IGF1, GRIA4, CACNA1C, GRIN2C |
| Type II Diabetes Mellitus Signaling | 2.58E00 | 9.38E−02 | SMPD2, MAPK3, ACSL5, MAP3K5, PRKD1, IRS2, SLC27A1, IRS1, SOCS3, IRS4, MAP3K1, CHUK, SMPD3, SOCS2, MAPK10 |
| Prolactin Signaling | 2.51E00 | 1.38E−01 | IRF1, IRS1, MAPK3, NR3C1, SOCS3, FOS, JUN, PRKD1, SHC1, FYN, SOCS2 |
| Factors Promoting Cardiogenesis in Vertebrates | 2.36E00 | 1.26E−01 | FZD6, DKK1, CDC6, FZD2, PRKD1, FZD5, CCNE1, LEF1, BMP7, BMP5, BMP4, BMPR1B |
| Glioblastoma Multiforme Signaling | 2.32E00 | 1.04E−01 | MAPK3, PLCB1, WNT5A, PLCL1, NF2, CDKN1B, EGFR, PDGFRA, FZD6, RHOB, FZD2, IGF1, RHOU, CCNE1, FZD5, SHC1, LEF1 |
| Calcium Signaling | 2.31E00 | 9.31E−02 | GRIA1, MAPK3, RYR2, CAMK1D, CAMK2D, ATP2B4, MEF2A, CAMK4, PNCK, HDAC9, GRIK1, GRIA3, TRPC3, TRPC4, GRIA4, MYH9, TRPC6, TRPC5, GRIN2C |
| Neuropathic Pain Signaling In Dorsal Horn Neurons | 2.29E00 | 1.2E−01 | GRIA1, MAPK3, PLCB1, CAMK1D, PRKD1, PLCL1, CAMK2D, CAMK4, GRIA3, FOS, KCNQ3, GRIA4, GRIN2C |
| Cholecystokinin/Gastrin-mediated Signaling | 2.25E00 | 1.23E−01 | MAPK3, PLCB1, PRKD1, MEF2A, EGFR, RHOB, FOS, RHOU, JUN, EPHA4, SST, SHC1, MAPK10 |
| Agrin Interactions at Neuromuscular Junction | 2.25E00 | 1.45E−01 | ARHGEF6, MAPK3, ITGA6, JUN, ERBB4, ITGA4, DAG1, LAMC1, EGFR, MAPK10 |
| Aminosugars Metabolism | 2.24E00 | 8.53E−02 | GNE, PDE11A, PDE8A, PDE3A, NPL, RENBP, PDE9A, GNPNAT1, UAP1, PDE7B, PDE4D |
| Thrombin Signaling | 2.16E00 | 9.76E−02 | ARHGEF6, MAPK3, ARHGEF3, PLCB1, CAMK1D, PRKD1, GATA3, PLCL1, GATA2, CAMK2D, GNAZ, EGFR, CAMK4, ADCY2, GNG3, RHOB, RHOU, SHC1, ARHGEF9, ADCY8 |
| Basal Cell Carcinoma Signaling | 2.16E00 | 1.37E−01 | FZD6, FZD2, GLI3, WNT5A, GLI1, FZD5, LEF1, BMP7, BMP5, BMP4 |
| Cardiac Hypertrophy Signaling | 1.98E00 | 8.98E−02 | ADRB2, MAPK3, PLCB1, EIF2B3, MAP3K5, PLCL1, GNAZ, MEF2A, CAMK4, EIF4E, ADCY2, GNG3, IRS1, RHOB, CACNA1A, IGF1, RHOU, JUN, MAP3K1, ADCY8, CACNA1C, MAPK10 |
| CREB Signaling in Neurons | 1.95E00 | 8.91E−02 | GRIA1, GRIK3, MAPK3, PLCB1, PRKD1, PLCL1, CAMK2D, GNAZ, CAMK4, GRIK1, ADCY2, GNG3, GRIA3, GRIK2, GRIA4, SHC1, ADCY8, GRIN2C |
| IGF-1 Signaling | 1.92E00 | 1.12E−01 | IRS1, NOV, MAPK3, IGF1, SOCS3, FOS, JUN, GRB10, IRS2, SHC1, SOCS2, CYR61 |
| IL-17A Signaling in Gastric Cells | 1.88E00 | 2E−01 | MAPK3, FOS, JUN, EGFR, MAPK10 |
| Role of JAK2 in Hormone-like Cytokine Signaling | 1.84E00 | 1.62E−01 | IRS1, SOCS3, IRS4, IRS2, SHC1, SOCS2 |
| Growth Hormone Signaling | 1.79E00 | 1.2E−01 | IRS1, MAPK3, IGF1, SOCS3, FOS, A2M, PRKD1, RPS6KA2, SOCS2 |
| Glutamate Receptor Signaling | 1.78E00 | 1.16E−01 | GRIA1, GRIK3, GRIA3, GRIK2, GRIA4, CAMK4, GRIN2C, GRIK1 |
| Acute Phase Response Signaling | 1.76E00 | 9.55E−02 | MAPK3, A2M, MAP3K5, CRABP1, OSMR, CRABP2, SOCS3, NR3C1, FOS, CP, JUN, CHUK, MAP3K1, SHC1, SOCS2, TF, SAA4 |
| Synaptic Long Term Potentiation | 1.76E00 | 1.05E−01 | GRIA1, GRIA3, MAPK3, PPP1R3D, PLCB1, PRKD1, GRIA4, CAMK2D, CAMK4, ADCY8, CACNA1C, GRIN2C |
| Cardiac β-adrenergic Signaling | 1.75E00 | 9.27E−02 | RYR2, PPP1R3D, PDE8A, PDE9A, PDE7B, PDE4D, ADCY2, GNG3, CACNA1A, PDE11A, PDE3A, ADRBK2, CACNA1C, ADCY8 |
| Cardiomyocyte Differentiation via BMP Receptors | 1.75E00 | 2E−01 | BMP7, BMP5, BMP4, BMPR1B |
| Endoplasmic Reticulum Stress Pathway | 1.75E00 | 2.22E−01 | ERN1, MAP3K5, XBP1, TAOK3 |

| Ingenuity Canonical Pathways | −log(p-value) | Ratio | Molecules |
|---|---|---|---|
| Wnt/β-catenin Signaling | 1.74E00 | 9.88E−02 | DKK2, WNT5A, CDH3, DKK3, TLE1, FZD6, DKK1, FZD2, SFRP2, NR5A2, JUN, FZD5, SOX6, LEF1, CD44, RARG |
| PI3K Signaling in B Lymphocytes | 1.7E00 | 9.79E−02 | MAPK3, PLCB1, PLCL1, IRS2, FYN, CAMK2D, CAMK4, IRS1, FOS, JUN, IRS4, CHUK, IL4R, CARD10 |
| Notch Signaling | 1.67E00 | 1.4E−01 | NOTCH1, NOTCH2, MAML2, DTX3, HEY1, HEY2 |
| TGF-β Signaling | 1.67E00 | 1.12E−01 | MAPK3, PIAS4, FOS, JUN, SMAD3, BMP7, RUNX2, INHBA, BMP4, BMPR1B |
| G-Protein Coupled Receptor Signaling | 1.66E00 | 7.78E−02 | RXFP1, ADRB2, MAPK3, CAMK2D, PDE9A, HTR1B, DUSP9, CAMK4, FZD6, ADCY2, S1PR3, CALCRL, LGR5, PDE3A, RGS16, SHC1, P2RY14, ADCY8, PTGER3, PLCB1, AGTR2, GPR50, PDE8A, GPR64, GPR146, FYN, PDE7B, PDE4D, ADORA2A, RGS7, FZD2, DUSP1, LYST, GPRC5B, PDE11A, GPR155, ADORA1, FZD5, CHUK, PROKR1, PTH1R |
| Estrogen-Dependent Breast Cancer Signaling | 1.66E00 | 1.14E−01 | HSD17B7, MAPK3, HSD17B4, IGF1, FOS, JUN, HSD17B12, EGFR |
| Ephrin Receptor Signaling | 1.65E00 | 8.54E−02 | MAPK3, EPHA2, DOK1, CXCL12, ITGA4, FYN, EPHA3, GNAZ, FIGF, GNG3, FGF1, EPHB2, EPHA4, SHC1, EPHA7, ACP1, GRIN2C |
| Relaxin Signaling | 1.65E00 | 8.92E−02 | RXFP1, MAPK3, PDE8A, PDE9A, GNAZ, PDE7B, PDE4D, ADCY2, GNG3, PDE11A, FOS, JUN, PDE3A, ADCY8 |
| BMP signaling pathway | 1.64E00 | 1.12E−01 | MAPK3, JUN, BMP7, RUNX2, CAMK4, BMP5, MAPK10, BMP4, BMPR1B |
| Role of NANOG in Mammalian Embryonic Stem Cell Pluripotency | 1.62E00 | 1.05E−01 | FZD6, FZD2, MAPK3, WNT5A, FZD5, SHC1, LIFR, JAK3, BMP7, BMP5, BMP4, BMPR1B |
| B Cell Activating Factor Signaling | 1.57E00 | 1.33E−01 | FOS, JUN, CHUK, MAP3K1, IKBKAP, MAPK10 |
| CD27 Signaling in Lymphocytes | 1.57E00 | 1.23E−01 | FOS, MAP3K5, JUN, CHUK, MAP3K1, IKBKAP, MAPK10 |
| Corticotropin Releasing Hormone Signaling | 1.56E00 | 8.82E−02 | ADCY2, JUND, MAPK3, GLI3, FOS, JUN, PRKD1, GLI1, NOS1, MEF2A, CAMK4, ADCY8 |
| RANK Signaling in Osteoclasts | 1.54E00 | 1.05E−01 | MAPK3, FOS, MAP3K5, JUN, CHUK, MAP3K1, GSN, CAMK4, MITF, MAPK10 |
| Breast Cancer Regulation by Stathmin1 | 1.51E00 | 8.65E−02 | ARHGEF6, MAPK3, PPP1R3D, ARHGEF3, PLCB1, TUBB3, CAMK1D, PRKD1, CAMK2D, CDKN1B, CAMK4, ADCY2, GNG3, CCNE1, SHC1, TRPC5, ADCY8, TUBB2B |
| Role of JAK1 and JAK3 in γc Cytokine Signaling | 1.51E00 | 1.16E−01 | IRS1, MAPK3, SOCS3, IRS4, IRS2, SHC1, JAK3, IL4R |
| NRF2-mediated Oxidative Stress Response | 1.48E00 | 8.85E−02 | JUND, MAPK3, JUNB, MAP3K5, PRKD1, SQSTM1, ABCC1, MAF, TXNRD1, MGST2, UBE2K, FOS, JUN, MAP3K1, MGST1, DNAJB9, EPHX1 |
| Hepatic Fibrosis/Hepatic Stellate Cell Activation | 1.48E00 | 9.52E−02 | VCAM1, A2M, SMAD3, FLT1, COL1A1, COL3A1, EGFR, PDGFRA, FIGF, FGF1, COL1A2, IGF1, MYH9, IL4R |
| Glycosphingolipid Biosynthesis - Gangliosseries | 1.45E00 | 7.94E−02 | ELOVL6, ST3GAL4, ST8SIA4, ELOVL2, ST3GAL1 |
| O-Glycan Biosynthesis | 1.45E00 | 1.06E−01 | ST3GAL4, WBSCR17, GALNT13, ST3GAL1, GALNT5 |
| Pyrimidine Metabolism | 1.44E00 | 6.49E−02 | APOBEC3B, CAD, CRMP1, ENTPD6, POLA1, POLE, ENPP1, CTPS, TXNRD1, RRM2, PAPD5, EHD4, DPYD, POLE2, PNP |
| Colorectal Cancer Metastasis Signaling | 1.43E00 | 8.17E−02 | MAPK3, PTGER3, WNT5A, SMAD3, EGFR, FIGF, ADCY2, GNG3, FZD6, RHOB, FZD2, FOS, RHOU, JUN, FZD5, LEF1, JAK3, MMP15, ADCY8, ADRBK2, MAPK10 |
| Thrombopoietin Signaling | 1.41E00 | 1.11E−01 | MAPK3, FOS, JUN, PRKD1, GAB2, IRS2, SHC1 |
| Reelin Signaling in Neurons | 1.41E00 | 1.1E−01 | ARHGEF6, ARHGEF3, ITGA6, ITGA4, FYN, VLDLR, DCX, ARHGEF9, MAPK10 |
| Regulation of IL-2 Expression in Activated and Anergic T Lymphocytes | 1.41E00 | 1.01E−01 | MAPK3, FOS, JUN, SMAD3, CHUK, MAP3K1, FYN, CAMK4, MAPK10 |

| Ingenuity Canonical Pathways | −log(p-value) | Ratio | Molecules |
|---|---|---|---|
| Purine Metabolism | 1.4E00 | 5.92E−02 | HSPD1, ADSL, PDE9A, ABCC1, POLE, POLA1, ADCY2, RRM2, ADSSL1, PAPD5, PDE3A, POLE2, ADCY8, ENPP2, AK1, PDE8A, ENTPD6, ENPP1, PDE7B, PRPS2, PDE4D, ABCD3, PDE11A, BCKDHB, MYH9, PNP |
| Synaptic Long Term Depression | 1.39E00 | 8.54E−02 | GRIA1, MAPK3, RYR2, PLCB1, PRKD1, NOS1, PNPLA3, GNAZ, ADCY2, GRIA3, IGF1, GRIA4, PLA2G7, ADCY8 |
| Human Embryonic Stem Cell Pluripotency | 1.39E00 | 8.5E−02 | WNT5A, SMAD3, PDGFRA, BMP5, BMPR1B, FZD6, S1PR3, FZD2, FZD5, NTF3, LEF1, BMP7, BMP4 |
| Pantothenate and CoA Biosynthesis | 1.38E00 | 6.25E−02 | ENPP2, DPYD, CRMP1, ENPP1 |
| Pancreatic Adenocarcinoma Signaling | 1.36E00 | 9.24E−02 | MAPK3, TFDP1, NOTCH1, SMAD3, CCNE1, JAK3, CDKN1B, EGFR, FIGF, MAPK10, PLD2 |
| IL-9 Signaling | 1.35E00 | 1.25E−01 | IRS1, SOCS3, IRS2, JAK3, SOCS2 |
| Valine, Leucine and Isoleucine Degradation | 1.34E00 | 7.21E−02 | MUT, ELOVL6, HSD17B4, BCKDHB, ELOVL2, ACAT2, Aldh1a7, HMGCS1 |
| IL-22 Signaling | 1.32E00 | 1.6E−01 | MAPK3, SOCS3, IL10RB, MAPK10 |
| Glioma Signaling | 1.31E00 | 8.93E−02 | MAPK3, IGF1, TFDP1, CAMK1D, PRKD1, CAMK2D, SHC1, EGFR, PDGFRA, CAMK4 |
| Protein Kinase A Signaling | 1.31E00 | 7.74E−02 | MAPK3, RYR2, PRKD1, ADD3, CAMK2D, PDE9A, CAMK4, ADCY2, GNG3, PDE3A, ADCY8, PPP1R3D, PLCB1, GLI3, PHKA2, SMAD3, PDE8A, PLCL1, PDE7B, PDE4D, PDE11A, CHUK, MAP3K1, H3F3C, LEF1 |
| EGF Signaling | 1.31E00 | 1.15E−01 | MAPK3, FOS, JUN, MAP3K1, SHC1, EGFR |
| Sphingosine-1-phosphate Signaling | 1.31E00 | 9.24E−02 | ADCY2, SMPD2, RHOB, S1PR3, MAPK3, PLCB1, RHOU, PLCL1, SMPD3, PDGFRA, ADCY8 |
| Chemokine Signaling | 1.31E00 | 1.08E−01 | MAPK3, PLCB1, FOS, CAMK1D, JUN, CXCL12, CAMK2D, CAMK4 |
| FGF Signaling | 2.66E−01 | 5.56E−02 | FGF1, MAPK3, MAP3K5, MAP3K1, FGF12 |

TABLE 3

Ingenuity Wnt, BMP, FGF signal
Selected differentially expressed transcripts from sheet 1 grouped by Wnt, BMP, or FGF signaling
(comparing expression of day 14 GFP + vs GFP neg sorted triplicates)

| ProbeSet ID | Cluster ID | GFP +1 | GFP +2 | GFP +3 | GFP −1 | GFP −2 | GFP −3 |
|---|---|---|---|---|---|---|---|
| 10400474 | 320 | 0.8372 | 0.9451 | 0.9514 | −0.847 | −0.986 | −0.901 |
| Wnt signaling: | | | | | | | |
| 10575034 | 186 | | | | | | |
| 10423825 | 424 | | | | | | |
| 10485405 | 412 | | | | | | |
| 10567108 | 325 | | | | | | |
| 10514466 | 338 | | | | | | |
| 10355152 | 359 | | | | | | |
| 10513884 | 466 | | | | | | |
| 10432972 | 1024 | | | | | | |
| 10413482 | 614 | | | | | | |
| 10381603 | 995 | | | | | | |
| 10567010 | 629 | | | | | | |
| 10496091 | 1063 | | | | | | |
| 10408450 | 630 | | | | | | |
| 10492798 | 1215 | | | | | | |
| 10467006 | 892 | | | | | | |
| 10358210 | 690 | | | | | | |
| 10496125 | 976 | | | | | | |
| BMP signaling: | | | | | | | |
| 10557459 | 123 | | | | | | |
| 10454632 | 104 | | | | | | |
| 10419261 | 49 | | | | | | |
| 10514466 | 338 | | | | | | |
| 10451061 | 1052 | | | | | | |
| 10490129 | 780 | | | | | | |
| 10587231 | 865 | | | | | | |
| 10531869 | 880 | | | | | | |
| 10502451 | 822 | | | | | | |

TABLE 3-continued

Ingenuity Wnt, BMP, FGF signal
Selected differentially expressed transcripts from sheet 1 grouped by Wnt, BMP, or FGF signaling
(comparing expression of day 14 GFP + vs GFP neg sorted triplicates)

FGF signaling:

| 10458560 | 99 |

| ProbeSet ID | Cluster ID | logFC | P.Value | adj.P.Val. | Gene Symbol | mRNA Accession | mRNA Source |
|---|---|---|---|---|---|---|---|
| 10400474 | 320 | 2.391367333 | 4.10E−10 | 1.19E−05 | Nkx2-1 | NM_009385 | RefSeq |
| Wnt signaling: | | | | | | | |
| 10575034 | 186 | 0.801622 | 0.000212304 | 0.012269232 | Cdh3 | NM_001037809 | RefSeq |
| 10423825 | 424 | 0.659123333 | 0.000162158 | 0.01045415 | Fzd6 | NM_008056 | RefSeq |
| 10485405 | 412 | 0.850992 | 4.27E−05 | 0.004637288 | Cd44 | NM_009851 | RefSeq |
| 10567108 | 325 | 0.881975667 | 1.34E−06 | 0.000490872 | Sox6 | NM_011445 | RefSeq |
| 10514466 | 338 | 0.782238667 | 4.68E−05 | 0.004897346 | Jun | NM_010591 | RefSeq |
| 10355152 | 359 | 0.455571 | 0.001583745 | 0.042229802 | Fzd5 | NM_022721 | RefSeq |
| 10513884 | 466 | 0.472687667 | 0.000651826 | 0.024947378 | Tle1 | NM_011599 | RefSeq |
| 10432972 | 1024 | −0.548209667 | 0.000216751 | 0.012451795 | Rarg | NM_011244 | RefSeq |
| 10413482 | 614 | −1.078445667 | 5.01E−05 | 0.005137009 | Wnt5a | NM_009524 | RefSeq |
| 10381603 | 995 | −0.471290333 | 0.000326771 | 0.016154135 | Fzd2 | NM_020510 | RefSeq |
| 10567010 | 629 | −0.470603333 | 0.000588472 | 0.023744311 | Dkk3 | NM_015814 | RefSeq |
| 10496091 | 1063 | −0.589222333 | 6.89E−5 | 0.006059041 | Lef1 | NM_010703 | RefSeq |
| 10408450 | 630 | −0.495755667 | 0.000478469 | 0.020779716 | Sox4 | NM_009238 | RefSeq |
| 10492798 | 1215 | −1.670722 | 4.88E−08 | 8.11E−05 | Sfrp2 | NM_009144 | RefSeq |
| 10467006 | 892 | −1.208143 | 4.00E−05 | 0.004462778 | Dkk1 | NM_010051 | RefSeq |
| 10358210 | 690 | −0.374860333 | 0.000617733 | 0.024119868 | Nr5a2 | NM_030676 | RefSeq |
| 10496125 | 976 | −0.707198667 | 0.000348063 | 0.016776324 | Dkk2 | NM_020265 | RefSeq |
| BMP signaling: | | | | | | | |
| 10557459 | 123 | 0.442941333 | 0.000311508 | 0.015744197 | Mapk3 | NM_011952 | RefSeq |
| 10454632 | 104 | 0.728387 | 9.28E−05 | 0.007372532 | Camk4 | NM_009793 | RefSeq |
| 10419261 | 49 | 0.966461667 | 1.42E−06 | 0.000507734 | Bmp4 | NM_007554 | RefSeq |
| 10514466 | 338 | 0.782238667 | 4.68E−05 | 0.004897346 | Jun | NM_010591 | RefSeq |
| 10451061 | 1052 | −0.482594333 | 0.000229037 | 0.012843016 | Runx2 | NM_009820 | RefSeq |
| 10490129 | 780 | −0.795655333 | 0.000483846 | 0.020863064 | Bmp7 | NM_007557 | RefSeq |
| 10587231 | 865 | −0.605049667 | 0.000360224 | 0.016937514 | Bmp5 | NM_007555 | RefSeq |
| 10531869 | 880 | −0.835231 | 5.23E−06 | 0.001158023 | Mapk10 | NM_009158 | RefSeq |
| 10502451 | 822 | −0.861263333 | 5.17E−06 | 0.001158023 | Bmpr1b | NM_007560 | RefSeq |
| FGF signaling: | | | | | | | |
| 10458560 | 99 | 1.430725667 | 6.67E−06 | 0.001306841 | Fgf1 | NM_010197 | RefSeq |
| 10557459 | 123 | 0.442941333 | 0.000311508 | 0.015744197 | Mapk3 | NM_011952 | RefSeq |
| 10361926 | 45 | 0.793780333 | 8.84E−06 | 0.001592908 | Map3k5 | NM_008580 | RefSeq |
| 10412100 | 420 | 0.609978333 | 4.62E−05 | 0.004873776 | Map3k1 | NM_011945 | RefSeq |
| 10438801 | 33 | 0.627562333 | 4.56E−05 | 0.004835291 | Fgf12 | NM_183064 | RefSeq |

What is claimed:

1. An ex vivo or in vitro method for producing a mature thyroid follicular epithelial cell comprising:
   a) contacting an endodermal cell with a thyroid lineage culture medium to differentiate the endodermal cell into the thyroid lineage without exogenously delivered nucleic acid sequences resulting in the forced over-expression of the Nkx2-1 protein and the Pax8 protein in the endodermal cell, thereby producing a Nkx2.1+ and Pax8+ thyroid progenitor cell, wherein the thyroid lineage culture medium comprises:
      i) bone morphogenetic protein 4 (BMP4), and
      ii) fibroblast growth factor 2 (basic) (FGF2), and
   wherein the thyroid lineage culture medium does not contain:
      iii) Wingless-Type MMTV Integration Site Family protein, member 3A, (Wnt3A),
      iv) fibroblast Growth Factor 10 ((FGF10),
      v) keratinocyte Growth Factor (KGF), and
      vi) epidermal growth factor (EGF),
   b) isolating and culturing the Nkx2-1+/Pax8+ thyroid progenitor cell of step (a) in a differentiation medium comprising fibroblast growth factor 2 (basic) (FGF2) for a time sufficient to permit differentiation of the Nkx2-1+/Pax8+ thyroid progenitor cell along the thyroid lineage; and
   c) culturing the further differentiated cell produced in step (b) in a maturation medium comprising dexamethasone and thyroid stimulating hormone (TSH), under conditions and for a time sufficient to produce a Nkx2-1+/Pax8+ co-expressing cell that also expresses early and mature thyroid markers: thyroglobulin (Tg+), thyroid stimulating hormone receptor (Tsh+), sodium iodine symporter (Nis+), and thyroid peroxidase (Tpo+), thereby producing a mature thyroid follicular epithelial cell.

2. The method according to claim 1, wherein the endodermal cell is an anterior/foregut endodermal cell.

3. The method according to claim 1, wherein the differentiation medium further comprises one or more factors selected from the group consisting of a fibroblast growth factor, BMP4, and TSH.

4. The method according to claim 3, wherein the fibroblast growth factor is FGF2 or FGF10.

5. The method according to claim 1, wherein the resultant Nkx2-1+/Pax8+/Tg+/Tsh+/Nis+/Tpo+ cells do not express differentiated lung markers: surfactant, pulmonary-associated protein C (Sftpc) and secretoglobin family 1A member 1 (Scgb1a1).

6. The method according to claim 1, wherein the resultant Nkx2-1+/Pax8+/Tg+/Tsh+/Nis+/Tpo+ cells also express Forkhead Box E1 protein (Foxe1) and thyroidally-expressed homeobox protein (Hhex).

7. The method according to claim 1, wherein the resultant Nkx2-1+/Pax8+/Tg+/Tsh+/Nis+/Tpo+ cells also express epithelial markers E-Cadhedrin (E-Cad) and epithelial cell adhesion molecule (EpCam).

8. The method according to claim 1, the method further comprising selecting for Nkx2-1+/Pax8+ expressing cells by removing Nkx2-1+/Pax8−, Nkx2-1−/Pax8−, and Nkx2-1−/Pax8+ expressing cells.

9. The method according to claim 1, the method further comprising determining diploid expression of Nkx2-1 in the resultant cells.

10. The method according to claim 1, the method further comprising selecting for Nkx2-1+/Pax8+/Tg+/Tsh+/Nis+/Tpo+/expressing cells obtained.

11. The method according to claim 10, the method further comprising selecting for (I) Foxe1+/Hhex+expressing cells; (II) E-Cad+/EpCam+ expressing cells; (III) Sftpc−/Scgb1a1− expressing cells obtained; or a combination of (I), (II) and (III).

12. The method according to claim 1, wherein in the Nkx2-1+/Pax8+ expressing cells are cultured in a 3D matrix support material.

13. The method according to claim 12, wherein the 3D matrix support material is matrigel.

14. The method of claim 1, wherein the thyroid follicular epithelial cell is functional.

15. The method of claim 14, wherein the functional thyroid follicular epithelial cell can metabolize iodine, secretes thyroid hormones, expresses enzymes necessary for thyroid hormone synthesis and iodide metabolism and responds to the presence of TSH by secreting thyroid hormones.

16. The method of claim 1, wherein the time sufficient to permit differentiation of the Nkx2-1+/Pax8+ thyroid progenitor cell along the thyroid lineage is 8 days.

17. The method of claim 1, wherein step (c) is initiated when the cells are at days 22-26 of the method.

* * * * *